US011207320B2

(12) United States Patent
De Waal et al.

(10) Patent No.: US 11,207,320 B2
(45) **Date of Patent: *Dec. 28, 2021**

(54) COMPOSITIONS AND METHODS FOR CANCER EXPRESSING PDE3A OR SLFN12

(71) Applicants: The Broad Institute, Inc., Cambridge, MA (US); Dana-Farber Cancer Institute, Inc., Boston, MA (US); Bayer Pharma Aktiengesellschaft, Berlin (DE)

(72) Inventors: Luc De Waal, Boston, MA (US); Matthew Meyerson, Boston, MA (US); Heidi Greulich, Boston, MA (US); Monica Schenone, Boston, MA (US); Alex Burgin, Cambridge, MA (US); Xiaoyun Wu, Cambridge, MA (US); Ulrike Sack, Monheim Am Rhein (DE)

(73) Assignees: The Broad Institute, Inc., Cambridge, MA (US); Dana-Farber Cancer Institute, Inc., Boston, MA (US); Bayer Pharma Aktiengesellschaft, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/752,130

(22) PCT Filed: Aug. 12, 2016

(86) PCT No.: PCT/US2016/046912

§ 371 (c)(1),
(2) Date: Feb. 12, 2018

(87) PCT Pub. No.: WO2017/027854

PCT Pub. Date: Feb. 16, 2017

(65) Prior Publication Data

US 2018/0235961 A1 Aug. 23, 2018

Related U.S. Application Data

(60) Provisional application No. 62/204,875, filed on Aug. 13, 2015.

(51) Int. Cl.

| | |
|---|---|
| ***A61K 31/50*** | (2006.01) |
| ***G01N 33/574*** | (2006.01) |
| ***A61P 35/00*** | (2006.01) |
| ***A61K 9/00*** | (2006.01) |
| ***A61K 31/519*** | (2006.01) |

(52) U.S. Cl.

CPC ............ *A61K 31/50* (2013.01); *A61K 9/0019* (2013.01); *A61K 9/0053* (2013.01); *A61K 31/519* (2013.01); *A61P 35/00* (2018.01); *G01N 33/57488* (2013.01); *A61K 2300/00* (2013.01); *G01N 2333/916* (2013.01); *G01N 2800/52* (2013.01)

(58) Field of Classification Search

CPC .... A61K 31/50; A61K 31/519; A61K 9/0019; A61K 9/0053; A61P 35/00; G01N 2333/916; G01N 2800/52; G01N 33/57488

See application file for complete search history.

(56) References Cited

U.S. PATENT DOCUMENTS

| | | | | |
|---|---|---|---|---|
| 4,052,395 | A | 10/1977 | Jojima et al. | |
| 4,092,311 | A | 5/1978 | Hanifin et al. | |
| 4,661,486 | A | 4/1987 | Takeshiba et al. | |
| 5,053,338 | A | 10/1991 | Bray et al. | |
| 2004/0147540 | A1 * | 7/2004 | Flaumenhaft ........ | A61K 31/215 514/290 |
| 2013/0158023 | A1 | 6/2013 | Ning et al. | |

FOREIGN PATENT DOCUMENTS

| | | | |
|---|---|---|---|
| EP | 0791584 | A1 | 8/1997 |
| EP | 2253625 | A1 | 11/2010 |
| JP | H05140116 | A | 6/1993 |
| JP | 5852759 | B1 | 2/2016 |
| WO | 1992012135 | A1 | 7/1992 |
| WO | 2014164704 | A2 | 10/2014 |
| WO | 2015055898 | A2 | 4/2015 |
| WO | 2017134231 | A1 | 8/2017 |

OTHER PUBLICATIONS

U.S. Appl. No. 16/075,077, filed Aug. 2018, Lewis et al.*

Mavrommatis et al. Journal of Interferon and Cytokine Research, vol. 33, No. 4, 2013 pp. 206-210 (Year: 2013).*

De Waal, L. et al., "Indentification of cancer-cytotoxic modulators of PDE3A by predictive chemogenomics," Nature Chemical Biology, Dec. 14, 2015, vol. 12; pp. 102-108; DOI: 10.1038/nchembio.1984.

Kovalenko, P. et al., "Schlafen 12 expression modulates prostate cancer cell differentiation," Journal of Surgical Research, Jul. 2014, vol. 190, No. 1: pp. 177-184; abstract.

Pozuelo Rubio M., et al., "Phospodiesterase 3A binds to 14-3-3 proteins in response to PMA-induced phosphorylation of Ser428," Biochemistry Journal, Nov. 15, 2005, vol. 392, Pt. 1, pp. 163-172; Figure 2, p. 165, 1st col. 2nd paragraph; p. 167, 2nd col. 2nd paragraph: DOI: 10.1042/BJ200511003.

(Continued)

*Primary Examiner* — Kara R McMillian

(74) *Attorney, Agent, or Firm* — Melissa Hunter-Ensor; Scott Goncher; Greenberg Traurig, LLP

(57) ABSTRACT

The present invention features improved methods of identifying patients having cancer (e.g., melanoma, adenocarcinoma, lung, cervical, liver or breast cancer) using biomarkers (e.g., PDE3A, SLFN12) that correlate with drug sensitivity and consequently treating a stratified patient population with an agent of the invention (e.g., DNMDP, zardaverine, and anagrelide).

10 Claims, 26 Drawing Sheets

Specification includes a Sequence Listing.

(56) References Cited

OTHER PUBLICATIONS

International Search Report and Written Opinion for corresponding PCT Patent Application No. PCT/US16/46912, dated Dec. 12, 2016 (10 pages).

Edmondson et al., "Benzylvinylogous amide substituted aryldihydropyridazinones and aryldimethylpyrazolones as potent and selective PDE3B inhibitors," Bioorganic & Medicinal Chemistry Letters, Nov. 17, 2003.

Howson et al. "Synthesis and biological activity of the four stereoisomers of 6-[4-[3-[[2-hydroxy-3-[4-[2-(cyclopropylmethoxy)ethyl]phenoxy]propyl]amino]-propionamido]phenyl]-5-methyl-4,5-dihydro-3(2H)-pyridazinone, a combined vasodilator and .beta.-adrenoreceptor antagonist," Journal of Medicinal Chemistry, 1988, vol. 31, No. 2, pp. 352-356.

Lewis et al., "Abstract 5880: Small-molecule modulators of PDE3/SLFN12 to kill cancer cells," Cancer Research, AACR Journals, 2018, vol. 78, No. 13.

Seki et al., "Studies on agents with vasodilator and .beta.-blocking activities. V. Synthesis and pharmacological activity of the optical isomers of TZC-5665," Chemical and Pharmaceutical Bulletin, 1998, vol. 46, No. 1, pp. 84-96.

Varnerin et al., "Expression, refolding, and purification of recombinant human phosphodiesterase 3B: definition of the N-terminus of the catalytic core," Protein Expression and Purification, Jun. 2004.

Extended European Search Report for corresponding European Patent Application No. 16836014.7, dated Jan. 10, 2019 (10 pages).

* cited by examiner (R)-DNMDP

2

3

| | HeLa parental line | | HeLa resistant line | |
|---|---|---|---|---|
| Gene_Name | Hela_FPKM | Hela-P2_FPKM | Hela-Res1_FPKM | Hela-Res2_FPKM |
| SLFN12 | 12.51 | 12.63 | 0.15 | 0 |
| PDE3A | 56.24 | 62.15 | 53.46 | 54.91 |

| | H2122 parental line | | H2122 resistant line | |
|---|---|---|---|---|
| Gene_Name | H2122-P1_FPKM | H2122-P2_FPKM | H2122-Res1_FPKM | H2122-Res2_FPKM |
| SLFN12 | 4.69 | 5.15 | 0.33 | 0.46 |
| PDE3A | 25.52 | 25.24 | 15.82 | 15.13 |

COMPOSITIONS AND METHODS FOR CANCER EXPRESSING PDE3A OR SLFN12

CROSS-REFERENCE TO RELATED APPLICATIONS

This application is the U.S. national phase application, pursuant to 35 U.S.C. § 371, of PCT International Application Serial No.: PCT/US2016/046912, filed Aug. 12, 2016, designating the United States and published in English, which claims priority to and the benefit of U.S. Provisional Application No. 62/204,875, filed Aug. 13, 2015, the disclosure of which is incorporated herein by reference in its entirety.

STATEMENT OF RIGHTS TO INVENTIONS MADE UNDER FEDERALLY SPONSORED RESEARCH

This invention was made with Government support under Grant No. 3U54HG005032 awarded by the National Institutes of Health. The Government has certain rights in the invention.

BACKGROUND OF THE INVENTION

Cancer kills over 550,000 people in the United States and over 8 million people world-wide each year. New agents, including small molecules, molecules that impact tissue-specific growth requirements, and immunomodulatory agents, have been shown to benefit a subset of patients whose cancers have unique genomic mutations or other characteristics. Unfortunately, many cancer patients are still left without effective therapeutic options.

One approach to identify new anti-cancer agents is phenotypic screening to discover novel small molecules displaying strong selectivity between cancer cell lines, followed by chemogenomics to identify the cell features associated with drug response. In the 1990s, Weinstein and colleagues demonstrated that the cytotoxic profile of a compound can be used to identify cellular characteristics, such as gene-expression profiles and DNA copy number that correlate with drug sensitivity. The ability to identify the features of cancer cell lines that mediate their response to small molecules has strongly increased in recent years with automated high-throughput chemosensitivity testing of large panels of cell lines coupled with comprehensive genomic and phenotypic characterization of the cell lines. Phenotypic observations of small-molecule sensitivity can be linked to expression patterns or somatic alterations, as in the case of SLFN11 expression in cancer cell lines sensitive to irinotecan treatment, and an EWS-FLI1 rearrangement in cancer cell lines sensitive to PARP inhibitors, respectively.

Methods of characterizing malignancies at a molecular level are useful for stratifying patients, thereby quickly directing them to effective therapies. Improved methods for characterizing the responsiveness of subjects having cancer are urgently required.

SUMMARY OF THE INVENTION

As described below, the present invention features methods of identifying patients having a cancer (e.g., melanoma, adenocarcinoma, lung, cervical, liver, endometrium, lung, hematopoetic/lymphoid, ovarian, cervical, soft-tissue sarcoma, leiomyosarcoma, urinary tract, pancreas, thyroid, kidney, glioblastoma, or breast cancer) that is sensitive to treatment with a phosphodiesterase 3A (PDE3A) modulator (e.g., 6-(4-(diethylamino)-3-nitrophenyl)-5-methyl-4,5-dihydropyridazin-3(2H)-one, zardaverine, and anagrelide) by detecting co-expression of PDE3A and Schlafen 12 (SLFN12) polynucleotides or polypeptides in a cancer cell derived from such patients.

In one embodiment, the present invention provides a method of killing or reducing the survival of a cancer cell selected as responsive to a phosphodiesterase 3A (PDE3A) modulator. The method includes the step of contacting the cell with a PDE3A modulator, where the cell was selected as having an increase in PDE3A and/or Schlafen 12 (SLFN12) polypeptide or polynucleotide relative to a reference, thereby reducing the survival of the cancer cell. In another embodiment, the present invention provides a method of reducing cancer cell proliferation in a subject pre-selected as having a cancer that is responsive to a PDE3A modulator. The method comprises administering to the subject a PDE3A modulator, wherein the subject is pre-selected by detecting an increase in PDE3A and/or SLFN12 polypeptide or polynucleotide levels relative to a reference, thereby reducing cancer cell proliferation in the subject. In one embodiment, the subject is pre-selected by detecting an increase in PDE3A and/or SLFN12 polypeptide or polynucleotide levels. In some embodiments, the PDE3A modulator is selected from the group consisting of 6-(4-(diethylamino)-3-nitrophenyl)-5-methyl-4,5-dihydropyridazin-3(2H)-one (DNMDP), zardaverine, and anagrelide.

In another embodiment, the present invention provides a method of identifying a subject having a cancer responsive to PDE3A modulation. The method includes the step of detecting an increase in the level of a PDE3A and/or SLFN12 polypeptide or polynucleotide in a biological sample of the subject relative to a reference, thereby identifying the subject as responsive to PDE3A modulation. In one embodiment, an increase in the level of PDE3A and SFLN1 polypeptide or polynucleotide is detected.

In some embodiments, the increase in the level of PDE3A and/or SLFN12 polypeptide is detected by a method selected from the group consisting of immunoblotting, mass spectrometry, and immunoprecipitation. In some other embodiments, the increase in the level of PDE3A, and/or SLFN12 polynucleotide is detected by a method selected from the group consisting of quantitative PCR, Northern Blot, microarray, mass spectrometry, and in situ hybridization. In some embodiments, the activity of PDE3A is reduced. The PDE3A modulator may be administered orally. The PDE3A modulator may be administered by intravenous injection.

In some embodiments, the cancer cell is a melanoma, endometrium, lung, hematopoetic/lymphoid, ovarian, cervical, soft-tissue sarcoma, leiomyosarcoma, urinary tract, pancreas, thyroid, kidney, glioblastoma, or breast cancer. In some other embodiments, the cancer cell is not a B-cell proliferative type cancer. In some embodiments, the cancer cell is not multiple myeloma. In some embodiments, the biological sample is a tissue sample.

In another aspect, the present invention provides a kit for identifying a subject having cancer as responsive to PD3A modulation, the kit comprising a capture reagent that binds PDE3A and/or a capture reagent that binds SLFN12. In one embodiment, the kit comprises a capture reagent that binds PDE3A and a capture reagent that binds SLFN12.

In yet another aspect, the present invention provides a kit for decreasing cancer cell proliferation in a subject pre-selected as responsive to a PDE3A modulator, the kit comprising DNMDP, zardaverine, and/or anagrelide.

The invention provides methods for treating subjects having cancer identified as responsive to treatment with a PDE3A modulator by detecting co-expression of PDE3A and/or Schlafen 12 (SLFN12) polynucleotides or polypeptides in the cancer. Compositions and articles defined by the invention were isolated or otherwise manufactured in connection with the examples provided below. Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "Anagrelide" (IUPAC Name 6,7-dichloro-1,5-dihydroimidazo (2,1-b)quinazolin-2(3H)-one) is meant a small molecule phosphodiesterase inhibitor having the following structure:

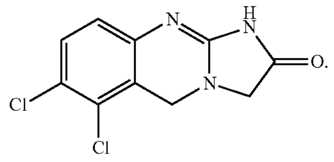 [SMILES: O=C1CN2Cc3c(ccc(Cl)c3Cl)N=C2N1]

By "Cilostamide" (IUPAC Name N-cyclohexyl-N-methyl-4-[(2-oxo-1H-quinolin-6-yeoxy]butanamide) is meant a small molecule inhibitor having the following structure:

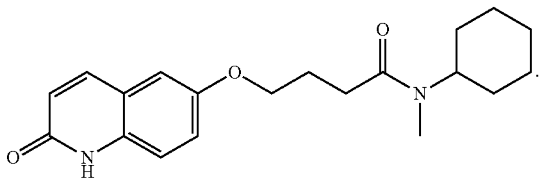 [SMILES: CN(C(=O)CCCOc1ccc2[nH]c(=O)ccc2c1)C1CCCCC1]

By "Cilostazol" (IUPAC Name 6-[4-(1-cyclohexyl-1H-tetrazol-5-yl)butoxy]-3,4-dihydro-2(1H)-quinolinone) is meant a small molecule inhibitor having the following structure:

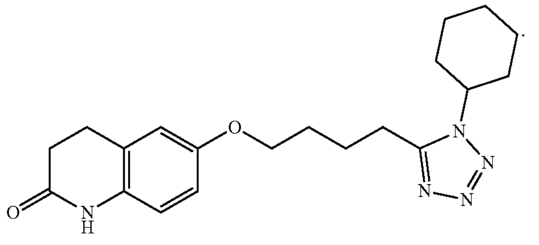 [SMILES: O=C1CCc2cc(OCCCCc3nnnn3C3CCCCC3)ccc2N1]

By "DNDMP" (IUPAC Name 6-(4-(diethylamino)-3-nitrophenyl)-5-methyl-4,5-dihydropyridazin-3(2H)-one) is meant a small molecule inhibitor having the following structure:

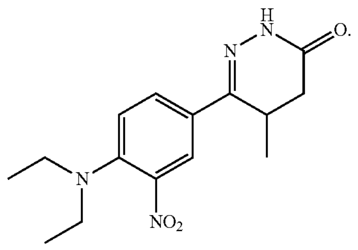 [SMILES: CCN(CC)c1ccc(C2=NNC(=O)CC2C)cc1[N+](=O)[O-]]

By "Forskolin" (IUPAC Name (3R,4aR,5S,6S,6aS,10S,10aR,10bS)-6,10,10b-Trihydroxy-3,4a,7,7,10a-pentamethyl-1-oxo-3-vinyldodecahydro-1H-benzo[f]chromen-5-ylacetate) is meant a small molecule inhibitor having the following structure:

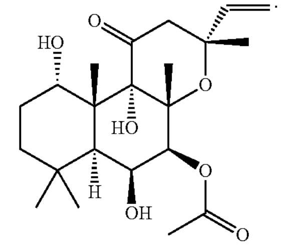

By "Levosimendan" (IUPAC Name (E)-2-cyano-1-methyl-3-(4-(4-methyl-6-oxo-1,4,5,6-tetrahydropyridazin-3-yl)phenyl)guanidine) is meant a small molecule inhibitor having the following structure:

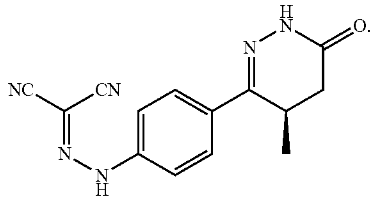 [SMILES: C[C@@H]1CC(=O)NN=C1c1ccc(NN=C(C#N)C#N)cc1]

By "Milrinone" (IUPAC Name 2-methyl-6-oxo-1,6-dihydro-3,4'-bipyridine-5-carbonitrile) is meant a small molecule inhibitor having the following structure:

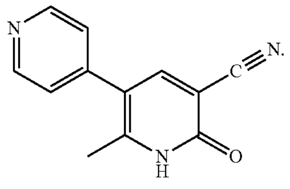 [SMILES: Cc1[nH]c(=O)c(C#N)cc1-c1ccncc1]

By "Papaverine" (IUPAC Name 1-(3,4-dimethoxybenzyl)-6,7-dimethoxyisoquinoline) is meant a small molecule inhibitor having the following structure:

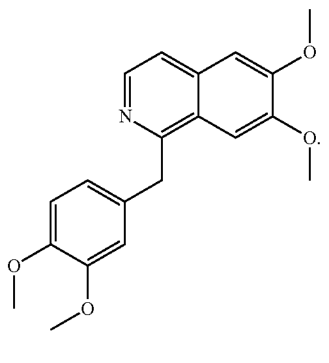 [SMILES: COc1ccc(Cc2nccc3cc(OC)c(OC)cc23)cc1OC]

By "Siguazodan" (IUPAC Name (E)-2-cyano-1-methyl-3-(4-(4-methyl-6-oxo-1,4,5,6-tetrahydropyridazin-3-yl)phenyl)guanidine) is meant a small molecule inhibitor having the following structure:

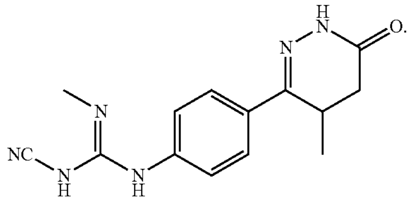 [SMILES: C/N=C(\NC#N)Nc1ccc(C2=NNC(=O)CC2C)cc1]

By "Sildenafil" (IUPAC Name 1-[4-ethoxy-3-(6,7-dihydro-1-methyl-7-oxo-3-propyl-1H-pyrazolo[4,3-d]pyrimidin-5-yl)phenylsulfonyl]-4- methylpiperazine) is meant a small molecule inhibitor having the following structure:

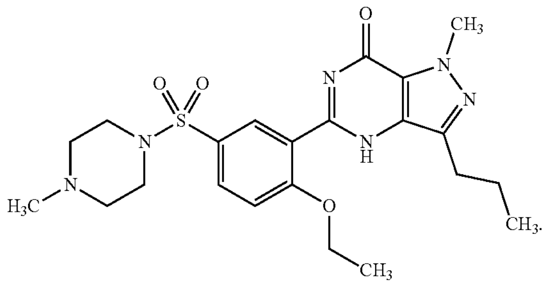 [SMILES: CCCc1nn(C)c2c(=O)nc(-c3cc(S(=O)(=O)N4CCN(C)CC4)ccc3OCC)[nH]c12]

By "Trequinsin" (IUPAC Name 9,10-dimethoxy-3-methyl-2-(2,4,6-trimethylphenyl)imino-6,7-dihydropyrimido[6,1-a]isoquinolin-4-one) is meant a small molecule inhibitor having the following structure:

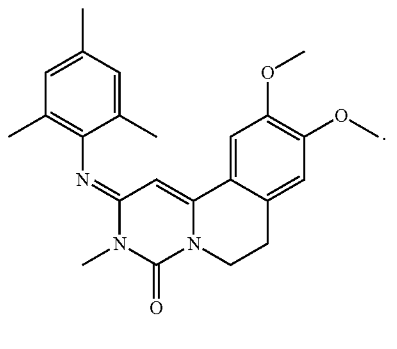

By "Vardenifil" (IUPAC Name 4-[2-ethoxy-5-(4-ethylpiperazin-1-yl)sulfonyl-phenyl]-9-methyl-7-propyl-3,5,6,8-tetrazabicyclo[4.3.0]nona-3,7,9-trien-2-one) is meant a small molecule inhibitor having the following structure:

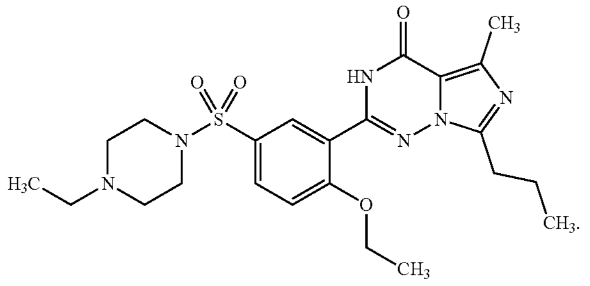 [SMILES: CCCc1nc(C)c2c(=O)[nH]c(-c3cc(S(=O)(=O)N4CCN(CC)CC4)ccc3OCC)nn12]

By "Zardaverine (IUPAC Name 3-[4-(Difluoromethoxy)-3-methoxyphenyl]-1H-pyridazin-6-one)" is meant a small molecule inhibitor having the following structure:

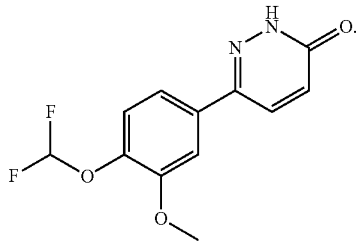 [SMILES: COc1cc(-c2ccc(=O)[nH]n2)ccc1OC(F)F]

In some other embodiments, any one of the compounds Cilostamide, Cilostazol, DNDMP, Levosimendan, Milrinone, Papaverine, Siguazodan, Sildenafil, Trequinsin, Vardenifil, and Zardaverine is a small molecule phosphodiesterase inhibitor. In another embodiment, forskolin may be used in a method of the invention.

By "PDE3A polypeptide" is meant a protein or fragment thereof having at least 85% amino acid sequence identity to the sequence provided at NCBI Ref No. NP_000912.3 that catalyzes the hydrolysis of cyclic adenosine monophosphate (cAMP) and cyclic guanosine monophosphate (cGMP). An exemplary human full-length PDE3A amino acid sequence is provided below:

```
                                    (SEQ ID NO.: 3)
MAVPGDAARVRDKPVHSGVSQAPTAGRDCHHRADPASPRDSGCRGCWGDL
VLQPLRSSRKLSSALCAGSLSFLLALLVRLVRGEVGCDLEQCKEAAAAEE
EEAAPGAEGGVFPGPRGGAPGGGARLSPWLQPSALLFSLLCAFFWMGLYL
LRAGVRLPLAVALLAACCGGEALVQIGLGVGEDHLLSLPAAGVVLSCLAA
ATWLVLRLRLGVLMIALTSAVRTVSLISLERFKVAWRPYLAYLAGVLGIL
LARYVEQILPQSAEAAPREHLGSQLIAGTKEDIPVFKRRRRSSSVVSAEM
SGCSSKSHRRTSLPCIPREQLMGHSEWDHKRGPRGSQSSGTSITVDIAVM
GEAHGLITDLLADPSLPPNVCTSLRAVSNLLSTQLTFQAIHKPRVNPVTS
LSENYTCSDSEESSEKDKLAIPKRLRRSLPPGLLRRVSSTWTTTTSATGL
PTLEPAPVRRDRSTSIKLQEAPSSSPDSWNNPVMMTLTKSRSFTSSYAIS
AANHVKAKKQSRPGALAKISPLSSPCSSPLQGTPASSLVSKISAVQFPES
ADTTAKQSLGSHRALTYTQSAPDLSPQILTPPVICSSCGRPYSQGNPADE
PLERSGVATRTPSRTDDTAQVTSDYETNNNSDSSDIVQNEDETECLREPL
RKASACSTYAPETMMFLDKPILAPEPLVMDNLDSIMEQLNTWNFPIFDLV
ENIGRKCGRILSQVSYRLFEDMGLFEAFKIPIREFMNYFHALEIGYRDIP
YHNRIHATDVLHAVWYLTTQPIPGLSTVINDHGSTSDSDSDSGFTHGHMG
YVFSKTYNVTDDKYGCLSGNIPALELMALYVAAAMHDYDHPGRTNAFLVA
TSAPQAVLYNDRSVLENHHAAAAWNLFMSRPEYNFLINLDHVEFKHFRFL
VIEAILATDLKKHFDFVAKFNGKVNDDVGIDWTNENDRLLVCQMCIKLAD
INGPAKCKELHLQWTDGIVNEFYEQGDEEASLGLPISPFMDRSAPQLANL
QESFISHIVGPLCNSYDSAGLMPGKWVEDSDESGDTDDPEEEEEEAPAPN
EEETCENNESPKKKTFKRRKIYOQITQHLLQNHKMWKKVIEEEQRLAGIE
NQSLDQTPQSHSSEQIQAIKEEEEEKGKPRGEEIPTQKPDQ
```

Three PDE3A isoforms are known: PDE3A1, PDE3A2, and PDE3A3. PDE3A1 comprises amino acids 146-1141, PDE3A2 isoform 2 comprises amino acids 299-1141, and PDE3A3 comprises amino acids 483-1141 of the full-length PDE3A amino acid sequence.

By "PDE3A polynucleotide" is meant any nucleic acid molecule, including DNA and RNA, encoding a PDE3A polypeptide or fragment thereof. An exemplary PDE3A nucleic acid sequence is provided at NCBI Ref: NM_000921.4:

```
                                    (SEQ ID NO.: 4)
   1 gggggccact gggaattcag tgaagagggc accctatacc
     atggcagtgc ccggcgacgc
  61 tgcacgagtc agggacaagc ccgtccacag tggggtgagt
     caagccccca cggcgggccg
 121 ggactgccac catcgtgcgg accccgcatc gccgcgggac
     tcgggctgcc gtggctgctg
```

-continued

```
 181 gggagacctg gtgctgcagc cgctccggag ctctcggaaa
     ctttcctccg cgctgtgcgc
 241 gggctccctg tcctttctgc tggcgctgct ggtgaggctg
     gtccgcgggg aggtcggctg
 301 tgacctggag cagtgtaagg aggcggcggc ggcggaggag
     gaggaagcag ccccgggagc
 361 agaaggggc gtcttcccgg ggcctcgggg aggtgctccc
     gggggcggtg cgcggctcag
 421 cccctggctg cagccctcgg cgctgctctt cagtctcctg
     tgtgccttct tctggatggg
 481 cttgtacctc ctgcgcgccg gggtgcgcct gcctctggct
     gtcgcgctgc tggccgcctg
 541 ctgcgggggg gaagcgctcg tccagattgg gctgggcgtc
     ggggaggatc acttactctc
 601 actccccgcc gcgggggtgg tgctcagctg cttggccgcc
     gcgacatggc tggtgctgag
 661 gctgaggctg ggcgtcctca tgatcgcctt gactagcgcg
     gtcaggaccg tgtccctcat
 721 ttccttagag aggttcaagg tcgcctggag accttacctg
     gcgtacctgg ccggcgtgct
 781 ggggatcctc ttggccaggt acgtggaaca aatcttgccg
     cagtccgcgg aggcggctcc
 841 aagggagcat ttggggtccc agctgattgc tgggaccaag
     gaagatatcc cggtgtttaa
 901 gaggaggagg cggtccagct ccgtcgtgtc cgccgagatg
     tccggctgca gcagcaagtc
 961 ccatcggagg acctccctgc cctgtatacc gagggaacag
     ctcatggggc attcagaatg
1021 ggaccacaaa cgagggccaa gaggatcaca gtcttcagga
     accagtatta ctgtggacat
1081 cgccgtcatg ggcgaggccc acggcctcat taccgacctc
     ctggcagacc cttctcttcc
1141 accaaacgtg tgcacatcct tgagagccgt gagcaacttg
     ctcagcacac agctcacctt
1201 ccaggccatt cacaagccca gagtgaatcc cgtcacttcg
     ctcagtgaaa actatacctg
1261 ttctgactct gaagagagct ctgaaaaaga caagcttgct
     attccaaagc gcctgagaag
1321 gagtttgcct cctggcttgt tgagacgagt ttcttccact
     tggaccacca ccacctcggc
```

-continued

```
1381 cacaggtcta cccaccttgg agcctgcacc agtacggaga
     gaccgcagca ccagcatcaa
1441 actgcaggaa gcaccttcat ccagtcctga ttcttggaat
     aatccagtga tgatgaccct
1501 caccaaaagc agatccttta cttcatccta tgctatttct
     gcagctaacc atgtaaaggc
1561 taaaaagcaa agtcgaccag gtgccctcgc taaaatttca
     cctctttcat cgccctgctc
1621 ctcacctctc caagggactc ctgccagcag cctggtcagc
     aaaatttctg cagtgcagtt
1681 tccagaatct gctgacacaa ctgccaaaca aagcctaggt
     tctcacaggg ccttaactta
1741 cactcagagt gccccagacc tatcccctca aatcctgact
     ccacctgtta tatgtagcag
1801 ctgtggcaga ccatattccc aagggaatcc tgctgatgag
     cccctggaga gaagtggggt
1861 agccactcgg acaccaagta gaacagatga cactgctcaa
     gttacctctg attatgaaac
1921 caataacaac agtgacagca gtgacattgt acagaatgaa
     gatgaaacag agtgcctgag
1981 agagcctctg aggaaagcat cggcttgcag cacctatgct
     cctgagacca tgatgtttct
2041 ggacaaacca attcttgctc ccgaacctct tgtcatggat
     aacctggact caattatgga
2101 gcagctaaat acttggaatt ttccaatttt tgatttagtg
     gaaaatatag gaagaaaatg
2161 tggccgtatt cttagtcagg tatcttacag actttttgaa
     gacatgggcc tctttgaagc
2221 ttttaaaatt ccaattaggg aatttatgaa ttattttcat
     gctttggaga ttggatatag
2281 ggatattcct tatcataaca gaatccatgc cactgatgtt
     ttacatgctg tttggtatct
2341 tactacacag cctattccag gcctctcaac tgtgattaat
     gatcatggtt caaccagtga
2401 ttcagattct gacagtggat ttacacatgg acatatggga
     tatgtattct caaaaacgta
2461 taatgtgaca gatgataaat acggatgtct gtctgggaat
     atccctgcct tggagttgat
2521 ggcgctgtat gtggctgcag ccatgcacga ttatgatcat
     ccaggaagga ctaatgcttt
2581 cctggttgca actagtgctc ctcaggcggt gctatataac
     gatcgttcag ttttggagaa
2641 tcatcacgca gctgctgcat ggaatctttt catgtcccgg
     ccagagtata acttcttaat
2701 taaccttgac catgtggaat ttaagcattt ccgtttcctt
     gtcattgaag caattttggc
2761 cactgacctg aagaaacact ttgacttcgt agccaaattt
     aatggcaagg taaatgatga
2821 tgttggaata gattggacca atgaaaatga tcgtctactg
     gtttgtcaaa tgtgtataaa
2881 gttggctgat atcaatggtc cagctaaatg taaagaactc
     catcttcagt ggacagatgg
2941 tattgtcaat gaattttatg aacagggtga tgaagaggcc
     agccttggat tacccataag
3001 ccccttcatg gatcgttctg ctcctcagct ggccaacctt
     caggaatcct tcatctctca
3061 cattgtgggg cctctgtgca actcctatga ttcagcagga
     ctaatgcctg gaaaatgggt
3121 ggaagacagc gatgagtcag gagatactga tgacccagaa
     gaagaggagg aagaagcacc
3181 agcaccaaat gaagaggaaa cctgtgaaaa taatgaatct
     ccaaaaaaga agactttcaa
3241 aaggagaaaa atctactgcc aaataactca gcacctctta
     cagaaccaca agatgtggaa
3301 gaaagtcatt gaagaggagc aacggttggc aggcatagaa
     aatcaatccc tggaccagac
3361 ccctcagtcg cactcttcag aacagatcca ggctatcaag
     gaagaagaag aagagaaagg
3421 gaaaccaaga ggcgaggaga taccaaccca aaagccagac
     cagtgacaat ggatagaatg
3481 ggctgtgttt ccaaacagat tgacttgtca aagactctct
     tcaagccagc acaacattta
3541 gacacaacac tgtagaaatt tgagatgggc aaatggctat
     tgcattttgg gattcttcgc
3601 attttgtgtg tatattttta cagtgaggta cattgttaaa
     aactttttgc tcaaagaagc
3661 tttcacattg caacaccagc ttctaaggat tttttaagga
     gggaatatat atgtgtgtgt
3721 gtatataagc tcccacatag atacatgtaa aacatattca
     cacccatgca cgcacacaca
```

-continued 3781 tacacactga aggccacgat tgctggctcc acaatttagt aacatttata ttaagatata
3841 tatatagtgg tcactgtgat ataataaatc ataaaggaaa ccaaatcaca aaggagatgg
3901 tgtggcttag caaggaaaca gtgcaggaaa tgtaggttac caactaagca gcttttgctc
3961 ttagtactga gggatgaaag ttccagagca ttatttgaat tctgatacat cctgccaaca
4021 ctgtgtgtgt gtgtgtgtgt gtgtgtgtgt gtgtgtgtgt gtgtgaaaga gagacagaag
4081 ggaatggttt gagagggtgc ttgtgtgcat gtgtgtgcat atgtaaagag atttttgtgg
4141 tttaagtaac tcagaatagc tgtagcaaat gactgaatac atgtgaacaa acagaaggaa
4201 gttcactctg gagtgtcttt gggaggcagc cattccaaat gccctcctcc atttagcttc
4261 aataaagggc cttttgctga tggagggcac tcaagggctg ggtgagaggg ccacgtgttt
4321 ggtattacat tactgctatg caccacttga aggagctcta tcaccagcct caaacccgaa
4381 agactgaggc attttccagt ctacttgcct aatgaatgta taggaactgt ctatgagtat
4441 ggatgtcact caactaagat caaatcacca tttaagggga tggcattctt tatacctaaa
4501 cacctaagag ctgaagtcag gtcttttaat caggttagaa ttctaaatga tgccagagaa
4561 ggcttgggaa attgtacttc agcgtgatag cctgtgtctt cttaatttgc tgcaaaatat
4621 gtggtagaga aagaaaagga aacagaaaaa tcactctggg ttatatagca agagatgaag
4681 gagaatattt caacacaggg tttttgtgtt gacataggaa aagcctgatt cttggcaact
4741 gttgtagttt gtctttcagg ggtgaaggtc ccactgacaa cccctgttgt ggtgttccac
4801 acgctgtttg ttggggtagc ttccatcggc agtctggccc attgtcagtc atgcttcttc
4861 tggccgggga gattatagag agattgtttg aagattgggt tattattgaa agtctttttt
4921 tttgtttgtt ttgttttggt ttgtttgttt atctacactt gtttatgctg tgagccaaac -continued 4981 ctctatttaa aaagttgata ctcactttca atattttatt tcatattatt atatatgtca
5041 tgatagttat cttgatgtaa atatgaagat ttttttgttt ctgtagatag taaactcttt
5101 ttttaaaaaa ggaaaaggga aacattttta taaagttata ttttaatcac catttttata
5161 cattgtagtt ctctccaagc ccagtaagag aatgatgatt catttgcatg gaggtcgatg
5221 gacaaccaat catctacctt ttctaattta aatgataatc tgatatagtt ttattgccag
5281 ttaaatgagg atgctgcaaa gcatgttttt tcactagtaa cttttgctaa ctgaatgaat
5341 tctgggtcca tatctcccag atgaaaaact gttaaccaat accatatttt atagttggtg
5401 tccatttctt tccaacactg tttgttatga ttcttccttg agtacttata tacagacctg
5461 ctcattatct aaacaatctt accttctaag taaaccttga ttgtgatttc cagtttttat
5521 tttctctgac gtagtagaaa ggaatgttta cattaaaaat acttttgttt ctcataaatg
5581 gatattgtac tccccccttt caaagcatta ttttacaata attcatggca ttttaaaaaa
5641 taaggcaaag ataatacgac aaaaaatata catggtttca aggcaaattc tccaataagt
5701 tggaaaatgt aaaaaggatc aagtggatgc agcctctacc taaataatta aaatatattt
5761 cagtatattt ctgaattaac accaggtctt cattatttag aacttactaa attgttttca
5821 ttttcttagt tttacctgtg tatctccatg tttgcaaaaa ttactataag tcaaattttg
5881 ccagtgaatt taactatttt tctttccttg caattaaggg gaaaaaagca tttatcttat
5941 cttctcatac cccttgcatc taagtactta gcaaagtcaa tattttccca ttttccaaat
6001 gcgtccatct ctaacataaa tattaattga acatagagct atgtttggag tgagtggact
6061 ggcaggacag ttggaagtcc atcacagtct attgacagtt tcatcaaagc tgtatagtcc
6121 aactagtggg gcagcttggc tactatggtg gaagtctcag caaactgcct ggttttgttt -continued

```
6181 gtttgttttg ttttaaggta caggaaataa gaggaataat
     agtggccaaa gcaattagaa
6241 catcttcatt ccagaactgt gttcagcaat ccaggcagat
     tgatacattt ttctttaaaa
6301 ataaattgct attacagcta gacgtcaatt gggataaata
     aagggatgaa gatccactaa
6361 gtttgtgact ttcatacaca cccagtacat ctcaaaggat
     gctaagggac attttctgcc
6421 agtagagttc tccccctttt tggtgacagc aatattatta
     tgttcacatc taactccaga
6481 gcttacttcc tgtggtgcca atgtatttgt tgcaatttac
     tacattttta tatgagccta
6541 tttataggtg ccattaaact caggtctttc aaatgaaaga
     gtttctagcc cacttaggga
6601 aaaagataat tgtttagaaa accataaaat caatggtagg
     aaaagttgga actggttacc
6661 tggatgccat ggttctctgt taaataaagt aagagaccag
     gtgtattctg agtgtcatca
6721 gtgttatttt cagcatgcta ataaatgtct ttccggttat
     atatctatct aaattaacct
6781 ttaaaatatt ggtttccttg ataaaagcac cacttttgct
     tttgttagct gtaatatttt
6841 ttgtcattta gataagacct ggtttggctc tcaataaaag
     atgaagacag tagctctgta
6901 cagggatata tctatattag tcttcatctg atgaatgaag
     aaattttctc atattatgtt
6961 caagaaagta tttacttcct aaaaatagaa ttcccgattc
     tgtctatttt ggttgaatac
7021 cagaacaaat ctttccgttg caatcccagt aaaacgaaag
     aaaaggaata tcttacagac
7081 tgttcatatt agatgtatgt agactgttaa tttgcaattt
     ccccatattt cctgcctatc
7141 ttacccagat aactttcttt gaaggtaaaa gctgtgcaaa
     aggcatgaga ctcaggccta
7201 ctctttgttt aaatgatgga aaaatataaa ttattttcta
     agtaataaaa gtataaaaat
7261 tatcattata aataaagtct aaagtttgaa attattaatt
     taaaaaaaaa aaaaaaaaa
```

By "Schlafen 12 (SLFN12) polypeptide" is meant a protein or fragment thereof having at least 85% amino acid sequence identity to the sequence provided at NCBI Ref No. NP_060512.3 that interacts with PDE3A when bound to anagrelide, zardaverine or DNMDP and related compounds. An exemplary human SLFN12 amino acid sequence is provided below:

```
                                                (SEQ ID NO.: 5)
MNISVDLETNYAELVLDVGRVTLGENSRKKMKDCKLRKKQNESVSRAMCA
LLNSGGGVIKAEIENEDYSYTKDGIGLDLENSFSNILLFVPEYLDFMQNG
NYFLIFVKSWSLNTSGLRITTLSSNLYKRDITSAKVMNATAALEFLKDMK
KTRGRLYLRPELLAKRPCVDIQEENNMKALAGVFFDRTELDRKEKLTFTE
STHVEIKNESTEKLLQRIKEILPQYVSAFANTDGGYLFIGLNEDKEIIGF
KAEMSDLDDLEREIEKSIRKMPVHHFCMEKKKINYSCKFLGVYDKGSLCG
YVCALRVERFCCAVFAKEPDSWHVKDNRVMQLTRKEWIQFMVEAEPKFSS
SYEEVISQINTSLPAPHSWPLLEWQRQRHHCPGLSGRITYTPENLCRKLF
LQHEGLKQLICEEMDSVRKGSLIFSRSWSVDLGLQENHKVLCDALLISQD
SPPVLYTFHMVQDEEFKGYSTQTALTLKQKLAKIGGYTKKVCVMTKIFYL
SPEGMTSCQYDLRSQVIYPESYYFTRRKYLLKALFKALKRLKSLRDQFSF
AENLYQIIGIDCFQKNDKKMFKSCRRLT
```

By "Schlafen 12 (SLFN12) polynucleotide" is meant any nucleic acid molecule, including DNA and RNA, encoding a SLFN12 polypeptide or fragment thereof. An exemplary SLFN12 nucleic acid sequence is provided at NCBI Ref: NM_018042.4:

```
                                                (SEQ ID NO.: 6)
  1 tttgtaactt cacttcagcc tcccattgat cgctttctgc
    aaccattcag actgatctcg
 61 ggctcctatt tcatttacat tgtgtgcaca ccaagtaacc
    agtgggaaaa ctttagaggg
121 tacttaaacc ccagaaaatt ctgaaaccgg gctcttgagc
    cgctatcctc gggcctgctc
181 ccaccctgtg gagtgcactt tcgttttcaa taaatctctg
    cttttgttgc ttcattcttt
241 ccttgctttg tttgtgtgtt tgtccagttc tttgttcaac
    acgccaagaa cctggacact
301 cttcactggt aacatatttt ggcaagccaa ccaggagaaa
    agaatttctg cttggacact
361 gcatagctgc tgggaaaatg aacatcagtg ttgatttgga
    aacgaattat gccgagttgg
421 ttctagatgt gggaagagtc actcttggag agaacagtag
    gaaaaaaatg aaggattgta
481 aactgagaaa aaagcagaat gaaagtgtct cacgagctat
    gtgtgctctg ctcaattctg
541 gagggggagt gatcaaggct gaaattgaga atgaagacta
    tagttataca aaagatggaa
```

-continued

```
601 taggactaga tttggaaaat tcttttagta acattctgtt
    atttgttcct gagtacttag
661 acttcatgca gaatggtaac tactttctga tttttgtgaa
    gtcatggagc ttgaacacct
721 ctggtctgcg gattaccacc ttgagctcca atttgtacaa
    aagagatata acatctgcaa
781 aagtcatgaa tgccactgct gcactggagt tcctcaaaga
    catgaaaaag actagaggga
841 gattgtattt aagaccagaa ttgctggcaa agaggccctg
    tgttgatata caagaagaaa
901 ataacatgaa ggccttggcc ggggtttttt ttgatagaac
    agaacttgat cggaaagaaa
961 aattgacctt tactgaatcc acacatgttg aaattaaaaa
    cttctcgaca gaaaagttgt
1021 tacaacgaat taaagagatt ctccctcaat atgtttctgc
    atttgcaaat actgatggag
1081 gatatttgtt cattggttta aatgaagata aagaaataat
    tggctttaaa gcagagatga
1141 gtgacctcga tgacttagaa agagaaatcg aaaagtccat
    taggaagatg cctgtgcatc
1201 acttctgtat ggagaagaag aagataaatt attcatgcaa
    attccttgga gtatatgata
1261 aaggaagtct tgtggatat gtctgtgcac tcagagtgga
    gcgcttctgc tgtgcagtgt
1321 ttgctaaaga gcctgattcc tggcatgtga aagataaccg
    tgtgatgcag ttgaccagga
1381 aggaatggat ccagttcatg gtggaggctg aaccaaaatt
    ttccagttca tatgaagagg
1441 tgatctctca aataaatacg tcattacctg ctccccacag
    ttggcctctt ttggaatggc
1501 aacggcagag acatcactgt ccagggctat caggaaggat
    aacgtatact ccagaaaacc
1561 tttgcagaaa actgttctta caacatgaag gacttaagca
    attaatatgt gaagaaatgg
1621 actctgtcag aaagggctca ctgatcttct ctaggagctg
    gtctgtggat ctgggcttgc
1681 aagagaacca caaagtcctc tgtgatgctc ttctgatttc
    ccaggacagt cctccagtcc
1741 tatacacctt ccacatggta caggatgagg agtttaaagg
    ctattctaca caaactgccc
```

-continued

```
1801 taaccttaaa gcagaagctg gcaaaaattg gtggttacac
     taaaaaagtg tgtgtcatga
1861 caaagatctt ctacttgagc cctgaaggca tgacaagctg
     ccagtatgat ttaaggtcgc
1921 aagtaattta ccctgaatcc tactatttta caagaaggaa
     atacttgctg aaagcccttt
1981 ttaaagcctt aaagagactc aagtctctga gagaccagtt
     ttcctttgca gaaaatctat
2041 accagataat cggtatagat tgctttcaga agaatgataa
     aaagatgttt aaatcttgtc
2101 gaaggctcac ctgatggaaa atggactggg ctactgagat
     atttttcatt atatatttga
2161 taacattctc taattctgtg aaaatatttc tttgaaaact
     ttgcaagtta agcaacttaa
2221 tgtgatgttg gataattggg ttttgtctat tttcacttct
     ccctaaataa tcttcacaga
2281 tattgtttga gggatattag gaaaattaat ttgttaactc
     gtctgtgcac agtattattt
2341 actctgtctg tagttcctga ataaattttc ttccatgctt
     gaactgggaa aattgcaaca
2401 cttttattct taatgacaac agtgaaaatc tcccagcata
     tacctagaaa acaattataa
2461 cttacaaaag attatccttg atgaaactca gaatttccac
     agtgggaatg aataagaagg
2521 caaaactcat
```

In some aspects, the compound is an isomer. "Isomers" are different compounds that have the same molecular formula. "Stereoisomers" are isomers that differ only in the way the atoms are arranged in space. As used herein, the term "isomer" includes any and all geometric isomers and stereoisomers. For example, "isomers" include geometric double bond cis- and trans-isomers, also termed E- and Z-isomers; R- and S-enantiomers; diastereomers, (d)-isomers and (l)-isomers, racemic mixtures thereof; and other mixtures thereof, as falling within the scope of this invention.

Geometric isomers can be represented by the symbol $\equiv$ which denotes a bond that can be a single, double or triple bond as described herein. Provided herein are various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring, and the term "trans" represents substituents on opposite sides of the plane of the ring. Mixtures of compounds wherein the substituents are disposed on both the same and opposite sides of plane of the ring are designated "cis/trans."

The term "enantiomers" refers to a pair of stereoisomers that are non-superimposable mirror images of each other. An atom having an asymmetric set of substituents can give rise to an enantiomer. A mixture of a pair of enantiomers in any proportion can be known as a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is an enantiomer, the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry at each asymmetric atom, as (R)- or (S)-. The present chemical entities, pharmaceutical compositions and methods are meant to include all such possible isomers, including racemic mixtures, optically substantially pure forms and intermediate mixtures.

Optically active (R)- and (S)-isomers can be prepared, for example, using chiral synthons or chiral reagents, or resolved using conventional techniques. Enantiomers can be isolated from racemic mixtures by any method known to those skilled in the art, including chiral high pressure liquid chromatography (HPLC), the formation and crystallization of chiral salts, or prepared by asymmetric syntheses.

Optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid. The separation of the mixture of diastereoisomers by crystallization followed by liberation of the optically active bases from these salts affords separation of the isomers. Another method involves synthesis of covalent diastereoisomeric molecules by reacting disclosed compounds with an optically pure acid in an activated form or an optically pure isocyanate. The synthesized diastereoisomers can be separated by conventional means such as chromatography, distillation, crystallization or sublimation, and then hydrolyzed to deliver the enantiomerically enriched compound. Optically active compounds can also be obtained by using active starting materials. In some embodiments, these isomers can be in the form of a free acid, a free base, an ester or a salt.

In certain embodiments, the compound of the invention can be a tautomer. As used herein, the term "tautomer" is a type of isomer that includes two or more interconvertible compounds resulting from at least one formal migration of a hydrogen atom and at least one change in valency (e.g., a single bond to a double bond, a triple bond to a single bond, or vice versa). "Tautomerization" includes prototropic or proton-shift tautomerization, which is considered a subset of acid-base chemistry. "Prototropic tautomerization" or "proton-shift tautomerization" involves the migration of a proton accompanied by changes in bond order. The exact ratio of the tautomers depends on several factors, including temperature, solvent, and pH. Where tautomerization is possible (e.g., in solution), a chemical equilibrium of tautomers can be reached. Tautomerizations (i.e., the reaction providing a tautomeric pair) can be catalyzed by acid or base, or can occur without the action or presence of an external agent. Exemplary tautomerizations include, but are not limited to, keto-to-enol; amide-to-imide; lactam-to-lactim; enamine-to-imine; and enamine-to-(a different) enamine tautomerizations. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

All chiral, diastereomeric, racemic, and geometric isomeric forms of a structure are intended, unless specific stereochemistry or isomeric form is specifically indicated. All processes used to prepare compounds of the present invention and intermediates made therein are considered to be part of the present invention. All tautomers of shown or described compounds are also considered to be part of the present invention.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes an about 10% change in expression levels, preferably an about 25% change, more preferably an about 40% change, and most preferably an about 50% or greater change in expression levels."

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected. In particular embodiments, the analyte is a PDE3A or SLFN12 polypeptide.

By "disease" is meant any condition or disorder that damages or interferes with the normal function of a cell, tissue, or organ. Examples of diseases include melanoma, adenocarcinoma, lung cancer, cervical cancer, liver cancer and breast cancer.

By "effective amount" is meant the amount of a compound described herein required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount. In one embodiment, the compound is DNMDP, zardaverine, or anagrelide.

The invention provides a number of targets that are useful for the development of highly specific drugs to treat or a disorder characterized by the methods delineated herein. In addition, the methods of the invention provide a facile means to identify therapies that are safe for use in subjects. In addition, the methods of the invention provide a route for analyzing virtually any number of compounds for effects on a disease described herein with high-volume throughput, high sensitivity, and low complexity.

By "fragment" is meant a portion of a polypeptide or nucleic acid molecule. This portion contains, preferably, at least about 10%, about 20%, about 30%, about 40%, about 50%, about 60%, about 70%, about 80%, or about 90% of the entire length of the reference nucleic acid molecule or polypeptide. A fragment may contain about 10, about 20, about 30, about 40, about 50, about 60, about 70, about 80, about 90, about 100, about 200, about 300, about 400, about 500, about 600, about 700, about 800, about 900, or about 1000 nucleotides or amino acids.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "marker" or "biomarker" is meant any protein or polynucleotide having an alteration in expression level or activity (e.g., at the protein or mRNA level) that is associated with a disease or disorder. In particular embodiments, a marker of the invention is PDE3A or SLFN12.

By "modulator" is meant any agent that binds to a polypeptide and alters a biological function or activity of the polypeptide. A modulator includes, without limitation, agents that reduce or eliminate a biological function or activity of a polypeptide (e.g., an "inhibitor"). For example, a modulator may inhibit a catalytic activity of a polypeptide. A modulator includes, without limitation, agents that increase or decrease binding of a polypeptide to another agent. For example, a modulator may promote binding of a polypeptide to another polypeptide. In some embodiments, a modulator of PDE3A polypeptide is DNMDP. In some other embodiments, the modulator of PDE3A polypeptide is anagrelide or zardaverine.

By "reference" is meant a standard or control condition.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1A is a scatterplot of 1924 compounds showing mean survival of TP53 mutant NCI-H1734 cells, which is a non-small cell lung cancer cell line, and TP53 wild-type A549 cells, another lung cancer cell line, after 48 hours of treatment at concentrations of 10 μM. DNMDP is indicated with a large arrowhead. Other compounds that selectively killed NCI-H1734 cells are indicated with a small arrow. Positive control staurosporine is indicated with a long arrow. FIG. 1B is a linear graph showing a panel of cell lines that was treated with the indicated concentrations of DNMDP for 48 hours. FIG. 1C is a linear graph showing the HeLa cell line that was treated with indicated concentrations of the separated enantiomers of DNMDP for 48 hours. The (R)-enantiomer had a 500-fold lower $EC_{50}$ compared to the (S)-enantiomer. FIG. 1D is a structure of (R)-DNMDP.

FIG. 4A are three chromatographs showing Peak 1 (CRO separation); FIG. 4B are three chromatographs showing Peak 2 (CRO separation); FIG. 4C are three chromatographs showing synthesized (R)-DNMDP (5:95 ratio peaks 1:2 by uv).

FIG. 5A is a scatterplot showing correlation between DNMDP sensitivity and expression of 18,988 genes in 766 genomically characterized cell lines. Cell lines were treated for 72 hours with concentrations ranging from 66.4 μM-2 nM in 2-fold step dilutions. The Z-score for Pearson correlation between PDE3A expression and sensitivity to DNMDP is 8.5. FIG. 5B is a scatterplot showing results from cell lines from panel A that were treated with 480 compounds. DNMDP showed the best correlation between PDE3A expression and sensitivity. FIG. 5C is a scatterplot showing published PDE3 inhibitor $IC_{50}$ values and $EC_{50}$ values of HeLa cells treated with indicated compounds up to 10 μM for 48 hours. DNMDP $IC_{50}$ concentration for PDE3A inhibition was determined in FIG. 7B.

FIG. 7A shows PDE3A in vitro inhibition with indicated concentrations of positive control trequinsin ($IC_{50}$ curve was performed by Caliper). FIG. 7B shows PDE3A in vitro inhibition with indicated concentrations of DNMDP ($IC_{50}$ curve was performed by Caliper).

FIG. 8A shows cAMP concentrations that were measured 1 hour after treatment with indicated compounds and concentration in HeLa cells. FIG. 8B shows viability of HeLa cells that were treated with indicated compounds and concentrations for 48 hours.

FIG. 9A is a scatterplot showing viability of HeLa cells that were treated with 1600 bioactive compounds at a concentration of 20 μM in combination with 30 nM (EC70) of DNMDP for 48 hours. The viability was calculated as a percentage of the untreated DMSO control. FIG. 9B is a linear graph showing viability of HeLa cells that were treated with DNMDP in combination with indicated concentrations of non-lethal PDE3 and pan-PDE inhibitors for 48 hours. FIG. 9C shows a SDS-PAGE gel depicting the result of affinity purification performed on 200 μg of HeLa cell lysate using a DNMDP linker-analogue tethered to a solid phase with the same rescue characteristic as non-lethal PDE3 inhibitors. Indicated compounds were co-incubated with the linker-analogue. The affinity purified fraction was run on an SDS-PAGE gel and probed for PDE3A.

FIG. 10A shows the structure of DNMDP-2L. FIG. 10B is a graph showing the viability of HeLa cells that were treated with indicated compounds and concentrations for 48 hours.

FIG. 11A is a Western blot. HeLa cells were infected with Cas9 and indicated guide RNAs (sgRNA) against PDE3A. Western blots were probed for PDE3A at indicated time points. FIG. 11B is a bar graph showing percent rescue of HeLa cells that were infected with indicated sgRNAs for two weeks and treated with 1 μM of 6-(4-(diethylamino)-3-nitrophenyl)-5-methyl-4,5-dihydropyridazin-3(2H)-one (DNMDP) for 48 hours. Percent rescue was normalized to the Cas9-only control. FIG. 11C is a plot showing viability of cells infected with indicated sgRNAs and treated with various concentrations of 6-(4-(diethylamino)-3-nitrophenyl)-5-methyl-4,5-dihydropyridazin-3(2H)-one (DNMDP).

In FIG. 12A HeLa cells were treated with scrambled control siRNA or a combination of four different siRNAs targeting PDE3A. Cells were lysed at indicated time-points and immunoblotted for PDE3A and Actin. FIG. 12B is a linear graph showing viability of HeLa cells that were treated with indicated concentrations of DNMDP analogue 3 for 48 hours.

FIG. 13A shows a schematic overview of the affinity enrichment followed by quantitative proteomics of PDE3A performed in HeLa cells. All cells were treated for four hours prior to lysis with 10 μM of indicated compounds. The presence of all compounds was maintained throughout the experiment including washing steps. FIG. 13B is a scatterplot showing $log_2$ ratios for proteins that were enriched in anti-PDE3A immuno precipitates in the DMSO treated HeLa cells compared to anti-PDE3A immuno precipitates in the presence of blocking peptide specific to the PDE3A antibody; each dot represents a protein. FIG. 13C is a scatterplot showing $Log_2$ ratios of changes of proteins bound to PDE3A in the presence of DNMDP versus trequinsin. Each dot represents the average of two replicates per condition for an individual protein. In all cases, the data plotted passed the Bland-Altman test with 95% confidence interval for reproducibility.

In FIG. 14A protein enrichment was accomplished by immunoprecipitation using anti-PDE3A. In FIG. 14B protein enrichment was accomplished by immunoprecipitation using anti-PDE3A in the presence of DNMDP. In FIG. 14C protein enrichment was accomplished by immunoprecipitation using anti-PDE3A in the presence of trequinsin.

FIG. 15A is a scatterplot showing mRNA robust multichip average (RMA) expression values for PDE3A and SLFN12 from the Cancer Cell Line Encyclopedia (CCLE) database (a detailed genetic characterization of a large panel of human cancer cell lines) with sensitive cell lines indicated (Barretina et al., Nature 483, 603-607, 2012). 21 sensitive cell lines were binned in three groups of 7 based on area under the curve (AUC) rank. FIG. 15B is a bar graph showing results of a Fisher's exact test on DNMDP sensitivity of cell lines with high expression of both SLFN12 and PDE3A (RMA Log 2>5) compared to other cell lines. The top half of the bar on the right indicates melanoma cell lines. FIG. 15C is a scatterplot showing mRNA RPKM+1 expression values for PDE3A and SLFN12 from RNA sequencing data. FIG. 15D is a bar graph showing qPCR expression changes of SLFN12 in HeLa cells transduced with shSLFN12 normalized to GAPDH. FIG. 15E is a plot showing viability of HeLa cells transduced with indicated shRNA reagents and treated with indicated concentrations of DNMDP for 72 hours.

FIG. 16A shows the correlation between DNMDP sensitivity and expression of 18,988 genes in 766 genomically characterized cell lines. Cell lines were treated for 72 hours with concentrations ranging from 66.4 μM-2 nM in 2-fold step dilutions. FIG. 16B is a scatterplot showing a correlation between DNMDP sensitivity and expression of 18,988 genes in 766 genomically characterized cell lines. Expression levels were corrected for PDE3A expression as described earlier (Kim et al., Genetica 131, 151-156, 2007). Cell lines were treated for 72 hours with concentrations ranging from 66.4 μM-2 nM in 2-fold step dilutions.

FIGS. 17A-7B show that DNMDP induces apoptosis in HeLa cells. FIG. 17A is a plot showing viability of HeLa cells treated for 48 hours with indicated concentrations of DNMDP. Caspase-Glo represents Caspase 3/7 activity indicating induction of apoptosis. CellTiter-Glo reflects viability.

FIG. 20 shows that DNMDP and (weakly) anagrelide, but not trequinsin, induced PDE3A and SFLN12 complex formation.

Figure 1A:
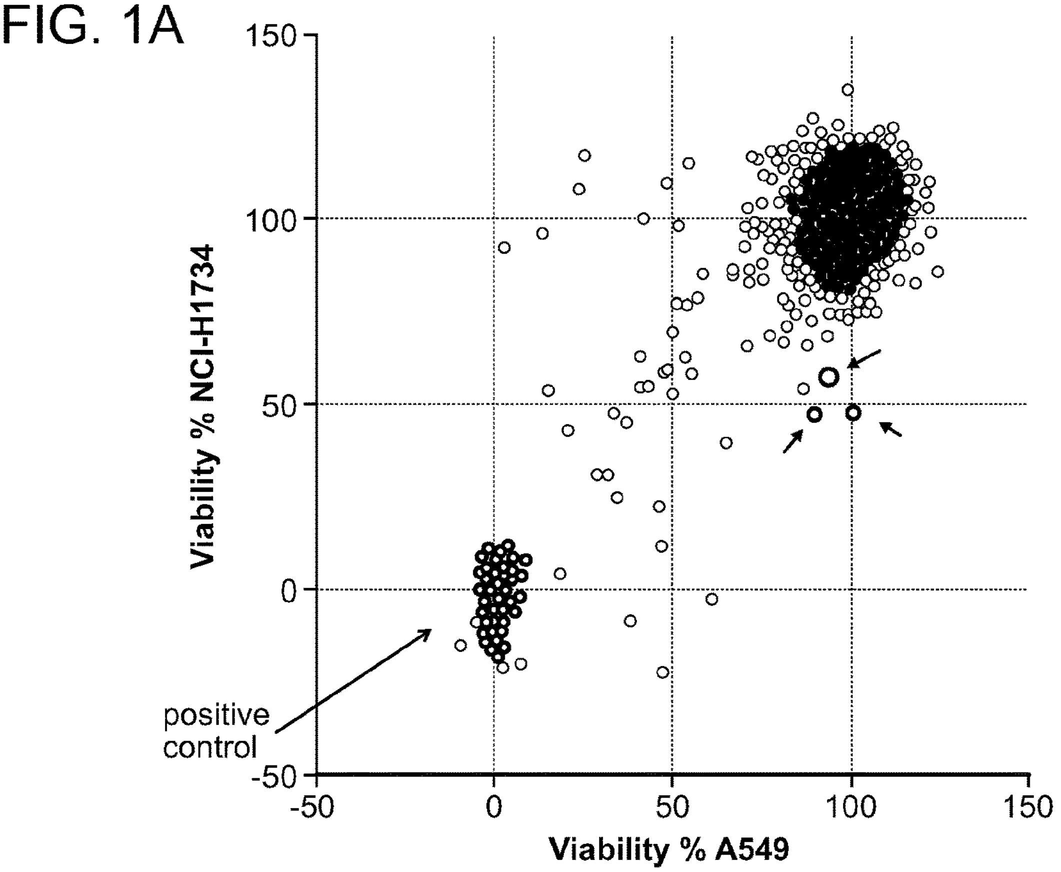
FIGS. 1A-1D show identification and characterization of 6-(4-(diethylamino)-3-nitrophenyl)-5-methyl-4,5-dihydropyridazin-3(2H)-one (DNMDP), a potent and selective cancer cell cytotoxic agent.

Table 1 shows sensitivity data of 766 cancer cell lines treated with DNMDP. Cell lines were treated for 72 hours with concentrations ranging from 66.4 μM-2 nM in 2-fold step dilutions.

Table 2 shows results from panel of 19 phosphodiesterase inhibition reactions performed by Caliper. DNMDP concentration was 100 nM.

Table 3 shows RPKM values of SLFN12 and PDE3A expression in multiple healthy tissue types.

Table 4 showing Leiomyosarcoma sensitivity to DNMDP

Table 5 shows binding of DNMDP to PDE3A(677-1141).

Compositions and articles defined by the invention were isolated or otherwise manufactured in connection with the examples provided below. Other features and advantages of the invention will be apparent from the detailed description, and from the claims.

DETAILED DESCRIPTION

As described below, the present invention features improved methods of identifying patients having cancer (e.g., melanoma, endometrium, lung, hematopoetic/lymphoid, ovarian, cervical, soft-tissue sarcoma, leiomyosarcoma, urinary tract, pancreas, thyroid, kidney, glioblastoma, or breast cancer)) that is sensitive to treatment with a phosphodiesterase 3A (PDE3A) modulator by detecting co-expression of PDE3A and Schlafen 12 (SLFN12) polypeptides or polynucleotides in a cancer cell derived from such patients. The invention is based at least in part on the discovery that sensitivity to phosphodiesterase 3A modulators, such as 6-(4-(diethylamino)-3-nitrophenyl)-5-methyl-4,5-dihydropyridazin-3(2H)-one, or DNMDP, in 766 cancer cell lines correlated with expression of the phosphodiesterase 3A gene, PDE3A. Like DNMDP, a subset of PDE3A inhibitors kill selected cancer cells while others do not; these cell-sparing PDE3A inhibitors instead block DNMDP induced cytotoxicity. Furthermore, PDE3A depletion leads to DNMDP resistance. DNMDP binding to PDE3A promotes an interaction between PDE3A and Sirtuin 7 (SIRT7) and Schlafen 12 (SLFN12), suggesting a neomorphic activity, and SLFN12 and PDE3A co-expression correlated with DNMDP sensitivity. These results indicate that PDE3A modulators are promising cancer therapeutic agents and demonstrate the power of chemogenomics in small-molecule discovery and target-identification.

Accordingly, the invention provides methods of selecting a subject as having a cancer that responds to a PDE3A modulator, where the selection method involves detecting co-expression of PDE3A and Schlafen 12 (SLFN12) polypeptides or polynucleotides, in a cancer cell derived from such subjects.

PDE3A Modulator

The identification of PDE3A modulators was made in connection with a phenotypic screen designed to identify cytotoxic small molecules in a mutant tp53 background. A chemogenomics approach complements target-driven drug development programs, which consists of extensive in vitro and in vivo target validation, and can also be referred to as reverse chemogenomics (Zheng et al., Curr Issues Mol Biol 4, 33-43, 2002). Many U.S. Food and Drug Administration (FDA)-approved targeted therapies have been developed this way, among them small-molecule kinase inhibitors that target oncogenic somatic driver mutations (Moffat et al., Nat Rev Drug Discov 13, 588-602, 2014). However, the discovery and development of targeted therapies is often hampered by limitations in knowledge of the biological function of the target, its mechanism of action, and the available chemical matter to selectively inhibit the target.

Phenotypic screening can discover novel targets for cancer therapy whose specific molecular mechanism is often elucidated by future studies (Swinney et al., Nat Rev Drug Discov 10, 507-519, 2011). In recent years, two classes of anti-cancer drugs found by unbiased phenotypic screening efforts have been approved by the FDA. Lenalidomide and pomalidomide were found to be modulators of an E3-ligase that alter the affinity of its target, leading to degradation of lineage specific transcription factors (Krönke et al., Science 343, 301-305, 2014; Lu et al., Science 343, 305-309, 2014), whereas romidepsin and vorinostat were later identified as histone deacetylase (HDAC) inhibitors (Moffat et al., Nat Rev Drug Discov 13, 588-602, 2014; Nakajima et al., Exp. Cell Res. 241, 126-133, 1998, Marks et al., Nat Biotechnol 25, 84-90, 2007).

Tumor suppressor alterations are suitable targets for phenotypic screening as they are not directly targetable with small molecules, although synthetic lethal approaches such as olaparib treatment of BRCA1/BRCA2 mutant cancers have proven to be effective. According to current knowledge, the tp53 tumor suppressor gene is the most frequently mutated across human cancer, with somatic mutations detected in 36% of 4742 cancers subjected to whole exome sequencing. Despite many attempts, no compounds that selectively kill tp53 mutant cells have been identified.

A phenotypic screen developed to identify small molecules causing synthetic lethality in tp53 mutant cancer cells enabled the serendipitous discovery of a class of cancer-selective cytotoxic agents which act as modulators of phosphodiesterase 3A (PDE3A), as described herein below.

Cyclic nucleotide phosphodiesterases catalyze the hydrolysis of second messenger molecules cyclic adenosine monophosphate (cAMP) and cyclic guanosine monophosphate (cGMP), and are important in many physiological processes. Several phosphodiesterase inhibitors have been approved for clinical treatment, including PDE3 inhibitors milrinone, cilostazol, and levosimendan for cardiovascular indications and inhibition of platelet coagulation, as well as the PDE3 inhibitor anagrelide for thrombocythemia. PDE5 inhibitors, e.g. vardenafil, are used for smooth muscle disorders including erectile dysfunction and pulmonary arterial hypertension, and the PDE4 inhibitor roflumilast reduces exacerbations from chronic obstructive pulmonary disease (COPD).

Phosphodiesterase inhibitors act by direct inhibition of their targets or by allosteric modulation; for example, structural analysis of PDE4 has led to the design of PDE4D and PDE4B allosteric modulators (Burgin et al., Nat Biotechnol 28, 63-70, 2010; Gurney et al., Neurotherapeutics 12, 49-56, 2015). The data provided herein below indicates that the cancer cytotoxic phosphodiesterase modulator DNMDP likely acts through a similar allosteric mechanism.

Accordingly, the invention provides methods for identifying subjects that have a malignancy that is likely to respond to PDE3A modulator treatment based on the level of PDE3A and SLFN12 expression in a subject biological sample comprising a cancer cell. In some embodiments, the PDE3A modulator is DNMDP. In some other embodiments, the PDE3A modulator is anagrelide or zardaverine.

Compound Forms and Salts

The compounds of the present invention include the compounds themselves, as well as their salts and their prodrugs, if applicable. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion. Examples of prodrugs include $C_{1-6}$ alkyl esters of carboxylic acid groups, which, upon administration to a subject, are capable of providing active compounds.

Pharmaceutically acceptable salts of the compounds of the present disclosure include those derived from pharmaceutically acceptable inorganic and organic acids and bases. As used herein, the term "pharmaceutically acceptable salt" refers to a salt formed by the addition of a pharmaceutically acceptable acid or base to a compound disclosed herein. As used herein, the phrase "pharmaceutically acceptable" refers to a substance that is acceptable for use in pharmaceutical applications from a toxicological perspective and does not adversely interact with the active ingredient.

Examples of suitable acid salts include acetate, adipate, alginate, aspartate, benzoate, benzenesulfonate, bisulfate, butyrate, citrate, camphorate, camphorsulfonate, digluconate, dodecylsulfate, ethanesulfonate, formate, fumarate, glucoheptanoate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the present invention and their pharmaceutically acceptable acid addition salts. Salts derived from appropriate bases include alkali metal (e.g., sodium), alkaline earth metal (e.g., magnesium), ammonium and N-$(alkyl)_4^+$ salts. The present invention also envisions the quaternization of any basic nitrogen-containing groups of the compounds disclosed herein. Water or oil-soluble or dispersible products may be obtained by such quaternization. Salt forms of the compounds of any of the formulae herein can be amino acid salts of carboxyl groups (e.g., L-arginine, -lysine, -histidine salts).

Lists of suitable salts are found in Remington's Pharmaceutical Sciences, 17th ed., Mack Publishing Company, Easton, Pa., 1985, p. 1418; Journal of Pharmaceutical Science, 66, 2 (1977); and "Pharmaceutical Salts: Properties, Selection, and Use A Handbook; Wermuth, C. G. and Stahl, P. H. (eds.) Verlag Helvetica Chimica Acta, Zurich, 2002 [ISBN 3-906390-26-8] each of which is incorporated herein by reference in their entireties.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity. Additional examples include peptidyl derivatives of a compound of the present invention.

The present invention also includes various hydrate and solvate forms of the compounds.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

Diagnostics

The present invention features diagnostic assays for the characterization of cancer. In one embodiment, levels of PDE3A and/or Schlafen 12 (SLFN12) polynucleotides or polypeptides are measured in a subject sample and used as an indicator of cancer that is responsive to treatment with a PDE3A modulator. Levels of PDE3A and/or Schlafen 12 polynucleotides may be measured by standard methods, such as quantitative PCR, Northern Blot, microarray, mass spectrometry, and in situ hybridization. Standard methods may be used to measure levels of PDE3A and/or Schlafen 12, polypeptides in a biological sample derived from a tumor. Such methods include immunoassay, ELISA, western blotting using an antibody that binds PDE3A and/or Schlafen 12 and radioimmunoassay. Elevated levels of PDE3A and Schlafen 12 polynucleotides or polypeptides relative to a reference are considered a positive indicator of cancer that is responsive to treatment with a PDE3A modulator.

Types of Biological Samples

In characterizing the responsiveness of a malignancy in a subject to PDE3A modulator treatment, the level of PDE3A and/or SLFN12 expression is measured in different types of biologic samples. In one embodiment, the biologic sample is a tumor sample.

PDE3A and/or SLFN12 expression is higher in a sample obtained from a subject that is responsive to PDE3A modulator treatment than the level of expression in a non-responsive subject. In another embodiment, PDE3A and/or SLFN12 is at least about 5, 10, 20, or 30-fold higher in a subject with a malignancy than in a healthy control. Fold change values are determined using any method known in the art. In one embodiment, change is determined by calculating the difference in expression of PDE3A and/or SLFN12 in a cancer cell vs the level present in a non-responsive cancer cell or the level present in a corresponding healthy control cell.

Selection of a Treatment Method

As reported herein below, subjects suffering from a malignancy may be tested for PDE3A and/or SLFN12 expression in the course of selecting a treatment method. Patients characterized as having increased PDE3A and/or SLFN12 relative to a reference level are identified as responsive to PDE3A modulator treatment.

Kits

The invention provides kits for characterizing the responsiveness or resistance of a subject to PDE3A modulator treatment.

Also provided herein are kits that can include a therapeutic composition containing an effective amount of a PDE3A modulator in, e.g., unit dosage form.

In one embodiment, a diagnostic kit of the invention provides a reagent for measuring relative expression of PDE3A and SLFN12. Such reagents include capture molecules (e.g., antibodies that recognize PDE3A and SLFN12 polypeptides or nucleic acid probes that hybridize with PDE3A and SLFN12 polynucleotides).

In some embodiments, the kit comprises a sterile container which includes a therapeutic or diagnostic composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

In one embodiment, a kit of the invention comprises reagents for measuring PDE3A and/or SLFN12 levels. If desired, the kit further comprises instructions for measuring PDE3A and/or SLFN12 and/or instructions for administering the PDE3A modulator to a subject having a malignancy, e.g., a malignancy selected as responsive to PDE3A modulator treatment. In particular embodiments, the instructions include at least one of the following: description of the therapeutic agent; dosage schedule and administration for treatment or prevention of malignancy or symptoms thereof; precautions; warnings; indications; counter-indications; over dosage information; adverse reactions; animal pharmacology; clinical studies; and/or references. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of the invention.

EXAMPLES

Example 1. Identification of a Cell-Selective Cytotoxic Small Molecule

To identify anti-cancer compounds with cell-selective cytotoxic activity, an unbiased chemical screen was performed in two lung adenocarcinoma cell lines, A549 and NCI-H1734, both of which harbor oncogenic KRAS mutations and truncating STK11 mutations, and which were TP53 wild type and mutant (R273L), respectively. 1,924 compounds were screened from the Molecular Libraries Small-Molecule Repository validation set in the A549 and NCI-H1734 cell lines at a single concentration of 10 μM in 384-well format in duplicate. As a proxy for cellular viability, ATP content was measured after 48 hours of compound treatment.

Figure 2:
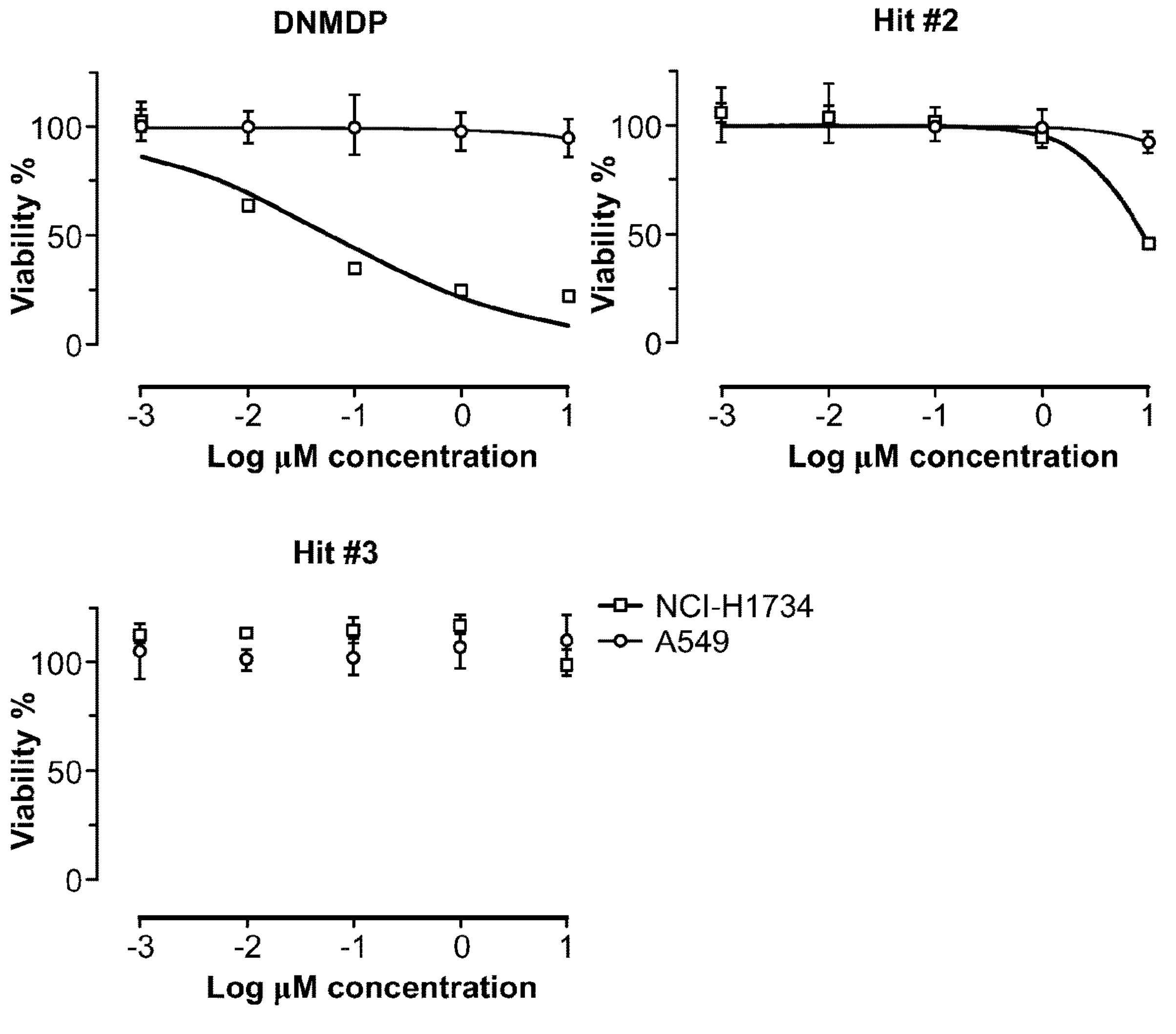
FIG. 2 shows that DNMDP selectively killed NCI-H1734 and did not affect cell viability in A549. NCI-H1734 and A549 cell lines were treated with indicated compounds and concentrations for 48 hours.

Three compounds showed a selective reduction in cell viability for the NCI-H1734 cell line compared to the A549 cell line, with an approximately 50% reduction in the NCI-H1734 cell line, which is >4 median absolute deviations from the median in the negative direction, compared to a minimal change of <1 median absolute deviations from the median in the A549 cell line (FIG. 1A). Retesting the three compounds in a dose-response analysis validated that one compound, 6-(4-(diethylamino)-3-nitrophenyl)-5-methyl-4,5-dihydropyridazin-3(2H)-one, or DNMDP, was specifically toxic to the NCI-H1734 cell line (FIG. 2).

Figure 1B:
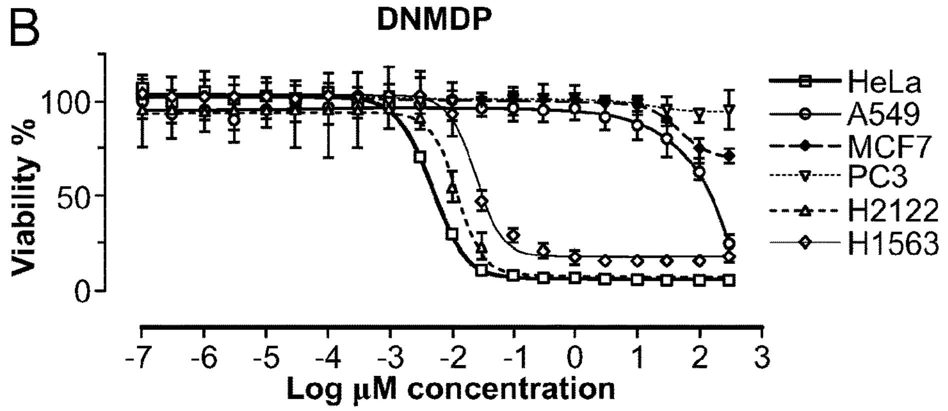
Figure 1C:
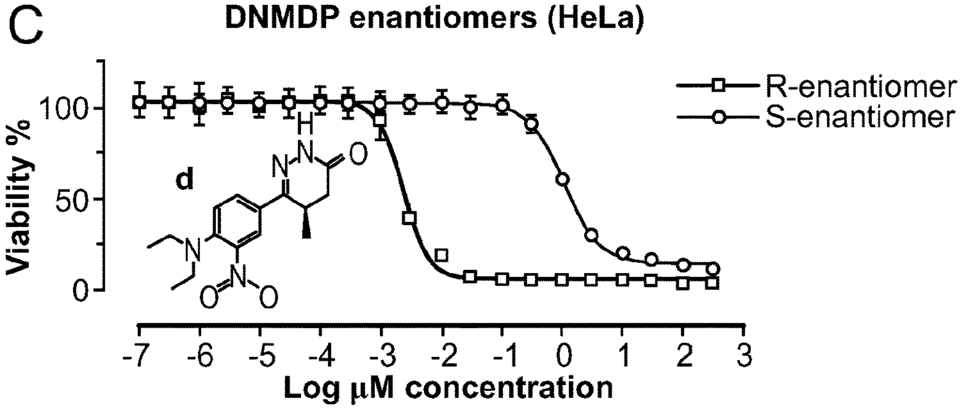
Figure 1D:
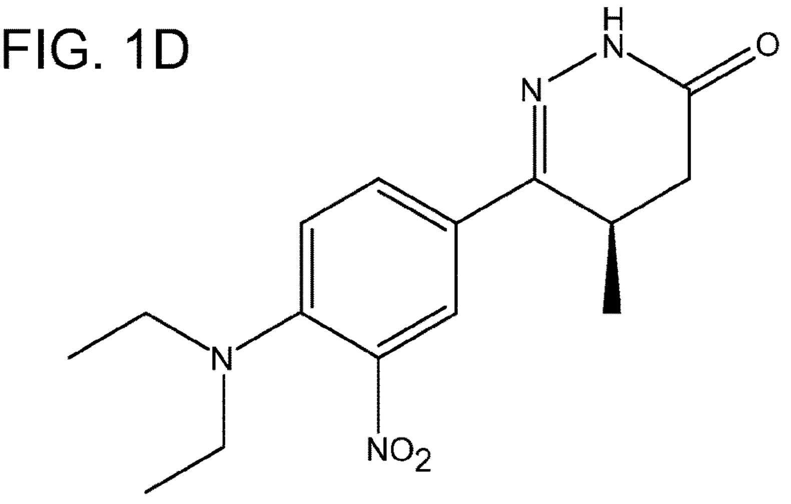
Figure 17A:
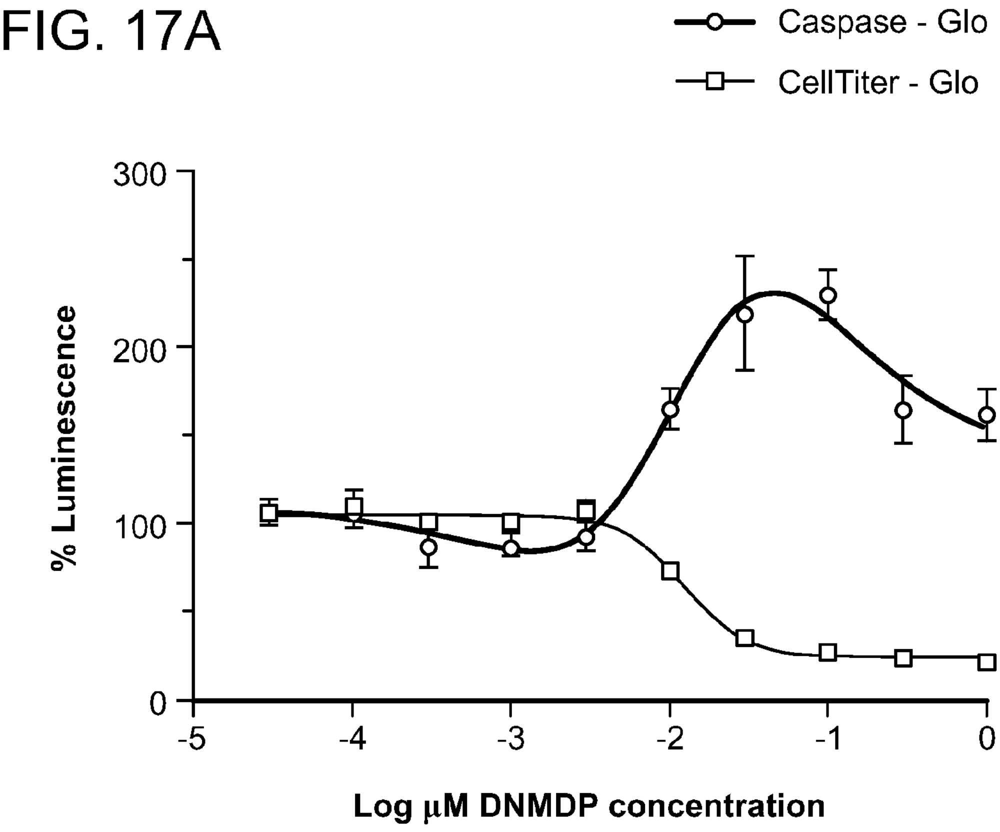
Figure 17B:
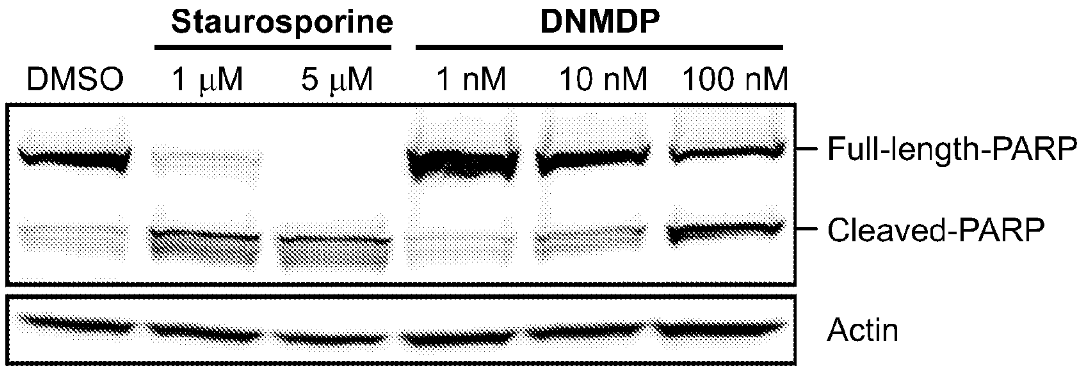
FIG. 17B is an immunoblot. HeLa cells were treated for 36 hours with indicated compounds and concentrations. HeLa cells were harvested and immunoblotted for PARP-cleavage products, indicative of apoptosis.

Testing of additional cell lines with DNMDP showed clear cell-selective cytotoxicity, with an $EC_{50}$ between 10 and 100 nM for two additional lung adenocarcinoma cell lines, NCI-H1563 and NCI-H2122, and for HeLa cervical carcinoma cells, but an $EC_{50}$ greater than 1 μM for A549, MCF7, and PC3 cells (FIG. 1B; FIG. 1C). Caspase activity was detected by a caspase-sensitive luciferase assay and by poly ADP ribose polymerase (PARP) cleavage in HeLa cells upon DNMDP treatment, indicating that sensitive cells undergo apoptosis after DNMDP exposure (FIGS. 17A-17B). To characterize cellular sensitivity to DNMDP further, 766 genomically characterized cancer cell lines were screened for DMNDP sensitivity at concentrations ranging from 66.4 μM to 2 nM in 2-fold dilution steps for 72 hours. From these cell lines, 22 cell lines were categorized as sensitive with a robust Z-score lower than −4, which represented multiple lineages including multiple melanoma cell lines, amongst others (Table 1).

Figure 3:
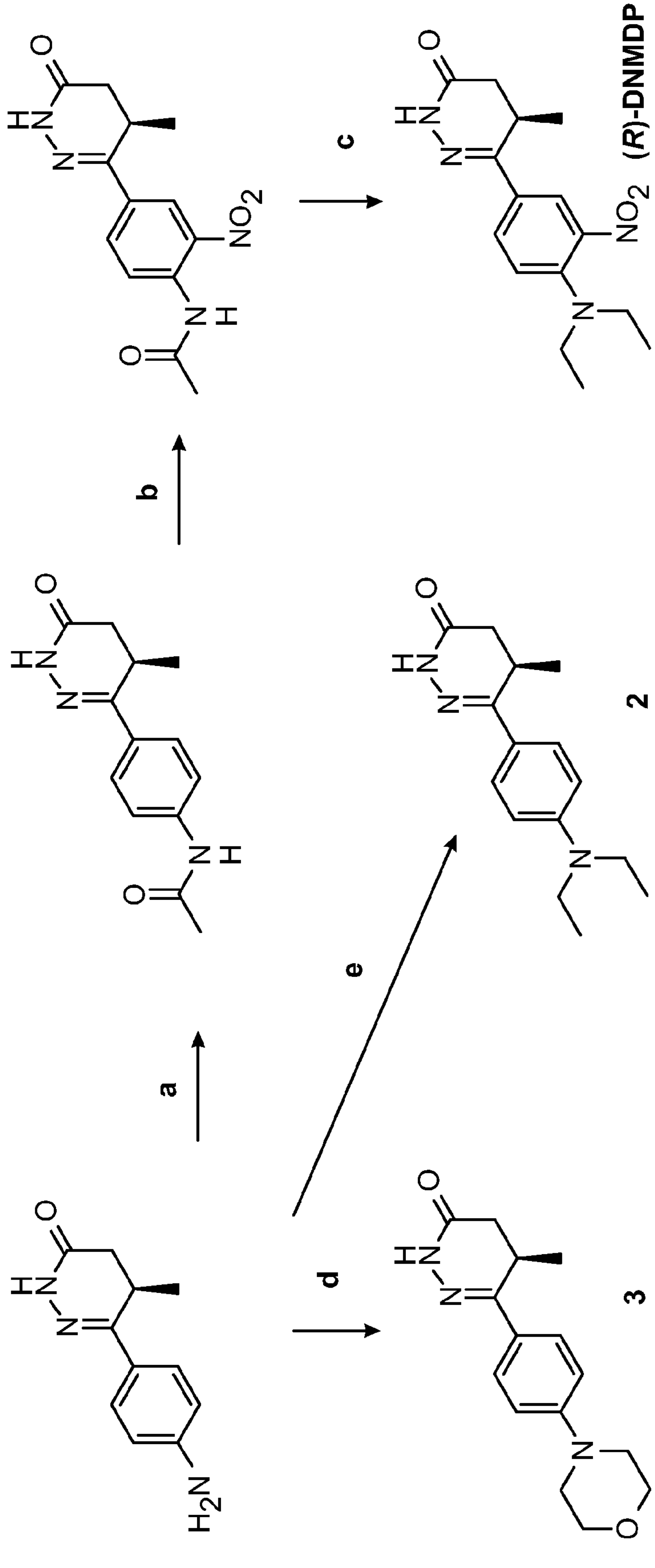
FIG. 3 shows the synthesis scheme of (R)-6-(4-(diethylamino)-3-nitrophenyl)-5-methyl-4,5-dihydropyridazin-3(2H)-one (R)-DNMDP) and analogues. Reaction conditions are as follows: (a) $Ac_2O$, (91%); (b) 90% $HNO_3$, $H_2SO_4$, (19%); (c) NaOH, $MeOH/H_2O$, (100%), then $CH_3CHO$, $NaBH(OAc)_3$, (7%); (d) $(BrCH_2CH_2)_2O$, $K_2CO_3$, DMF, (46%); (e) $CH_3CHO$, $NaBH_3CN$, MeOH, (82%).
Figure 4A:
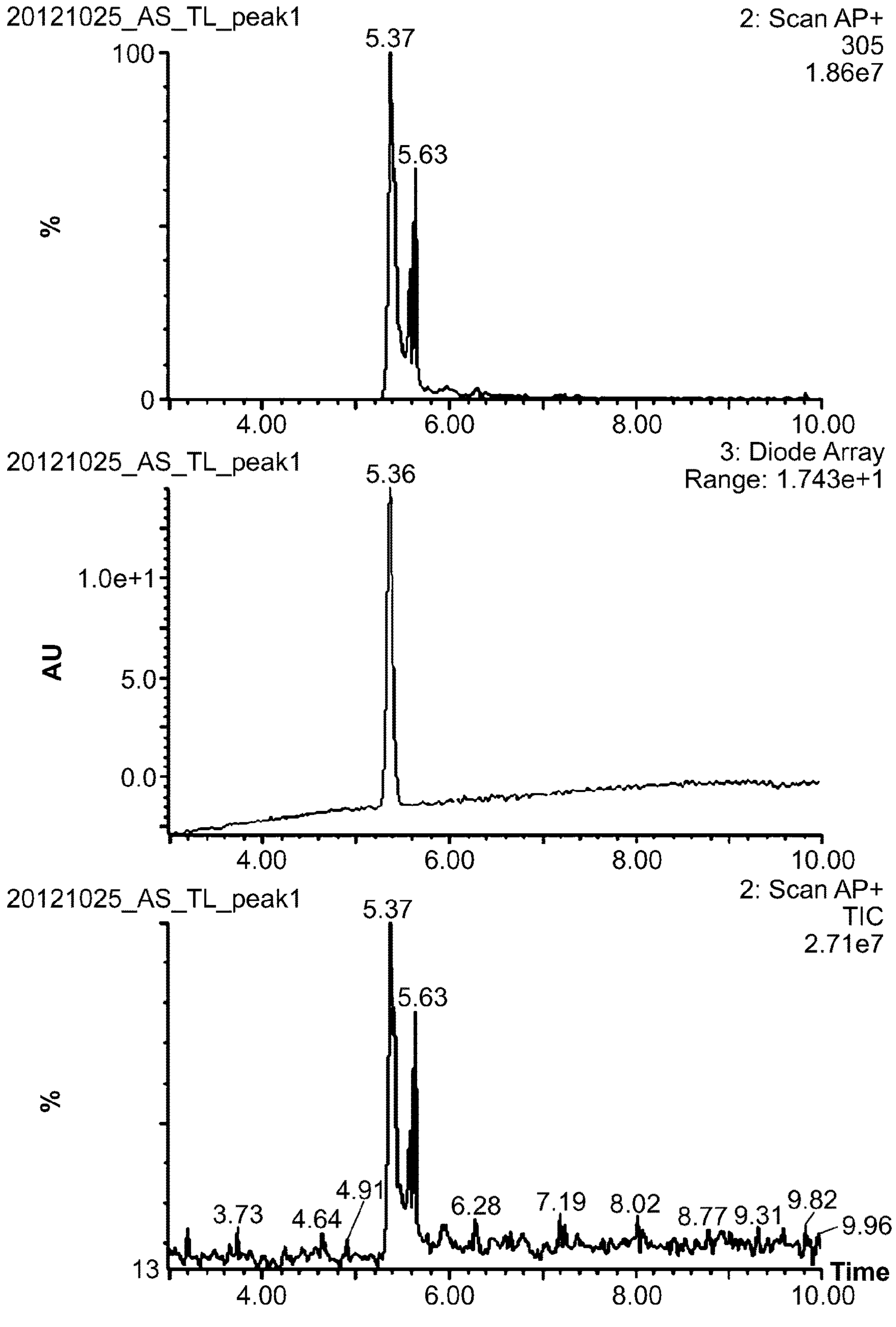
FIGS. 4A-4C show super-critical fluid (SCF) chromatographs of 6-(4-(diethylamino)-3-nitrophenyl)-5-methyl-4,5-dihydropyridazin-3(2H)-one (DNMDP) (top to bottom: ES+, diode array, ES-traces).
Figure 4B:
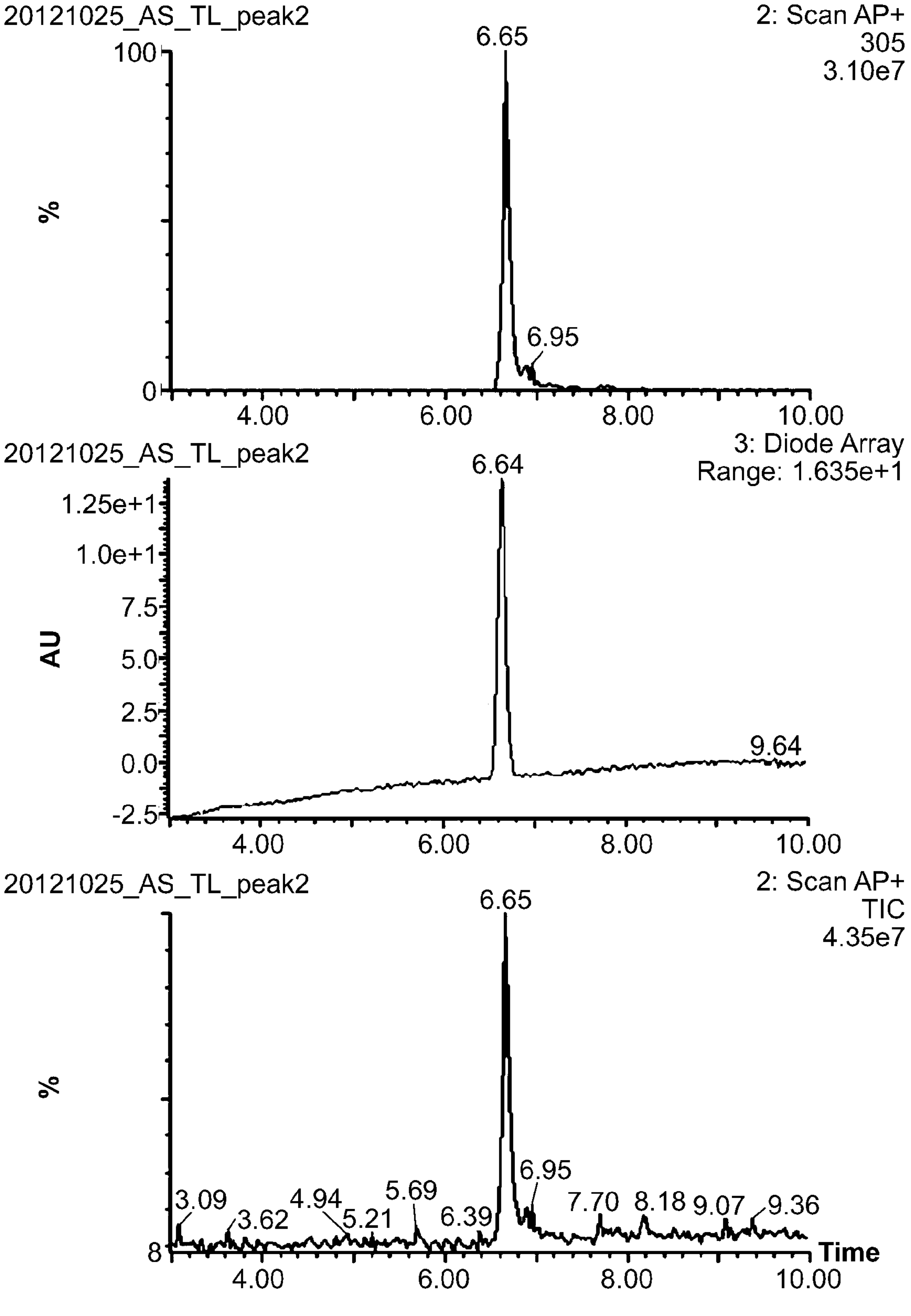
Figure 4C:
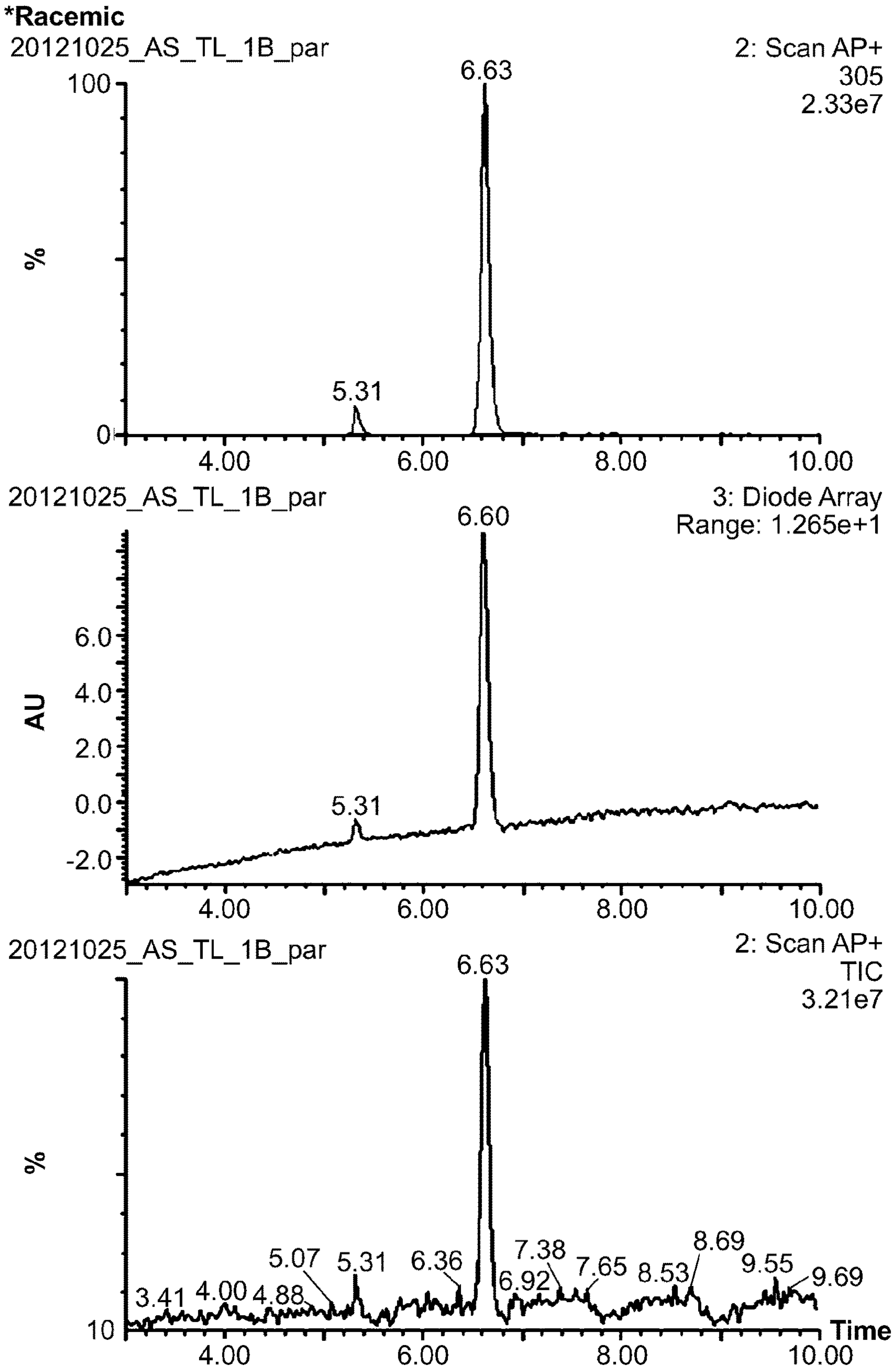

Next, the DNMDP enantiomers were separated by chiral super-critical fluid (SCF) chromatography. One enantiomer was 500-fold more potent in HeLa cells than the other (FIGS. 1C and D). The (R)-enantiomer was synthesized from commercially available starting materials (FIG. 3). This synthesized enantiomer had similar activity to the more potent separated material and was identical by chiral SCF chromatography, confirming stereochemistry of the active enantiomer (FIGS. 4A-4C). Two (R)-des-nitro analogues of DNMDP were synthesized, both of which tested similarly to (R)-DNMDP (FIG. 3). FIGS. 4A-4C show super-critical fluid (SCF) chromatographs of 6-(4-(diethylamino)-3-nitrophenyl)-5-methyl-4,5-dihydropyridazin-3(2H)-one (DNMDP) (top to bottom: ES+, diode array, ES-traces). FIG. 4A shows Peak 1 (CRO separation); FIG. 4B shows Peak 2 (CRO separation); and FIG. 4C shows synthesized (R)-DNMDP (5:95 ratio peaks 1:2 by uv).

TABLE 1

Sensitivity data of 766 cancer cell lines treated with DNMDP

| Cell line | Lineage | DNMDP AUC | Robust Z-score |
|---|---|---|---|
| COV318 | OVARY | 0.095838 | −6.863450362 |
| IGR37 | SKIN | 0.41146 | −6.532158389 |
| JHUEM1 | ENDOMETRIUM | 0.53468 | −6.402820773 |
| HEL | HAEMATOPOIETIC AND LYMPHOID TISSUE | 0.57955 | −6.355723071 |
| CORL51 | LUNG | 0.59436 | −6.340177786 |
| HEL9217 | HAEMATOPOIETIC AND LYMPHOID TISSUE | 0.75005 | −6.176758102 |
| NCIH1563 | LUNG | 1.0887 | −5.821294837 |
| SKMEL3 | SKIN | 1.2215 | −5.681901594 |
| NCIH2122 | LUNG | 1.3105 | −5.58848293 |
| RVH421 | SKIN | 1.4556 | −5.436179018 |
| HUT78 | HAEMATOPOIETIC AND LYMPHOID TISSUE | 1.5307 | −5.35735046 |
| DKMG | CENTRAL NERVOUS SYSTEM | 1.7217 | −5.156867709 |
| GB1 | CENTRAL NERVOUS SYSTEM | 1.8269 | −5.046444748 |
| G292CLONEA141B1 | BONE | 1.9664 | −4.900018865 |
| HMCB | SKIN | 1.9762 | −4.889732315 |
| A2058 | SKIN | 2.0833 | −4.777315024 |
| NCIH1734 | LUNG | 2.2179 | −4.636032415 |
| NCIH196 | LUNG | 2.5263 | −4.312320999 |
| LI7 | LIVER | 2.5414 | −4.296471315 |
| JHOM1 | OVARY | 2.7006 | −4.129367368 |
| COLO741 | SKIN | 2.7231 | −4.10575029 |
| HS578T | BREAST | 2.8012 | −4.023772788 |
| K029AX | SKIN | 2.9362 | −3.88207032 |
| MONOMAC1 | HAEMATOPOIETIC AND LYMPHOID TISSUE | 2.9692 | −3.847431939 |
| HT1197 | URINARY TRACT | 3.0929 | −3.717590492 |
| NCIH520 | LUNG | 3.1351 | −3.67329535 |
| CAL78 | BONE | 3.1711 | −3.635508025 |
| NCIH647 | LUNG | 3.2187 | −3.585544785 |
| CGTHW1 | THYROID | 3.4296 | −3.36417404 |
| NCIH1666 | LUNG | 3.6097 | −3.175132451 |
| L33 | PANCREAS | 3.625 | −3.159072838 |
| UACC62 | SKIN | 3.9116 | −2.858243747 |
| CAS1 | CENTRAL NERVOUS SYSTEM | 3.9993 | −2.766189625 |
| CAL51 | BREAST | 4.0017 | −2.76367047 |
| OSRC2 | KIDNEY | 4.326 | −2.423269652 |
| X8505C | THYROID | 4.3418 | −2.406685215 |
| SH4 | SKIN | 4.3672 | −2.380024158 |
| NCIH1395 | LUNG | 4.4473 | −2.29594736 |
| SNU503 | LARGE INTESTINE | 4.5692 | −2.16799528 |
| HS729 | SOFT TISSUE | 4.6518 | −2.081294362 |
| SW579 | THYROID | 4.697 | −2.033850277 |
| YH13 | CENTRAL NERVOUS SYSTEM | 4.7007 | −2.029966579 |
| DBTRG05MG | CENTRAL NERVOUS SYSTEM | 4.7415 | −1.987140944 |
| SEM | HAEMATOPOIETIC AND LYMPHOID TISSUE | 4.7433 | −1.985251578 |

TABLE 1-continued

| Cell line | Lineage | DNMDP AUC | Robust Z-score |
|---|---|---|---|
| HS852T | SKIN | 4.7511 | −1.977064324 |
| SNU449 | LIVER | 4.752 | −1.976119641 |
| NCIH2286 | LUNG | 4.7782 | −1.948618866 |
| JHOS2 | OVARY | 4.8254 | −1.899075485 |
| BICR31 | UPPER AERODIGESTIVE TRACT | 4.8356 | −1.888369076 |
| IGR1 | SKIN | 4.8613 | −1.861393125 |
| JHUEM3 | ENDOMETRIUM | 4.93 | −1.789282313 |
| SNU387 | LIVER | 4.9639 | −1.753699249 |
| UMUC1 | URINARY TRACT | 4.9933 | −1.7228396 |
| X8305C | THYROID | 5.0004 | −1.7153871 |
| NCIH1915 | LUNG | 5.0031 | −1.712553051 |
| P31FUJ | HAEMATOPOIETIC AND LYMPHOID TISSUE | 5.0106 | −1.704680691 |
| COLO678 | LARGE INTESTINE | 5.0245 | −1.690090585 |
| EOL1 | HAEMATOPOIETIC AND LYMPHOID TISSUE | 5.0478 | −1.665633789 |
| KNS42 | CENTRAL NERVOUS SYSTEM | 5.0791 | −1.632779809 |
| SW1783 | CENTRAL NERVOUS SYSTEM | 5.1161 | −1.593942837 |
| HS940T | SKIN | 5.1573 | −1.550697343 |
| SNU685 | ENDOMETRIUM | 5.206 | −1.499579489 |
| BCPAP | THYROID | 5.2336 | −1.470609207 |
| COLO829 | SKIN | 5.2432 | −1.460532587 |
| DM3 | PLEURA | 5.2635 | −1.439224734 |
| OCUM1 | STOMACH | 5.2843 | −1.417392058 |
| M059K | CENTRAL NERVOUS SYSTEM | 5.3059 | −1.394719663 |
| MG63 | BONE | 5.3943 | −1.301930788 |
| NCIH2172 | LUNG | 5.4245 | −1.270231421 |
| CAOV3 | OVARY | 5.4646 | −1.228140539 |
| PEER | HAEMATOPOIETIC AND LYMPHOID TISSUE | 5.4754 | −1.216804342 |
| HS839T | SKIN | 5.5232 | −1.166631172 |
| CORL105 | LUNG | 5.5442 | −1.144588566 |
| SNU5 | STOMACH | 5.5498 | −1.138710537 |
| MFE296 | ENDOMETRIUM | 5.5618 | −1.126114762 |
| NCIH854 | LUNG | 5.576 | −1.111209762 |
| NCIH146 | LUNG | 5.5773 | −1.10984522 |
| NCIH2081 | LUNG | 5.5811 | −1.105856558 |
| COV644 | OVARY | 5.5849 | −1.101867896 |
| VCAP | PROSTATE | 5.5863 | −1.100398388 |
| BICR18 | UPPER AERODIGESTIVE TRACT | 5.6 | −1.086018212 |
| RH18 | SOFT TISSUE | 5.6283 | −1.056313176 |
| KPNYN | AUTONOMIC GANGLIA | 5.6717 | −1.010758457 |
| KPNSI9S | AUTONOMIC GANGLIA | 5.6827 | −0.99921233 |
| SKCO1 | LARGE INTESTINE | 5.688 | −0.993649196 |
| MV411 | HAEMATOPOIETIC AND LYMPHOID TISSUE | 5.6905 | −0.991025076 |
| COV362 | OVARY | 5.6913 | −0.990185358 |
| NCO2 | HAEMATOPOIETIC AND LYMPHOID TISSUE | 5.7088 | −0.971816519 |
| JHH4 | LIVER | 5.71 | −0.970556942 |
| NCIH2141 | LUNG | 5.7218 | −0.958171096 |
| LXF289 | LUNG | 5.734 | −0.945365392 |
| MEWO | SKIN | 5.738 | −0.9411668 |
| TE125T | SOFT TISSUE | 5.744 | −0.934868913 |
| SNU869 | BILIARY TRACT | 5.7543 | −0.924057539 |
| LNCAPCLONEFGC | PROSTATE | 5.7557 | −0.922588032 |
| NCIH2009 | LUNG | 5.7594 | −0.918704335 |
| SKNBE2 | AUTONOMIC GANGLIA | 5.7717 | −0.905793666 |
| IALM | LUNG | 5.775 | −0.902329827 |
| DU145 | PROSTATE | 5.7825 | −0.894457468 |
| HCC1419 | BREAST | 5.7835 | −0.89340782 |
| NALM6 | HAEMATOPOIETIC AND LYMPHOID TISSUE | 5.7872 | −0.889524123 |
| PECAPJ15 | UPPER AERODIGESTIVE TRACT | 5.789 | −0.887634757 |
| LU99 | LUNG | 5.8016 | −0.874409193 |
| LAMA84 | HAEMATOPOIETIC AND LYMPHOID TISSUE | 5.8201 | −0.854990707 |

Sensitivity data of 766 cancer cell lines treated with DNMDP

TABLE 1-continued

Sensitivity data of 766 cancer cell lines treated with DNMDP

| Cell line | Lineage | DNMDP AUC | Robust Z-score |
|---|---|---|---|
| ONCODG1 | OVARY | 5.8296 | −0.845019051 |
| HS888T | BONE | 5.8353 | −0.839036058 |
| SKNSH | AUTONOMIC GANGLIA | 5.8424 | −0.831583558 |
| TUHR14TKB | KIDNEY | 5.8451 | −0.828749509 |
| PF382 | HAEMATOPOIETIC AND LYMPHOID TISSUE | 5.8519 | −0.821611903 |
| ALLSIL | HAEMATOPOIETIC AND LYMPHOID TISSUE | 5.8724 | −0.800094121 |
| KMS34 | HAEMATOPOIETIC AND LYMPHOID TISSUE | 5.8799 | −0.792221762 |
| BICR6 | UPPER AERODIGESTIVE TRACT | 5.8837 | −0.788233099 |
| GRANTA519 | HAEMATOPOIETIC AND LYMPHOID TISSUE | 5.8937 | −0.77773662 |
| OCIAML2 | HAEMATOPOIETIC AND LYMPHOID TISSUE | 5.8945 | −0.776896902 |
| SUIT2 | PANCREAS | 5.8956 | −0.775742289 |
| BT549 | BREAST | 5.9226 | −0.747401796 |
| KMS28BM | HAEMATOPOIETIC AND LYMPHOID TISSUE | 5.9369 | −0.732391831 |
| HCC1428 | BREAST | 5.9402 | −0.728927992 |
| HCC1500 | BREAST | 5.9451 | −0.723784718 |
| A549 | LUNG | 5.9509 | −0.71769676 |
| KCL22 | HAEMATOPOIETIC AND LYMPHOID TISSUE | 5.9598 | −0.708354893 |
| COLO679 | SKIN | 5.9634 | −0.704576161 |
| SKMEL5 | SKIN | 5.9639 | −0.704051337 |
| HCC1395 | BREAST | 5.9716 | −0.695969048 |
| NCIH1435 | LUNG | 5.9756 | −0.691770456 |
| LOUNH91 | LUNG | 5.9793 | −0.687886759 |
| RPMI8402 | HAEMATOPOIETIC AND LYMPHOID TISSUE | 5.9827 | −0.684317956 |
| COLO668 | LUNG | 5.9969 | −0.669412956 |
| SKLU1 | LUNG | 6.0109 | −0.654717885 |
| KMS12BM | HAEMATOPOIETIC AND LYMPHOID TISSUE | 6.0135 | −0.6519888 |
| SNU1272 | KIDNEY | 6.0226 | −0.642437004 |
| MOLM6 | HAEMATOPOIETIC AND LYMPHOID TISSUE | 6.0447 | −0.619239786 |
| EPLC272H | LUNG | 6.0469 | −0.61693056 |
| SCC4 | UPPER AERODIGESTIVE TRACT | 6.0502 | −0.613466722 |
| LMSU | STOMACH | 6.0528 | −0.610737638 |
| KMS20 | HAEMATOPOIETIC AND LYMPHOID TISSUE | 6.0542 | −0.60926813 |
| G402 | SOFT TISSUE | 6.0606 | −0.602550384 |
| KYSE410 | OESOPHAGUS | 6.0741 | −0.588380137 |
| L540 | HAEMATOPOIETIC AND LYMPHOID TISSUE | 6.0807 | −0.581452461 |
| MOLT13 | HAEMATOPOIETIC AND LYMPHOID TISSUE | 6.084 | −0.577988623 |
| L1236 | HAEMATOPOIETIC AND LYMPHOID TISSUE | 6.0853 | −0.57662408 |
| LP1 | HAEMATOPOIETIC AND LYMPHOID TISSUE | 6.1029 | −0.558150277 |
| SNU620 | STOMACH | 6.1039 | −0.557100629 |
| MALME3M | SKIN | 6.112 | −0.548598481 |
| GSU | STOMACH | 6.1172 | −0.543140312 |
| MCF7 | BREAST | 6.1256 | −0.53432327 |
| COLO800 | SKIN | 6.1272 | −0.532643833 |
| MKN7 | STOMACH | 6.1453 | −0.513645206 |
| SNU119 | OVARY | 6.1473 | −0.51154591 |
| U118MG | CENTRAL NERVOUS SYSTEM | 6.1481 | −0.510706192 |
| OCILY19 | HAEMATOPOIETIC AND LYMPHOID TISSUE | 6.1512 | −0.507452283 |
| RKN | SOFT TISSUE | 6.1579 | −0.500419642 |
| DV90 | LUNG | 6.1676 | −0.490238057 |
| NCIH1355 | LUNG | 6.171 | −0.486669254 |
| KMM1 | HAEMATOPOIETIC AND LYMPHOID TISSUE | 6.1723 | −0.485304712 |
| NCIH1184 | LUNG | 6.1776 | −0.479741578 |
| U937 | HAEMATOPOIETIC AND LYMPHOID TISSUE | 6.1777 | −0.479636613 |
| EJM | HAEMATOPOIETIC AND LYMPHOID TISSUE | 6.1782 | −0.479111789 |

TABLE 1-continued

Sensitivity data of 766 cancer cell lines treated with DNMDP

| Cell line | Lineage | DNMDP AUC | Robust Z-score |
|---|---|---|---|
| C32 | SKIN | 6.1786 | −0.47869193 |
| NCIH23 | LUNG | 6.1854 | −0.471554324 |
| RERFLCAD1 | LUNG | 6.1862 | −0.470714606 |
| T3M10 | LUNG | 6.1867 | −0.470189782 |
| U266B1 | HAEMATOPOIETIC AND LYMPHOID TISSUE | 6.1906 | −0.466096155 |
| CAL54 | KIDNEY | 6.1949 | −0.461582669 |
| DND41 | HAEMATOPOIETIC AND LYMPHOID TISSUE | 6.1979 | −0.458433726 |
| PC14 | LUNG | 6.2003 | −0.455914571 |
| KMS11 | HAEMATOPOIETIC AND LYMPHOID TISSUE | 6.2008 | −0.455389747 |
| DMS53 | LUNG | 6.2061 | −0.449826613 |
| SNU1214 | UPPER AERODIGESTIVE TRACT | 6.2071 | −0.448776965 |
| GOS3 | CENTRAL NERVOUS SYSTEM | 6.2076 | −0.448252141 |
| TE8 | OESOPHAGUS | 6.2119 | −0.443738655 |
| ECGI10 | OESOPHAGUS | 6.2151 | −0.440379781 |
| KO52 | HAEMATOPOIETIC AND LYMPHOID TISSUE | 6.2174 | −0.437965591 |
| NCIH1793 | LUNG | 6.2189 | −0.436391119 |
| NB4 | HAEMATOPOIETIC AND LYMPHOID TISSUE | 6.219 | −0.436286155 |
| NCIH1105 | LUNG | 6.2191 | −0.43618119 |
| OCILY10 | HAEMATOPOIETIC AND LYMPHOID TISSUE | 6.222 | −0.433137211 |
| NCIH69 | LUNG | 6.2243 | −0.430723021 |
| A673 | BONE | 6.2304 | −0.424320168 |
| HCC4006 | LUNG | 6.2335 | −0.42106626 |
| SCC9 | UPPER AERODIGESTIVE TRACT | 6.2351 | −0.419386823 |
| OAW28 | OVARY | 6.2381 | −0.416237879 |
| BXPC3 | PANCREAS | 6.2387 | −0.415608091 |
| ISTMES1 | PLEURA | 6.2389 | −0.415398161 |
| SKMM2 | HAEMATOPOIETIC AND LYMPHOID TISSUE | 6.2396 | −0.414663408 |
| NCIN87 | STOMACH | 6.24 | −0.414243548 |
| T98G | CENTRAL NERVOUS SYSTEM | 6.2412 | −0.412983971 |
| GP2D | LARGE INTESTINE | 6.2536 | −0.399968337 |
| FTC238 | THYROID | 6.2564 | −0.397029323 |
| KMS27 | HAEMATOPOIETIC AND LYMPHOID TISSUE | 6.2607 | −0.392515837 |
| SNU201 | CENTRAL NERVOUS SYSTEM | 6.2618 | −0.391361224 |
| BC3C | URINARY TRACT | 6.266 | −0.386952703 |
| RS411 | HAEMATOPOIETIC AND LYMPHOID TISSUE | 6.2689 | −0.383908724 |
| TALL1 | HAEMATOPOIETIC AND LYMPHOID TISSUE | 6.2742 | −0.37834559 |
| RT4 | URINARY TRACT | 6.2742 | −0.37834559 |
| SKOV3 | OVARY | 6.2773 | −0.375091681 |
| RERFLCAD2 | LUNG | 6.2783 | −0.374042033 |
| KHM1B | HAEMATOPOIETIC AND LYMPHOID TISSUE | 6.2859 | −0.366064709 |
| KASUMI2 | HAEMATOPOIETIC AND LYMPHOID TISSUE | 6.2904 | −0.361341294 |
| MOLT16 | HAEMATOPOIETIC AND LYMPHOID TISSUE | 6.2966 | −0.354833477 |
| NUDUL1 | HAEMATOPOIETIC AND LYMPHOID TISSUE | 6.2966 | −0.354833477 |
| KMS18 | HAEMATOPOIETIC AND LYMPHOID TISSUE | 6.2973 | −0.354098723 |
| MDAMB175VII | BREAST | 6.2981 | −0.353259005 |
| RMGI | OVARY | 6.3019 | −0.349270343 |
| KIJK | HAEMATOPOIETIC AND LYMPHOID TISSUE | 6.305 | −0.346016434 |
| OCIAML5 | HAEMATOPOIETIC AND LYMPHOID TISSUE | 6.3062 | −0.344756857 |
| KMRC20 | KIDNEY | 6.3063 | −0.344651892 |
| LU65 | LUNG | 6.3082 | −0.342657561 |
| JIMT1 | BREAST | 6.3087 | −0.342132737 |
| SNU8 | OVARY | 6.3089 | −0.341922807 |
| KALS1 | CENTRAL NERVOUS SYSTEM | 6.3098 | −0.340978124 |
| SCABER | URINARY TRACT | 6.322 | −0.32817242 |
| OVMANA | OVARY | 6.3268 | −0.32313411 |
| TUHR10TKB | KIDNEY | 6.3302 | −0.319565307 |

TABLE 1-continued

Sensitivity data of 766 cancer cell lines treated with DNMDP

| Cell line | Lineage | DNMDP AUC | Robust Z-score |
|---|---|---|---|
| SUPM2 | HAEMATOPOIETIC AND LYMPHOID TISSUE | 6.3314 | −0.318305729 |
| JMSU1 | URINARY TRACT | 6.3317 | −0.317990835 |
| NCIH446 | LUNG | 6.3331 | −0.316521328 |
| COV434 | OVARY | 6.3341 | −0.31547168 |
| HCC38 | BREAST | 6.3361 | −0.313372384 |
| KMRC2 | KIDNEY | 6.3393 | −0.310013511 |
| SNU478 | BILIARY TRACT | 6.3432 | −0.305919884 |
| SUDHL1 | HAEMATOPOIETIC AND LYMPHOID TISSUE | 6.3444 | −0.304660306 |
| CMLT1 | HAEMATOPOIETIC AND LYMPHOID TISSUE | 6.3494 | −0.299412067 |
| UACC257 | SKIN | 6.3508 | −0.29794256 |
| NCIH1339 | LUNG | 6.3509 | −0.297837595 |
| M07E | HAEMATOPOIETIC AND LYMPHOID TISSUE | 6.3511 | −0.297627665 |
| KMRC3 | KIDNEY | 6.3514 | −0.297312771 |
| NCIH1693 | LUNG | 6.3603 | −0.287970905 |
| MM1S | HAEMATOPOIETIC AND LYMPHOID TISSUE | 6.3604 | −0.28786594 |
| HCC1143 | BREAST | 6.3611 | −0.287131186 |
| KATOIII | STOMACH | 6.3642 | −0.283877278 |
| MDAMB453 | BREAST | 6.3691 | −0.278734003 |
| J82 | URINARY TRACT | 6.3718 | −0.275899954 |
| CAL27 | UPPER AERODIGESTIVE TRACT | 6.3725 | −0.2751652 |
| HS766T | PANCREAS | 6.3727 | −0.274955271 |
| HCT8 | LARGE INTESTINE | 6.3733 | −0.274325482 |
| NCIH1581 | LUNG | 6.3747 | −0.272855975 |
| REH | HAEMATOPOIETIC AND LYMPHOID TISSUE | 6.3759 | −0.271596397 |
| MPP89 | PLEURA | 6.3817 | −0.265508439 |
| SNU761 | LIVER | 6.3819 | −0.26529851 |
| RH30 | SOFT TISSUE | 6.3841 | −0.262989284 |
| KURAMOCHI | OVARY | 6.3842 | −0.26288432 |
| HS936T | SKIN | 6.385 | −0.262044601 |
| HCC15 | LUNG | 6.3861 | −0.260889989 |
| F36P | HAEMATOPOIETIC AND LYMPHOID TISSUE | 6.388 | −0.258895657 |
| PANC0504 | PANCREAS | 6.3894 | −0.25742615 |
| NOMO1 | HAEMATOPOIETIC AND LYMPHOID TISSUE | 6.3925 | −0.254172242 |
| SKUT1 | SOFT TISSUE | 6.3987 | −0.247664425 |
| CCK81 | LARGE INTESTINE | 6.4043 | −0.241786397 |
| NCIH211 | LUNG | 6.4058 | −0.240211925 |
| NH6 | AUTONOMIC GANGLIA | 6.4066 | −0.239372206 |
| BECKER | CENTRAL NERVOUS SYSTEM | 6.4161 | −0.229400551 |
| NCIH1869 | LUNG | 6.4177 | −0.227721114 |
| ASPC1 | PANCREAS | 6.4186 | −0.226776431 |
| VMCUB1 | URINARY TRACT | 6.4199 | −0.225411889 |
| SNU398 | LIVER | 6.4206 | −0.224677136 |
| THP1 | HAEMATOPOIETIC AND LYMPHOID TISSUE | 6.4214 | −0.223837417 |
| HS611T | HAEMATOPOIETIC AND LYMPHOID TISSUE | 6.4224 | −0.222787769 |
| ONS76 | CENTRAL NERVOUS SYSTEM | 6.4253 | −0.21974379 |
| LOVO | LARGE INTESTINE | 6.4266 | −0.218379248 |
| GMS10 | CENTRAL NERVOUS SYSTEM | 6.4313 | −0.213445903 |
| RKO | LARGE INTESTINE | 6.4316 | −0.213131009 |
| ZR7530 | BREAST | 6.4339 | −0.210716818 |
| FU97 | STOMACH | 6.4421 | −0.202109705 |
| OCILY3 | HAEMATOPOIETIC AND LYMPHOID TISSUE | 6.4442 | −0.199905445 |
| BV173 | HAEMATOPOIETIC AND LYMPHOID TISSUE | 6.4448 | −0.199275656 |
| NCIH1568 | LUNG | 6.4489 | −0.1949721 |
| NCIH1155 | LUNG | 6.4497 | −0.194132381 |
| JURKAT | HAEMATOPOIETIC AND LYMPHOID TISSUE | 6.4524 | −0.191298332 |
| CW2 | LARGE INTESTINE | 6.4567 | −0.186784846 |
| RD | SOFT TISSUE | 6.4567 | −0.186784846 |
| RERFLCAI | LUNG | 6.4571 | −0.186364987 |
| YD10B | UPPER AERODIGESTIVE TRACT | 6.4579 | −0.185525268 |

TABLE 1-continued

| Sensitivity data of 766 cancer cell lines treated with DNMDP | | | |
|---|---|---|---|
| Cell line | Lineage | DNMDP AUC | Robust Z-score |
| SF295 | CENTRAL NERVOUS SYSTEM | 6.4581 | −0.185315339 |
| JJN3 | HAEMATOPOIETIC AND LYMPHOID TISSUE | 6.4585 | −0.18489548 |
| EB1 | HAEMATOPOIETIC AND LYMPHOID TISSUE | 6.4633 | −0.17985717 |
| KNS60 | CENTRAL NERVOUS SYSTEM | 6.4642 | −0.178912487 |
| X697 | HAEMATOPOIETIC AND LYMPHOID TISSUE | 6.4674 | −0.175553613 |
| TOV21G | OVARY | 6.4695 | −0.173349353 |
| JHH5 | LIVER | 6.4703 | −0.172509634 |
| OVTOKO | OVARY | 6.4718 | −0.170935162 |
| WM1799 | SKIN | 6.4744 | −0.168206078 |
| PL21 | HAEMATOPOIETIC AND LYMPHOID TISSUE | 6.4754 | −0.16715643 |
| CA46 | HAEMATOPOIETIC AND LYMPHOID TISSUE | 6.4772 | −0.165267064 |
| PATU8988S | PANCREAS | 6.479 | −0.163377697 |
| HCC44 | LUNG | 6.4794 | −0.162957838 |
| KARPAS299 | HAEMATOPOIETIC AND LYMPHOID TISSUE | 6.4827 | −0.159494 |
| PANC0327 | PANCREAS | 6.4856 | −0.156450021 |
| YD8 | UPPER AERODIGESTIVE TRACT | 6.4856 | −0.156450021 |
| GDM1 | HAEMATOPOIETIC AND LYMPHOID TISSUE | 6.4875 | −0.15445569 |
| IM95 | STOMACH | 6.4877 | −0.154245761 |
| HCT15 | LARGE INTESTINE | 6.4918 | −0.149942204 |
| WM793 | SKIN | 6.4939 | −0.147737944 |
| SHP77 | LUNG | 6.5008 | −0.140495373 |
| X8MGBA | CENTRAL NERVOUS SYSTEM | 6.5012 | −0.140075514 |
| OUMS23 | LARGE INTESTINE | 6.5015 | −0.139760619 |
| SW1116 | LARGE INTESTINE | 6.5032 | −0.137976218 |
| NCIH1703 | LUNG | 6.5035 | −0.137661324 |
| HLF | LIVER | 6.5042 | −0.13692657 |
| REC1 | HAEMATOPOIETIC AND LYMPHOID TISSUE | 6.5051 | −0.135981887 |
| ML1 | THYROID | 6.5066 | −0.134407415 |
| HOS | BONE | 6.5069 | −0.134092521 |
| SW837 | LARGE INTESTINE | 6.5072 | −0.133777626 |
| EHEB | HAEMATOPOIETIC AND LYMPHOID TISSUE | 6.5124 | −0.128319457 |
| HUH28 | BILIARY TRACT | 6.5145 | −0.126115197 |
| MDAMB157 | BREAST | 6.5173 | −0.123176182 |
| CHP212 | AUTONOMIC GANGLIA | 6.5178 | −0.122651359 |
| RMUGS | OVARY | 6.52 | −0.120342133 |
| NCIH2106 | LUNG | 6.5249 | −0.115198858 |
| SKLMS1 | SOFT TISSUE | 6.5254 | −0.114674034 |
| X647V | URINARY TRACT | 6.5257 | −0.11435914 |
| HS294T | SKIN | 6.5258 | −0.114254175 |
| CHAGOK1 | LUNG | 6.5292 | −0.110685372 |
| NCIH2228 | LUNG | 6.5304 | −0.109425795 |
| MHHCALL3 | HAEMATOPOIETIC AND LYMPHOID TISSUE | 6.5324 | −0.107326499 |
| TE6 | OESOPHAGUS | 6.5328 | −0.10690664 |
| MHHES1 | BONE | 6.5353 | −0.10428252 |
| X42MGBA | CENTRAL NERVOUS SYSTEM | 6.5397 | −0.099664069 |
| SH10TC | STOMACH | 6.5448 | −0.094310865 |
| HCC202 | BREAST | 6.5484 | −0.090532132 |
| ACHN | KIDNEY | 6.5518 | −0.08696333 |
| SCC25 | UPPER AERODIGESTIVE TRACT | 6.5527 | −0.086018646 |
| PANC0403 | PANCREAS | 6.5578 | −0.080665442 |
| A2780 | OVARY | 6.5613 | −0.076991674 |
| EBC1 | LUNG | 6.5617 | −0.076571815 |
| SW620 | LARGE INTESTINE | 6.5658 | −0.072268259 |
| SKMEL31 | SKIN | 6.5659 | −0.072163294 |
| PK45H | PANCREAS | 6.5666 | −0.07142854 |
| NCIH2030 | LUNG | 6.5688 | −0.069119315 |
| SKMES1 | LUNG | 6.5724 | −0.065340583 |
| NAMALWA | HAEMATOPOIETIC AND LYMPHOID TISSUE | 6.5738 | −0.063871075 |
| CAL12T | LUNG | 6.5741 | −0.063556181 |
| HPBALL | HAEMATOPOIETIC AND LYMPHOID TISSUE | 6.5743 | −0.063346251 |

TABLE 1-continued

Sensitivity data of 766 cancer cell lines treated with DNMDP

| Cell line | Lineage | DNMDP AUC | Robust Z-score |
|---|---|---|---|
| HT1080 | SOFT TISSUE | 6.5745 | −0.063136322 |
| OE33 | OESOPHAGUS | 6.5749 | −0.062716463 |
| SR786 | HAEMATOPOIETIC AND LYMPHOID TISSUE | 6.5751 | −0.062506533 |
| NCIH929 | HAEMATOPOIETIC AND LYMPHOID TISSUE | 6.5755 | −0.062086674 |
| OVCAR4 | OVARY | 6.5755 | −0.062086674 |
| T47D | BREAST | 6.5764 | −0.061141991 |
| HCC1937 | BREAST | 6.5773 | −0.060197308 |
| SKHEP1 | LIVER | 6.5773 | −0.060197308 |
| KMS26 | HAEMATOPOIETIC AND LYMPHOID TISSUE | 6.5778 | −0.059672484 |
| SNU1066 | UPPER AERODIGESTIVE TRACT | 6.5779 | −0.059567519 |
| SUPHD1 | HAEMATOPOIETIC AND LYMPHOID TISSUE | 6.5802 | −0.057153329 |
| L428 | HAEMATOPOIETIC AND LYMPHOID TISSUE | 6.5828 | −0.054424244 |
| PLCPRF5 | LIVER | 6.584 | −0.053164667 |
| MSTO211H | PLEURA | 6.5871 | −0.049910758 |
| GA10 | HAEMATOPOIETIC AND LYMPHOID TISSUE | 6.59 | −0.046866779 |
| HSC2 | UPPER AERODIGESTIVE TRACT | 6.59 | −0.046866779 |
| MKN74 | STOMACH | 6.5911 | −0.045712167 |
| TOLEDO | HAEMATOPOIETIC AND LYMPHOID TISSUE | 6.5926 | −0.044137695 |
| KARPAS620 | HAEMATOPOIETIC AND LYMPHOID TISSUE | 6.5931 | −0.043612871 |
| CALU6 | LUNG | 6.5932 | −0.043507906 |
| SNU1196 | BILIARY TRACT | 6.5947 | −0.041933434 |
| HGC27 | STOMACH | 6.595 | −0.04161854 |
| NCIH716 | LARGE INTESTINE | 6.5964 | −0.040149033 |
| HDMYZ | HAEMATOPOIETIC AND LYMPHOID TISSUE | 6.5974 | −0.039099385 |
| A3KAW | HAEMATOPOIETIC AND LYMPHOID TISSUE | 6.6031 | −0.033116392 |
| SNGM | ENDOMETRIUM | 6.6038 | −0.032381638 |
| CAL851 | BREAST | 6.6074 | −0.028602906 |
| JHUEM2 | ENDOMETRIUM | 6.608 | −0.027973117 |
| LN18 | CENTRAL NERVOUS SYSTEM | 6.6106 | −0.025244032 |
| VMRCRCZ | KIDNEY | 6.6107 | −0.025139067 |
| TE10 | OESOPHAGUS | 6.6127 | −0.023039772 |
| CAKI2 | KIDNEY | 6.614 | −0.021675229 |
| PK1 | PANCREAS | 6.6156 | −0.019995793 |
| TE1 | OESOPHAGUS | 6.6158 | −0.019785863 |
| IGR39 | SKIN | 6.6163 | −0.019261039 |
| NCIH1781 | LUNG | 6.6169 | −0.01863125 |
| A253 | SALIVARY GLAND | 6.6238 | −0.01138868 |
| NCIH727 | LUNG | 6.6253 | −0.009814208 |
| G361 | SKIN | 6.6284 | −0.006560299 |
| TYKNU | OVARY | 6.6296 | −0.005300722 |
| SNU1041 | UPPER AERODIGESTIVE TRACT | 6.6307 | −0.004146109 |
| JL1 | PLEURA | 6.6309 | −0.00393618 |
| SNU283 | LARGE INTESTINE | 6.6315 | −0.003306391 |
| HCT116 | LARGE INTESTINE | 6.632 | −0.002781567 |
| LS1034 | LARGE INTESTINE | 6.6323 | −0.002466673 |
| EFO21 | OVARY | 6.633 | −0.001731919 |
| DMS114 | LUNG | 6.6335 | −0.001207095 |
| SNU1077 | ENDOMETRIUM | 6.6342 | −0.000472342 |
| DAOY | CENTRAL NERVOUS SYSTEM | 6.6343 | −0.000367377 |
| NCIH2342 | LUNG | 6.6346 | −5.24824E−05 |
| MOLP8 | HAEMATOPOIETIC AND LYMPHOID TISSUE | 6.6347 | 5.24824E−05 |
| BHT101 | THYROID | 6.6351 | 0.000472342 |
| TE5 | OESOPHAGUS | 6.6355 | 0.000892201 |
| PSN1 | PANCREAS | 6.6403 | 0.005930511 |
| NCIH2170 | LUNG | 6.6424 | 0.008134771 |
| RCHACV | HAEMATOPOIETIC AND LYMPHOID TISSUE | 6.6426 | 0.008344701 |
| HUH6 | LIVER | 6.6437 | 0.009499314 |
| NCIH838 | LUNG | 6.6448 | 0.010653926 |
| YAPC | PANCREAS | 6.6485 | 0.014537624 |
| KYSE450 | OESOPHAGUS | 6.6505 | 0.016636919 |

TABLE 1-continued

Sensitivity data of 766 cancer cell lines treated with DNMDP

| Cell line | Lineage | DNMDP AUC | Robust Z-score |
|---|---|---|---|
| RERFLCMS | LUNG | 6.6512 | 0.017371673 |
| OVISE | OVARY | 6.6514 | 0.017581603 |
| HT55 | LARGE INTESTINE | 6.6554 | 0.021780194 |
| SNU899 | UPPER AERODIGESTIVE TRACT | 6.662 | 0.02870787 |
| NCIH226 | LUNG | 6.6624 | 0.02912773 |
| X639V | URINARY TRACT | 6.6635 | 0.030282342 |
| TE14 | OESOPHAGUS | 6.6652 | 0.032066744 |
| MKN45 | STOMACH | 6.6662 | 0.033116392 |
| UMUC3 | URINARY TRACT | 6.6662 | 0.033116392 |
| HEC6 | ENDOMETRIUM | 6.6667 | 0.033641216 |
| X253JBV | URINARY TRACT | 6.6694 | 0.036475265 |
| SKMEL24 | SKIN | 6.6712 | 0.038364631 |
| VMRCLCD | LUNG | 6.6718 | 0.03899442 |
| DLD1 | LARGE INTESTINE | 6.6751 | 0.042458258 |
| ECC12 | STOMACH | 6.6785 | 0.046027061 |
| WSUDLCL2 | HAEMATOPOIETIC AND LYMPHOID TISSUE | 6.6801 | 0.047706498 |
| PFEIFFER | HAEMATOPOIETIC AND LYMPHOID TISSUE | 6.6804 | 0.048021392 |
| NCIH2087 | LUNG | 6.6806 | 0.048231322 |
| NCIH2029 | LUNG | 6.6826 | 0.050330617 |
| SJSA1 | BONE | 6.6844 | 0.052219984 |
| A172 | CENTRAL NERVOUS SYSTEM | 6.6858 | 0.053689491 |
| SNU1033 | LARGE INTESTINE | 6.6873 | 0.055263963 |
| TM31 | CENTRAL NERVOUS SYSTEM | 6.6885 | 0.05652354 |
| X2313287 | STOMACH | 6.6886 | 0.056628505 |
| SQ1 | LUNG | 6.6945 | 0.062821428 |
| SUPT11 | HAEMATOPOIETIC AND LYMPHOID TISSUE | 6.695 | 0.063346251 |
| NCIH2023 | LUNG | 6.6954 | 0.063766111 |
| HCC1569 | BREAST | 6.6976 | 0.066075336 |
| TT2609C02 | THYROID | 6.7014 | 0.070063998 |
| SW1990 | PANCREAS | 6.7019 | 0.070588822 |
| OVSAHO | OVARY | 6.7028 | 0.071533505 |
| NCIH841 | LUNG | 6.7036 | 0.072373224 |
| ME1 | HAEMATOPOIETIC AND LYMPHOID TISSUE | 6.7039 | 0.072688118 |
| COLO205 | LARGE INTESTINE | 6.7052 | 0.07405266 |
| TCCSUP | URINARY TRACT | 6.7056 | 0.074472519 |
| TE11 | OESOPHAGUS | 6.7063 | 0.075207273 |
| TE4 | OESOPHAGUS | 6.707 | 0.075942026 |
| NCIH1694 | LUNG | 6.7095 | 0.078566146 |
| KP4 | PANCREAS | 6.7102 | 0.0793009 |
| CL11 | LARGE INTESTINE | 6.711 | 0.080140618 |
| NCIH596 | LUNG | 6.7123 | 0.08150516 |
| OCIAML3 | HAEMATOPOIETIC AND LYMPHOID TISSUE | 6.7152 | 0.084549139 |
| KMH2 | HAEMATOPOIETIC AND LYMPHOID TISSUE | 6.7155 | 0.084864034 |
| PK59 | PANCREAS | 6.7163 | 0.085703752 |
| HDLM2 | HAEMATOPOIETIC AND LYMPHOID TISSUE | 6.7172 | 0.086648435 |
| ES2 | OVARY | 6.7183 | 0.087803048 |
| SKNDZ | AUTONOMIC GANGLIA | 6.7192 | 0.088747731 |
| NCIH650 | LUNG | 6.7194 | 0.088957661 |
| CAL62 | THYROID | 6.721 | 0.090637097 |
| MDAMB231 | BREAST | 6.7222 | 0.091896675 |
| HARA | LUNG | 6.7238 | 0.093576111 |
| MFE319 | ENDOMETRIUM | 6.7242 | 0.093995971 |
| LCLC103H | LUNG | 6.7269 | 0.09683002 |
| OE19 | OESOPHAGUS | 6.7273 | 0.097249879 |
| HT144 | SKIN | 6.7297 | 0.099769034 |
| HEC251 | ENDOMETRIUM | 6.7301 | 0.100188893 |
| A4FUK | HAEMATOPOIETIC AND LYMPHOID TISSUE | 6.7317 | 0.10186833 |
| K562 | HAEMATOPOIETIC AND LYMPHOID TISSUE | 6.7319 | 0.102078259 |
| HEC59 | ENDOMETRIUM | 6.7321 | 0.102288189 |
| NCIH1341 | LUNG | 6.7337 | 0.103967626 |
| A204 | SOFT TISSUE | 6.7338 | 0.10407259 |
| OV7 | OVARY | 6.7346 | 0.104912309 |
| OV90 | OVARY | 6.7381 | 0.108586076 |
| HCC827 | LUNG | 6.7384 | 0.108900971 |
| DU4475 | BREAST | 6.742 | 0.112679703 |

TABLE 1-continued

Sensitivity data of 766 cancer cell lines treated with DNMDP

| Cell line | Lineage | DNMDP AUC | Robust Z-score |
|---|---|---|---|
| SKMEL1 | SKIN | 6.742 | 0.112679703 |
| KYSE70 | OESOPHAGUS | 6.7428 | 0.113519422 |
| CHP126 | AUTONOMIC GANGLIA | 6.7459 | 0.11677333 |
| DETROIT562 | UPPER AERODIGESTIVE TRACT | 6.7465 | 0.117403119 |
| CMK | HAEMATOPOIETIC AND LYMPHOID TISSUE | 6.7483 | 0.119292485 |
| X769P | KIDNEY | 6.7486 | 0.11960738 |
| DEL | HAEMATOPOIETIC AND LYMPHOID TISSUE | 6.7494 | 0.120447098 |
| PANC0813 | PANCREAS | 6.751 | 0.122126535 |
| COLO201 | LARGE INTESTINE | 6.752 | 0.123176182 |
| SKNMC | BONE | 6.7533 | 0.124540725 |
| CALU3 | LUNG | 6.7536 | 0.124855619 |
| SNU1076 | UPPER AERODIGESTIVE TRACT | 6.7574 | 0.128844281 |
| HCC78 | LUNG | 6.7625 | 0.134197486 |
| ESS1 | ENDOMETRIUM | 6.7626 | 0.13430245 |
| NCIH1755 | LUNG | 6.771 | 0.143119493 |
| HPAFII | PANCREAS | 6.7751 | 0.147423049 |
| CAKI1 | KIDNEY | 6.7755 | 0.147842908 |
| COLO783 | SKIN | 6.778 | 0.150467028 |
| NCIH2405 | LUNG | 6.7785 | 0.150991852 |
| KNS81 | CENTRAL NERVOUS SYSTEM | 6.7793 | 0.15183157 |
| HCC95 | LUNG | 6.7794 | 0.151936535 |
| HL60 | HAEMATOPOIETIC AND LYMPHOID TISSUE | 6.7796 | 0.152146465 |
| FADU | UPPER AERODIGESTIVE TRACT | 6.7809 | 0.153511007 |
| TE617T | SOFT TISSUE | 6.782 | 0.15466562 |
| KMBC2 | URINARY TRACT | 6.7837 | 0.156450021 |
| HCC1171 | LUNG | 6.7838 | 0.156554986 |
| CAPAN1 | PANCREAS | 6.786 | 0.158864211 |
| CORL88 | LUNG | 6.7915 | 0.164637275 |
| PECAPJ49 | UPPER AERODIGESTIVE TRACT | 6.7927 | 0.165896852 |
| SF126 | CENTRAL NERVOUS SYSTEM | 6.7933 | 0.166526641 |
| GSS | STOMACH | 6.794 | 0.167261395 |
| U87MG | CENTRAL NERVOUS SYSTEM | 6.7949 | 0.168206078 |
| HEYA8 | OVARY | 6.7972 | 0.170620268 |
| HT1376 | URINARY TRACT | 6.7994 | 0.172929493 |
| COLO792 | SKIN | 6.7997 | 0.173244388 |
| SKMEL2 | SKIN | 6.8019 | 0.175553613 |
| NCIH460 | LUNG | 6.8048 | 0.178597592 |
| KU1919 | URINARY TRACT | 6.8061 | 0.179962134 |
| SNU407 | LARGE INTESTINE | 6.8062 | 0.180067099 |
| KU812 | HAEMATOPOIETIC AND LYMPHOID TISSUE | 6.8063 | 0.180172064 |
| NCIH747 | LARGE INTESTINE | 6.8075 | 0.181431642 |
| A101D | SKIN | 6.8089 | 0.182901149 |
| PATU8988T | PANCREAS | 6.8099 | 0.183950797 |
| HS895T | SKIN | 6.8118 | 0.185945128 |
| HMC18 | BREAST | 6.8147 | 0.188989107 |
| X253J | URINARY TRACT | 6.8153 | 0.189618895 |
| TE9 | OESOPHAGUS | 6.8154 | 0.18972386 |
| LS123 | LARGE INTESTINE | 6.8175 | 0.191928121 |
| MCAS | OVARY | 6.8199 | 0.194447276 |
| SW403 | LARGE INTESTINE | 6.8208 | 0.195391959 |
| MDST8 | LARGE INTESTINE | 6.8209 | 0.195496924 |
| RCM1 | LARGE INTESTINE | 6.8231 | 0.197806149 |
| NCIH1650 | LUNG | 6.825 | 0.19980048 |
| RPMI8226 | HAEMATOPOIETIC AND LYMPHOID TISSUE | 6.8256 | 0.200430269 |
| SUDHL8 | HAEMATOPOIETIC AND LYMPHOID TISSUE | 6.8258 | 0.200640198 |
| HEPG2 | LIVER | 6.8274 | 0.202319635 |
| HT115 | LARGE INTESTINE | 6.8303 | 0.205363614 |
| KYSE520 | OESOPHAGUS | 6.8305 | 0.205573544 |
| ISHIKAWAHERAKLIO02ER | ENDOMETRIUM | 6.8313 | 0.206413262 |
| RT112 | URINARY TRACT | 6.8313 | 0.206413262 |
| SNU308 | BILIARY TRACT | 6.8314 | 0.206518227 |
| HCC1806 | BREAST | 6.8314 | 0.206518227 |
| NCIH2085 | LUNG | 6.8317 | 0.206833121 |
| EFO27 | OVARY | 6.832 | 0.207148015 |
| NCIH2052 | PLEURA | 6.8321 | 0.20725298 |

TABLE 1-continued

| Sensitivity data of 766 cancer cell lines treated with DNMDP | | | |
|---|---|---|---|
| Cell line | Lineage | DNMDP AUC | Robust Z-score |
| HSC4 | UPPER AERODIGESTIVE TRACT | 6.8327 | 0.207882769 |
| KYSE140 | OESOPHAGUS | 6.836 | 0.211346607 |
| LC1SQSF | LUNG | 6.8361 | 0.211451572 |
| KMRC1 | KIDNEY | 6.8362 | 0.211556537 |
| HUPT3 | PANCREAS | 6.837 | 0.212396255 |
| NCIH1838 | LUNG | 6.8375 | 0.212921079 |
| T24 | URINARY TRACT | 6.8383 | 0.213760797 |
| WM115 | SKIN | 6.8396 | 0.21512534 |
| KASUMI1 | HAEMATOPOIETIC AND LYMPHOID TISSUE | 6.8439 | 0.219638826 |
| GAMG | CENTRAL NERVOUS SYSTEM | 6.8471 | 0.222997699 |
| SBC5 | LUNG | 6.8494 | 0.225411889 |
| WM2664 | SKIN | 6.8521 | 0.228245938 |
| D283MED | CENTRAL NERVOUS SYSTEM | 6.857 | 0.233389213 |
| MIAPACA2 | PANCREAS | 6.8607 | 0.23727291 |
| BL70 | HAEMATOPOIETIC AND LYMPHOID TISSUE | 6.8619 | 0.238532488 |
| NCIH1623 | LUNG | 6.862 | 0.238637453 |
| BHY | UPPER AERODIGESTIVE TRACT | 6.8627 | 0.239372206 |
| OVCAR8 | OVARY | 6.8637 | 0.240421854 |
| SNU840 | OVARY | 6.8651 | 0.241891361 |
| CFPAC1 | PANCREAS | 6.8671 | 0.243990657 |
| HS944T | SKIN | 6.8697 | 0.246719742 |
| LK2 | LUNG | 6.8724 | 0.249553791 |
| JHH1 | LIVER | 6.8737 | 0.250918333 |
| OVKATE | OVARY | 6.8742 | 0.251443157 |
| T84 | LARGE INTESTINE | 6.8791 | 0.256586432 |
| SW1573 | LUNG | 6.8813 | 0.258895657 |
| KYSE30 | OESOPHAGUS | 6.8825 | 0.260155235 |
| DANG | PANCREAS | 6.8825 | 0.260155235 |
| SU8686 | PANCREAS | 6.8851 | 0.26288432 |
| YD15 | SALIVARY GLAND | 6.8858 | 0.263619073 |
| COLO680N | OESOPHAGUS | 6.8864 | 0.264248862 |
| SUDHL6 | HAEMATOPOIETIC AND LYMPHOID TISSUE | 6.887 | 0.264878651 |
| SNU626 | CENTRAL NERVOUS SYSTEM | 6.8886 | 0.266558087 |
| SNU1105 | CENTRAL NERVOUS SYSTEM | 6.8918 | 0.269916961 |
| BT20 | BREAST | 6.8931 | 0.271281503 |
| FTC133 | THYROID | 6.8949 | 0.273170869 |
| P12ICHIKAWA | HAEMATOPOIETIC AND LYMPHOID TISSUE | 6.8951 | 0.273380799 |
| NCIH292 | LUNG | 6.8954 | 0.273695693 |
| JHH2 | LIVER | 6.9004 | 0.278943933 |
| RCC10RGB | KIDNEY | 6.9009 | 0.279468757 |
| JHOC5 | OVARY | 6.9036 | 0.282302806 |
| X786O | KIDNEY | 6.9057 | 0.284507067 |
| AN3CA | ENDOMETRIUM | 6.9081 | 0.287026222 |
| KP3 | PANCREAS | 6.909 | 0.287970905 |
| HEC151 | ENDOMETRIUM | 6.9099 | 0.288915588 |
| KE39 | STOMACH | 6.9103 | 0.289335447 |
| HS822T | BONE | 6.9115 | 0.290595024 |
| A375 | SKIN | 6.9117 | 0.290804954 |
| MORCPR | LUNG | 6.9126 | 0.291749637 |
| C2BBE1 | LARGE INTESTINE | 6.9144 | 0.293639003 |
| NCIH2452 | PLEURA | 6.9169 | 0.296263123 |
| TCCPAN2 | PANCREAS | 6.9184 | 0.297837595 |
| VMRCRCW | KIDNEY | 6.9222 | 0.301826257 |
| NCIH810 | LUNG | 6.9222 | 0.301826257 |
| PC3 | PROSTATE | 6.9226 | 0.302246116 |
| MDAMB435S | SKIN | 6.9227 | 0.302351081 |
| NCIH322 | LUNG | 6.9254 | 0.30518513 |
| MOLP2 | HAEMATOPOIETIC AND LYMPHOID TISSUE | 6.928 | 0.307914215 |
| HCC366 | LUNG | 6.9295 | 0.309488687 |
| KELLY | AUTONOMIC GANGLIA | 6.9352 | 0.31547168 |
| AGS | STOMACH | 6.9378 | 0.318200764 |
| MDAMB468 | BREAST | 6.9388 | 0.319250412 |
| SNUC5 | LARGE INTESTINE | 6.939 | 0.319460342 |
| HCC1195 | LUNG | 6.941 | 0.321559638 |
| NB1 | AUTONOMIC GANGLIA | 6.9466 | 0.327437666 |
| NCIH2126 | LUNG | 6.9473 | 0.32817242 |
| HT | HAEMATOPOIETIC AND LYMPHOID TISSUE | 6.9476 | 0.328487314 |

TABLE 1-continued

Sensitivity data of 766 cancer cell lines treated with DNMDP

| Cell line | Lineage | DNMDP AUC | Robust Z-score |
|---|---|---|---|
| SW48 | LARGE INTESTINE | 6.9505 | 0.331531293 |
| QGP1 | PANCREAS | 6.9517 | 0.33279087 |
| NUGC3 | STOMACH | 6.9527 | 0.333840518 |
| SNU719 | STOMACH | 6.9544 | 0.33562492 |
| SKES1 | BONE | 6.9576 | 0.338983793 |
| OVK18 | OVARY | 6.9579 | 0.339298688 |
| HEC1B | ENDOMETRIUM | 6.9583 | 0.339718547 |
| KLE | ENDOMETRIUM | 6.9584 | 0.339823511 |
| HEC50B | ENDOMETRIUM | 6.9622 | 0.343812174 |
| TF1 | HAEMATOPOIETIC AND LYMPHOID TISSUE | 6.9682 | 0.350110061 |
| AM38 | CENTRAL NERVOUS SYSTEM | 6.9715 | 0.353573899 |
| HCC1954 | BREAST | 6.9728 | 0.354938441 |
| MELHO | SKIN | 6.9769 | 0.359241998 |
| EN | ENDOMETRIUM | 6.9773 | 0.359661857 |
| HCC2108 | LUNG | 6.9789 | 0.361341294 |
| X22RV1 | PROSTATE | 6.9813 | 0.363860449 |
| PATU8902 | PANCREAS | 6.9874 | 0.370263301 |
| LN229 | CENTRAL NERVOUS SYSTEM | 6.9883 | 0.371207984 |
| GI1 | CENTRAL NERVOUS SYSTEM | 6.9897 | 0.372677491 |
| SNU213 | PANCREAS | 6.9923 | 0.375406576 |
| COLO684 | ENDOMETRIUM | 6.993 | 0.376141329 |
| SNU738 | CENTRAL NERVOUS SYSTEM | 6.9945 | 0.377715801 |
| JK1 | HAEMATOPOIETIC AND LYMPHOID TISSUE | 6.9966 | 0.379920062 |
| KYSE510 | OESOPHAGUS | 6.9987 | 0.382124322 |
| NCIH1299 | LUNG | 6.9991 | 0.382544181 |
| IGROV1 | OVARY | 7.0026 | 0.386217949 |
| ACCMESO1 | PLEURA | 7.0033 | 0.386952703 |
| BICR16 | UPPER AERODIGESTIVE TRACT | 7.0071 | 0.390941365 |
| HCC2279 | LUNG | 7.0072 | 0.39104633 |
| PANC1 | PANCREAS | 7.0096 | 0.393565485 |
| CCFSTTG1 | CENTRAL NERVOUS SYSTEM | 7.0119 | 0.395979675 |
| SNU668 | STOMACH | 7.0126 | 0.396714428 |
| SW1271 | LUNG | 7.0143 | 0.39849883 |
| SUDHL4 | HAEMATOPOIETIC AND LYMPHOID TISSUE | 7.0162 | 0.400493161 |
| GCT | SOFT TISSUE | 7.0174 | 0.401752738 |
| TT | THYROID | 7.0183 | 0.402697421 |
| DMS454 | LUNG | 7.019 | 0.403432175 |
| LS180 | LARGE INTESTINE | 7.0225 | 0.407105943 |
| SNU182 | LIVER | 7.0252 | 0.409939992 |
| KNS62 | LUNG | 7.0253 | 0.410044957 |
| OC314 | OVARY | 7.0273 | 0.412144253 |
| RH41 | SOFT TISSUE | 7.0285 | 0.41340383 |
| NCIH1373 | LUNG | 7.0318 | 0.416867668 |
| BEN | LUNG | 7.0341 | 0.419281858 |
| MESSA | SOFT TISSUE | 7.0401 | 0.425579746 |
| HEC1A | ENDOMETRIUM | 7.0465 | 0.432297493 |
| L363 | HAEMATOPOIETIC AND LYMPHOID TISSUE | 7.0473 | 0.433137211 |
| CAL29 | URINARY TRACT | 7.0497 | 0.435656366 |
| RAJI | HAEMATOPOIETIC AND LYMPHOID TISSUE | 7.0524 | 0.438490415 |
| ZR751 | BREAST | 7.054 | 0.440169852 |
| KYSE180 | OESOPHAGUS | 7.0541 | 0.440274817 |
| LOXIMVI | SKIN | 7.058 | 0.444368444 |
| YD38 | UPPER AERODIGESTIVE TRACT | 7.06 | 0.446467739 |
| SNU410 | PANCREAS | 7.0646 | 0.45129612 |
| NCIH2291 | LUNG | 7.0654 | 0.452135838 |
| PANC0203 | PANCREAS | 7.0662 | 0.452975556 |
| NCIH1792 | LUNG | 7.0701 | 0.457069183 |
| SW1088 | CENTRAL NERVOUS SYSTEM | 7.0786 | 0.46599119 |
| SKMEL30 | SKIN | 7.079 | 0.46641105 |
| KM12 | LARGE INTESTINE | 7.0792 | 0.466620979 |
| HEC108 | ENDOMETRIUM | 7.0804 | 0.467880557 |
| NCIH526 | LUNG | 7.0825 | 0.470084817 |
| NCIH661 | LUNG | 7.0832 | 0.470819571 |
| KYSE150 | OESOPHAGUS | 7.0859 | 0.47365362 |
| TUHR4TKB | KIDNEY | 7.0861 | 0.47386355 |
| U251MG | CENTRAL NERVOUS SYSTEM | 7.091 | 0.479006825 |
| MKN1 | STOMACH | 7.0915 | 0.479531649 |
| DMS273 | LUNG | 7.0958 | 0.484045135 |

TABLE 1-continued

Sensitivity data of 766 cancer cell lines treated with DNMDP

| Cell line | Lineage | DNMDP AUC | Robust Z-score |
|---|---|---|---|
| HS683 | CENTRAL NERVOUS SYSTEM | 7.0975 | 0.485829536 |
| HS746T | STOMACH | 7.1012 | 0.489713233 |
| OAW42 | OVARY | 7.1038 | 0.492442318 |
| KYO1 | HAEMATOPOIETIC AND LYMPHOID TISSUE | 7.1048 | 0.493491966 |
| HS688AT | SKIN | 7.1049 | 0.493596931 |
| SIGM5 | HAEMATOPOIETIC AND LYMPHOID TISSUE | 7.1077 | 0.496535945 |
| HUCCT1 | BILIARY TRACT | 7.1094 | 0.498320346 |
| HS819T | BONE | 7.1097 | 0.498635241 |
| HCC1588 | LUNG | 7.1149 | 0.50409341 |
| KPL1 | BREAST | 7.1178 | 0.507137389 |
| KE97 | HAEMATOPOIETIC AND LYMPHOID TISSUE | 7.1187 | 0.508082072 |
| HCC2218 | BREAST | 7.1208 | 0.510286332 |
| OCIM1 | HAEMATOPOIETIC AND LYMPHOID TISSUE | 7.1253 | 0.515009748 |
| NCIH441 | LUNG | 7.1284 | 0.518263657 |
| NCIH1092 | LUNG | 7.139 | 0.529389924 |
| SKMEL28 | SKIN | 7.1392 | 0.529599854 |
| HPAC | PANCREAS | 7.1394 | 0.529809784 |
| SAOS2 | BONE | 7.1406 | 0.531069361 |
| RL952 | ENDOMETRIUM | 7.1432 | 0.533798446 |
| SKNAS | AUTONOMIC GANGLIA | 7.145 | 0.535687812 |
| CAL148 | BREAST | 7.1477 | 0.538521861 |
| DMS79 | LUNG | 7.1572 | 0.548493516 |
| EFE184 | ENDOMETRIUM | 7.1614 | 0.552902038 |
| SUPT1 | HAEMATOPOIETIC AND LYMPHOID TISSUE | 7.167 | 0.558780066 |
| NMCG1 | CENTRAL NERVOUS SYSTEM | 7.1746 | 0.56675739 |
| NCIH358 | LUNG | 7.1753 | 0.567492144 |
| TE441T | SOFT TISSUE | 7.1772 | 0.569486475 |
| MELJUSO | SKIN | 7.1877 | 0.580507778 |
| IPC298 | SKIN | 7.1984 | 0.59173901 |
| SW1353 | BONE | 7.1985 | 0.591843975 |
| CAL33 | UPPER AERODIGESTIVE TRACT | 7.2038 | 0.597407109 |
| SNU489 | CENTRAL NERVOUS SYSTEM | 7.2056 | 0.599296475 |
| LCLC97TM1 | LUNG | 7.2086 | 0.602445419 |
| BICR56 | UPPER AERODIGESTIVE TRACT | 7.2108 | 0.604754644 |
| NCIH508 | LARGE INTESTINE | 7.2176 | 0.61189225 |
| HSC3 | UPPER AERODIGESTIVE TRACT | 7.2237 | 0.618295103 |
| SNU878 | LIVER | 7.2238 | 0.618400067 |
| CAMA1 | BREAST | 7.2254 | 0.620079504 |
| LS411N | LARGE INTESTINE | 7.2279 | 0.622703624 |
| YKG1 | CENTRAL NERVOUS SYSTEM | 7.2376 | 0.632885208 |
| JHH6 | LIVER | 7.2377 | 0.632990173 |
| KG1C | CENTRAL NERVOUS SYSTEM | 7.238 | 0.633305068 |
| BT474 | BREAST | 7.2422 | 0.637713589 |
| SNU1079 | BILIARY TRACT | 7.2463 | 0.642017145 |
| KARPAS422 | HAEMATOPOIETIC AND LYMPHOID TISSUE | 7.2487 | 0.6445363 |
| HEC265 | ENDOMETRIUM | 7.2509 | 0.646845526 |
| NCIH2444 | LUNG | 7.2606 | 0.65702711 |
| NUDHL1 | HAEMATOPOIETIC AND LYMPHOID TISSUE | 7.2677 | 0.664479611 |
| AMO1 | HAEMATOPOIETIC AND LYMPHOID TISSUE | 7.2764 | 0.673611547 |
| HCC1833 | LUNG | 7.2887 | 0.686522217 |
| SNUC4 | LARGE INTESTINE | 7.2927 | 0.690720808 |
| HDQP1 | BREAST | 7.2935 | 0.691560527 |
| OV56 | OVARY | 7.2957 | 0.693869752 |
| P3HR1 | HAEMATOPOIETIC AND LYMPHOID TISSUE | 7.2973 | 0.695549189 |
| NUGC4 | STOMACH | 7.2991 | 0.697438555 |
| U2OS | BONE | 7.3013 | 0.69974778 |
| SNU886 | LIVER | 7.3032 | 0.701742112 |
| NCIH28 | PLEURA | 7.3081 | 0.706885386 |
| SNU601 | STOMACH | 7.3091 | 0.707935034 |
| ECC10 | STOMACH | 7.3182 | 0.71748683 |
| LS513 | LARGE INTESTINE | 7.3199 | 0.719271232 |
| CAL120 | BREAST | 7.32 | 0.719376196 |
| SNU1040 | LARGE INTESTINE | 7.3288 | 0.728613098 |

TABLE 1-continued

| Sensitivity data of 766 cancer cell lines treated with DNMDP | | | |
|---|---|---|---|
| Cell line | Lineage | DNMDP AUC | Robust Z-score |
| NCIH2171 | LUNG | 7.3416 | 0.742048591 |
| SUDHL5 | HAEMATOPOIETIC AND LYMPHOID TISSUE | 7.3508 | 0.751705352 |
| BFTC905 | URINARY TRACT | 7.3514 | 0.752335141 |
| HT29 | LARGE INTESTINE | 7.364 | 0.765560705 |
| RPMI7951 | SKIN | 7.375 | 0.777106832 |
| AML193 | HAEMATOPOIETIC AND LYMPHOID TISSUE | 7.3753 | 0.777421726 |
| MEC1 | HAEMATOPOIETIC AND LYMPHOID TISSUE | 7.376 | 0.778156479 |
| HEP3B217 | LIVER | 7.4062 | 0.809855846 |
| SNU475 | LIVER | 7.4091 | 0.812899825 |
| HUH1 | LIVER | 7.4298 | 0.834627537 |
| HUPT4 | PANCREAS | 7.4555 | 0.861603488 |
| IMR32 | AUTONOMIC GANGLIA | 7.4593 | 0.865592151 |
| NCIH889 | LUNG | 7.4952 | 0.903274511 |
| HCC2935 | LUNG | 7.5084 | 0.917129863 |
| MC116 | HAEMATOPOIETIC AND LYMPHOID TISSUE | 7.5146 | 0.92363768 |
| X5637 | URINARY TRACT | 7.5183 | 0.927521377 |
| SKM1 | HAEMATOPOIETIC AND LYMPHOID TISSUE | 7.5234 | 0.932874582 |
| SKBR3 | BREAST | 7.5494 | 0.960165427 |
| EM2 | HAEMATOPOIETIC AND LYMPHOID TISSUE | 7.5755 | 0.987561238 |
| RI1 | HAEMATOPOIETIC AND LYMPHOID TISSUE | 7.5915 | 1.004355605 |
| SIMA | AUTONOMIC GANGLIA | 7.6032 | 1.016636485 |
| FUOV1 | OVARY | 7.6122 | 1.026083316 |
| SNUC2A | LARGE INTESTINE | 7.6165 | 1.030596802 |
| SNU61 | LARGE INTESTINE | 7.6228 | 1.037209584 |
| CAPAN2 | PANCREAS | 7.6273 | 1.041933 |
| SNU216 | STOMACH | 7.6319 | 1.04676138 |
| MOLM13 | HAEMATOPOIETIC AND LYMPHOID TISSUE | 7.646 | 1.061561416 |
| HUNS1 | HAEMATOPOIETIC AND LYMPHOID TISSUE | 7.6648 | 1.081294796 |
| HCC1438 | LUNG | 7.7264 | 1.145953108 |
| NCIH2196 | LUNG | 7.7386 | 1.158758812 |
| SNU466 | CENTRAL NERVOUS SYSTEM | 7.7589 | 1.180066665 |
| SUDHL10 | HAEMATOPOIETIC AND LYMPHOID TISSUE | 7.7977 | 1.220793004 |
| SNU46 | UPPER AERODIGESTIVE TRACT | 7.8035 | 1.226880962 |
| CALU1 | LUNG | 7.8185 | 1.242625681 |
| BFTC909 | KIDNEY | 7.9189 | 1.348010331 |
| JVM3 | HAEMATOPOIETIC AND LYMPHOID TISSUE | 7.961 | 1.392200508 |
| MHHCALL4 | HAEMATOPOIETIC AND LYMPHOID TISSUE | 8.031 | 1.465675862 |
| JURLMK1 | HAEMATOPOIETIC AND LYMPHOID TISSUE | 8.1126 | 1.551327131 |
| KE37 | HAEMATOPOIETIC AND LYMPHOID TISSUE | 8.1163 | 1.555210829 |
| S117 | SOFT TISSUE | 8.2668 | 1.713182839 |
| KMS21BM | HAEMATOPOIETIC AND LYMPHOID TISSUE | 8.3309 | 1.780465271 |
| KYM1 | SOFT TISSUE | 8.4417 | 1.896766259 |
| CORL95 | LUNG | 8.5762 | 2.037943903 |
| MHHNB11 | AUTONOMIC GANGLIA | 8.8255 | 2.299621128 |
| MDAMB361 | BREAST | 9.2909 | 2.788127266 |

Example 2. Identification of PDE3A as a Putative Target of DNMDP

Figure 5A:
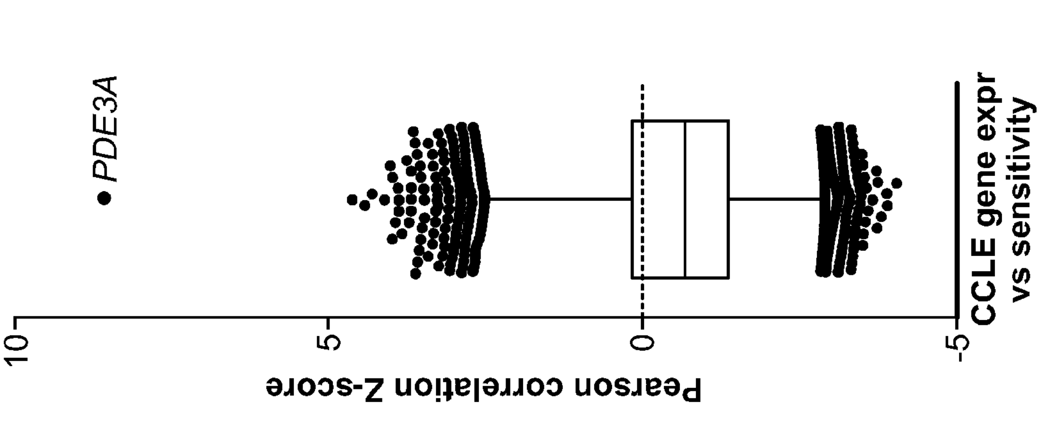
FIGS. 5A-5C show that Phosphodiesterase 3A (PDE3A) expression correlated with sensitivity to 6-(4-(diethylamino)-3-nitrophenyl)-5-methyl-4,5-dihydropyridazin-3(2H)-one (DNMDP), but inhibition of PDE3A mediated cAMP hydrolysis did not correlate with cytotoxicity.
Figure 5B:
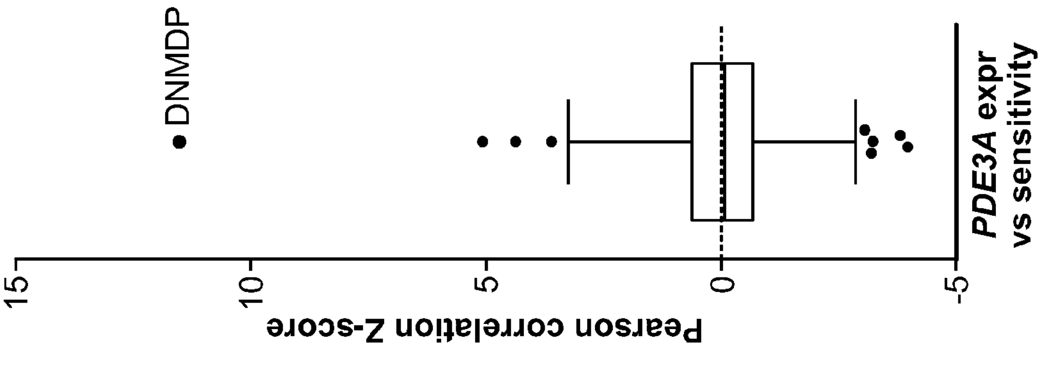
Figure 18:
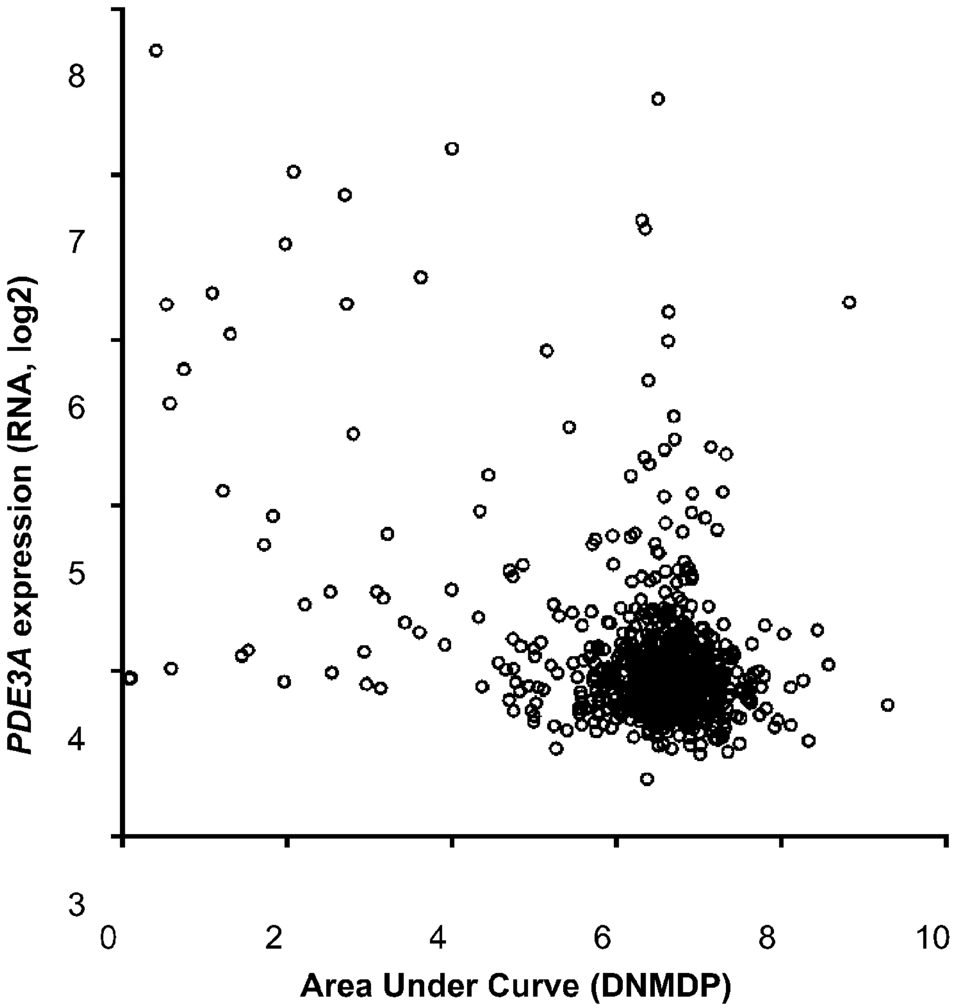
FIG. 18 is a scatterplot of PDE3A mRNA expression and sensitivity to DNMDP of 766 cancer cell lines.

Given the potent cell-selective growth inhibition by 6-(4-(diethylamino)-3-nitrophenyl)-5-methyl-4,5-dihydropyridazin-3(2H)-one (DNMDP), its mechanism of action was examined in more detail. To determine the molecular target of DNMDP, chemogenomic analysis was performed of the 766 tested cell lines, previously characterized for mutations, copy number, and gene expression features as part of the Cancer Cell Line Encyclopedia (CCLE, Barretina et al., 2012), to look for correlation between these genomic features and DNMDP sensitivity. Analysis of Pearson correlations between DNMDP sensitivity and expression of individual genes across the cell line set showed a strong correlation with expression of the PDE3A gene, encoding phosphodiesterase 3A (FIG. 5A). The correlation between DNMDP sensitivity and PDE3A expression is not perfect (FIG. 18), and it is possible that some errors are introduced due to the high-throughput nature of the cell line sensitivity characterization, as manual validation for all 766 cell lines was not logistically feasible. Mutation and copy number features, in contrast, did not correlate with DNMDP sensitivity. Conversely, of 480 compounds tested, DNMDP sensitivity was the closest correlate of PDE3A expression (FIG. 5B), indicating that cancer cell lines with high PDE3A expression were more distinctly sensitive to DNMDP than to any other tested compound. In contrast to the motivation of the initial screen, there was no correlation between TP53 mutation, or other measures of p53 function, and DNMDP sensitivity.

Figure 6A:
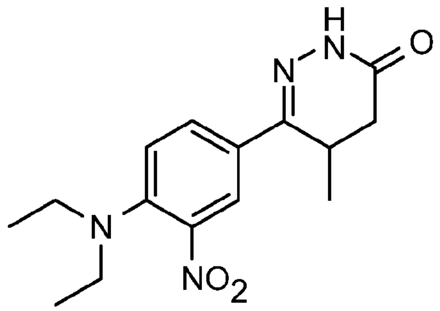
FIGS. 6A-6C show chemical structures of 6-(4-(diethylamino)-3-nitrophenyl)-5-methyl-4,5-dihydropyridazin-3(2H)-one (DNMDP), siguazodan and levosimendan, respectively.
Figure 6B:
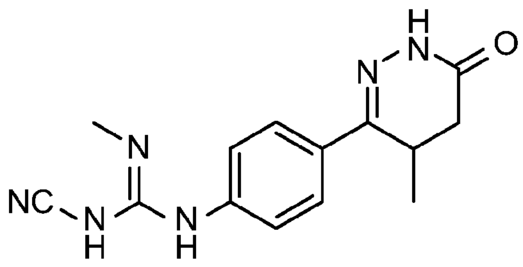
Figure 6C:
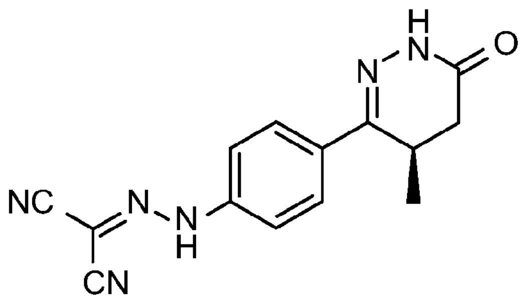

Given these results and the clear structural similarity of DNMDP to known PDE3 inhibitors, e.g., levosimendan and siguazodan (FIGS. 6A-6C), biochemical analysis of DNMDP against 19 phosphodiesterases representing 11 PDE super families was performed. At a concentration of 100 nM, DNMDP specifically inhibited both PDE3A and PDE3B, weakly inhibited PDE10, and had little or no detectable effect on other phosphodiesterases (Table 2).

Figure 5C:
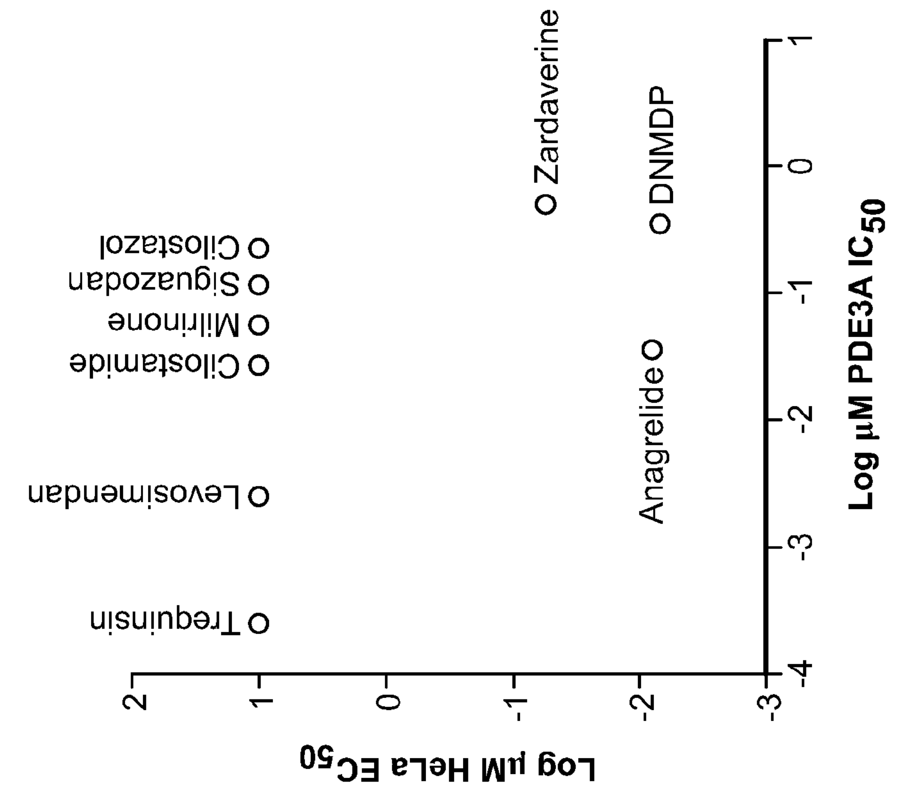
Figure 7A:
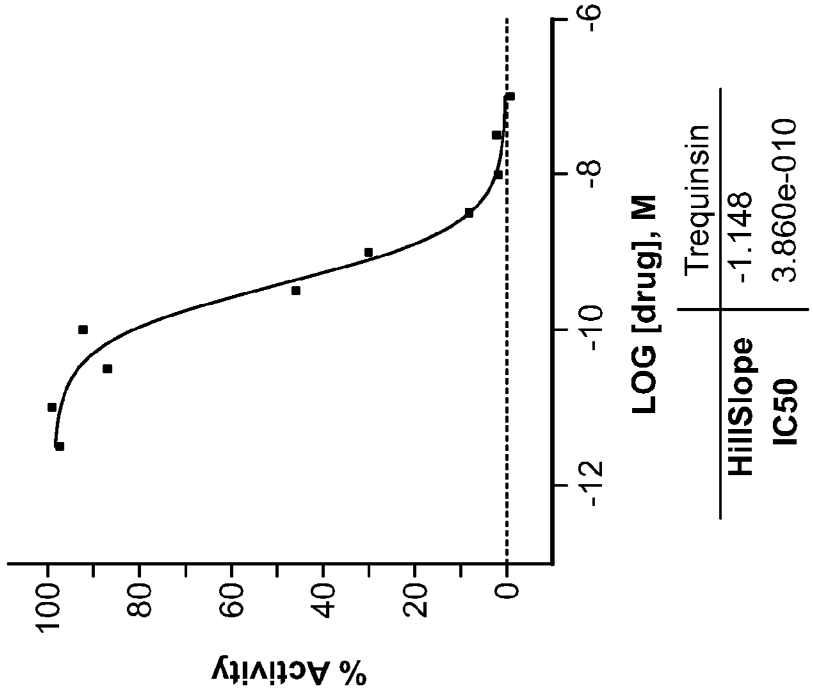
FIGS. 7A and 7B are graphs showing determination of Phosphodiesterase 3A (PDE3A) in vitro $IC_{50}$ of 6-(4-(diethylamino)-3-nitrophenyl)-5-methyl-4,5-dihydropyridazin-3(2H)-one (DNMDP).
Figure 7B:
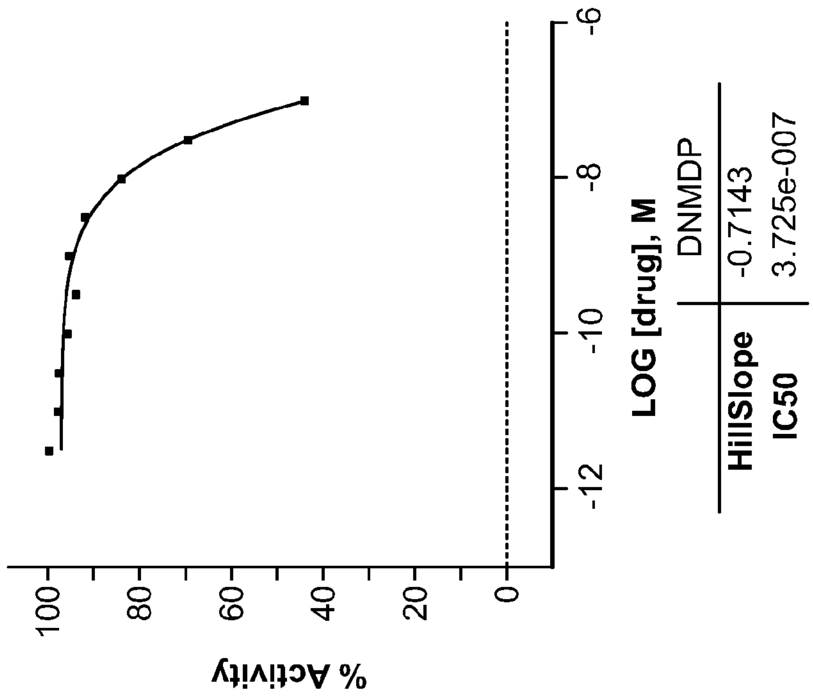
Figure 8A:
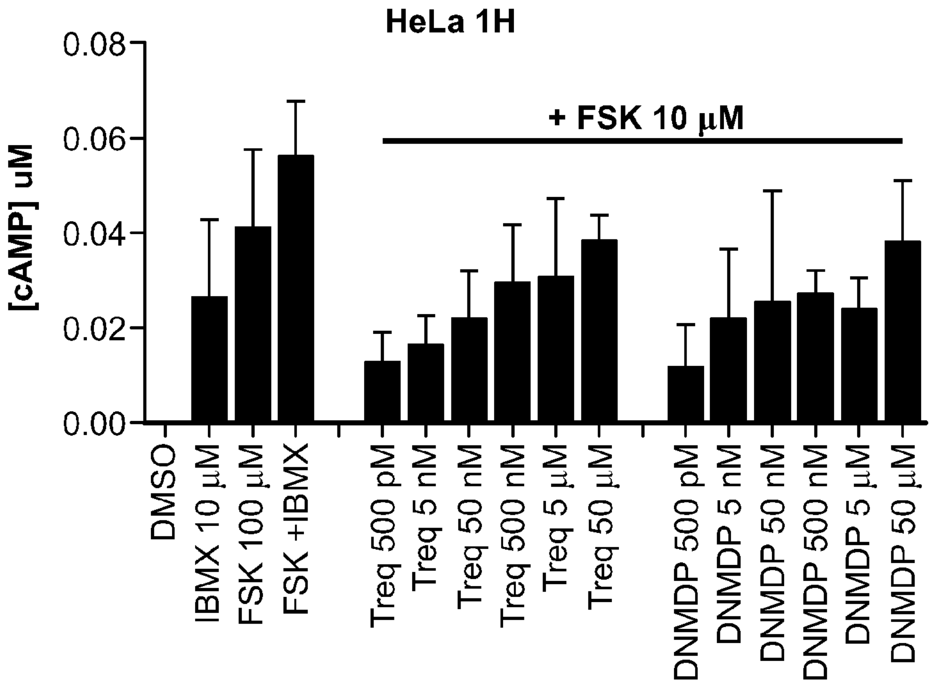
FIGS. 8A and 8B are graphs showing that induction of cAMP signaling did not phenocopy cytotoxicity induced by 6-(4-(diethylamino)-3-nitrophenyl)-5-methyl-4,5-dihydro-pyridazin-3(2H)-one (DNMDP). Forskolin: FSK.
Figure 8B:
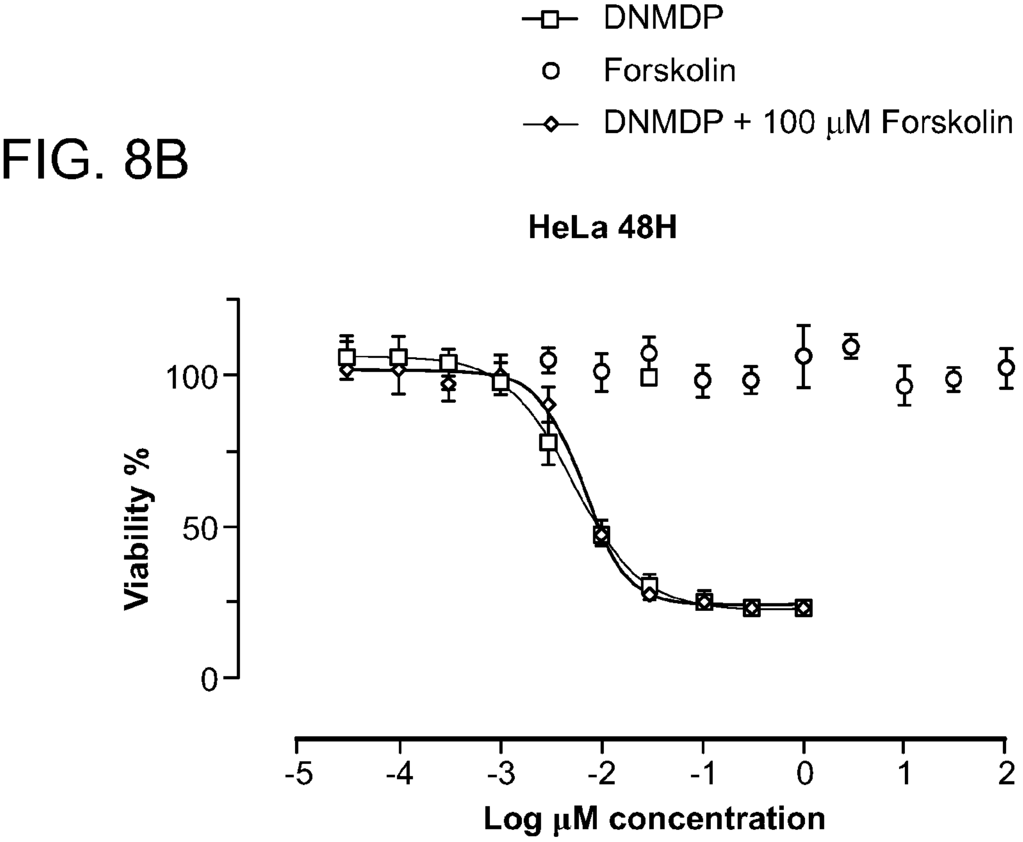

Because of the cellular correlation between PDE3A expression and DNMDP sensitivity, the in vitro inhibition of PDE3A and PDE3B by DNMDP, and the structural similarity of DNMDP to known PDE3 inhibitors, it was analyzed whether all PDE3 inhibitors would exhibit a similar cytotoxic profile to DNMDP. Surprisingly, there was almost no correlation between $IC_{50}$ for in vitro enzymatic PDE3A inhibition and HeLa cell cytotoxicity across a series of tested compounds (FIG. 5C and FIGS. 7A and 7B). Indeed, the potent PDE3 inhibitor trequinsin (PDE3 $IC_{50}$=0.25 nM, Ruppert et al., Life Sci. 31, 2037-2043, 1982) did not affect HeLa cell viability in any detectable way. Despite their differential effects on HeLa cell viability, the non-cytotoxic PDE3 inhibitor trequinsin and the potent cytotoxic compound DNMDP had similar effects on intracellular cAMP levels in forskolin-treated HeLa cells (FIGS. 8A and 8B). This result indicates that inhibition of the cAMP and cGMP hydrolysis functions of PDE3A was not sufficient for the cytotoxic activity of DNMDP.

TABLE 2

Results of phosphodiesterase inhibition reactions

| PDE | % inh. #1 | % inh. #2 | % inhibition |
|---|---|---|---|
| PDE1A1 | 3 | 7 | 5 |
| PDE1B | −5 | 0 | −2 |
| PDE1C | 2 | 9 | 5 |
| PDE2A | 6 | 10 | 8 |
| PDE3A | 95 | 95 | 95 |
| PDE3B | 98 | 97 | 97 |
| PDE4A1A | 14 | 18 | 16 |
| PDE4B1 | 21 | 20 | 21 |
| PDE4C1 | 10 | 14 | 12 |
| PDE4D3 | 14 | 16 | 15 |
| PDE4D7 | 19 | 20 | 20 |
| PDE5A1 | 16 | 16 | 16 |
| PDE7A | 24 | 20 | 22 |
| PDE7B | 5 | 11 | 8 |
| PDE8A1 | 10 | 12 | 11 |
| PDE9A2 | 0 | 5 | 2 |
| PDE10A1 | 61 | 65 | 63 |
| PDE10A2 | 67 | 70 | 68 |
| PDE11A | 14 | 18 | 16 |

Example 3. Target Validation of PDE3A

The complex relationship between phosphodiesterase 3A (PDE3A) inhibition and cell killing, in which 6-(4-(diethylamino)-3-nitrophenyl)-5-methyl-4,5-dihydropyridazin-3(2H)-one (DNMDP) and some PDE3 inhibitors kill HeLa and other DNMDP-sensitive cells, whereas others PDE3 inhibitors do not affect cell viability, indicated several possible interpretations including: 1) the cytotoxic activity might be PDE3-independent and due to action on a different protein though screening 234 kinases found no kinase inhibition by 10 μM DNMDP; 2) cytotoxic and non-cytotoxic PDE3 inhibitors might bind to different sites within the protein and exert distinct activities; or 3) the cytotoxic and non-cytotoxic PDE3 inhibitors might bind to the PDE3 active sites but have different effects on the conformation and activity of the protein. This third possibility might be unexpected, but allosteric modulators of PDE4 have been shown to bind the PDE4 active site and interact with upstream (UCR2), and downstream (CR3) regulatory domains and thereby stabilize specific inactive conformations (Burgin et al., Nat Biotechnol 28, 63-70, 2010). Most importantly, PDE4 competitive inhibitors and PDE4 allosteric modulators with similar $IC_{50}$s for cAMP hydrolysis in vitro had different cellular activities and safety profiles in animal studies (Burgin et al., Nat Biotechnol 28, 63-70, 2010). To evaluate whether PDE inhibitors or other small molecules compete with DNMDP, the PHARMAKON 1600 collection of 1600 bioactive compounds (PHARMAKON 1600 is a unique collection of 1600 known drugs from US and International Pharmacopeia) was screened to identify compounds that were able to rescue cell death induced by DNMDP. HeLa cells were co-treated with 30 nM DNMDP (the $EC_{70}$ concentration) and 20 μM of each bioactive compound. Cell viability after 48-hour treatment was assessed by ATP consumption as described earlier. The five most potent compounds that rescued cell death induced by DNMDP were all PDE inhibitors, and the three most potent compounds, levosimendan, milrinone, and cilostazol, were all selective PDE3 inhibitors (FIG. 9A).

Figures 9A, 9B, 9C:
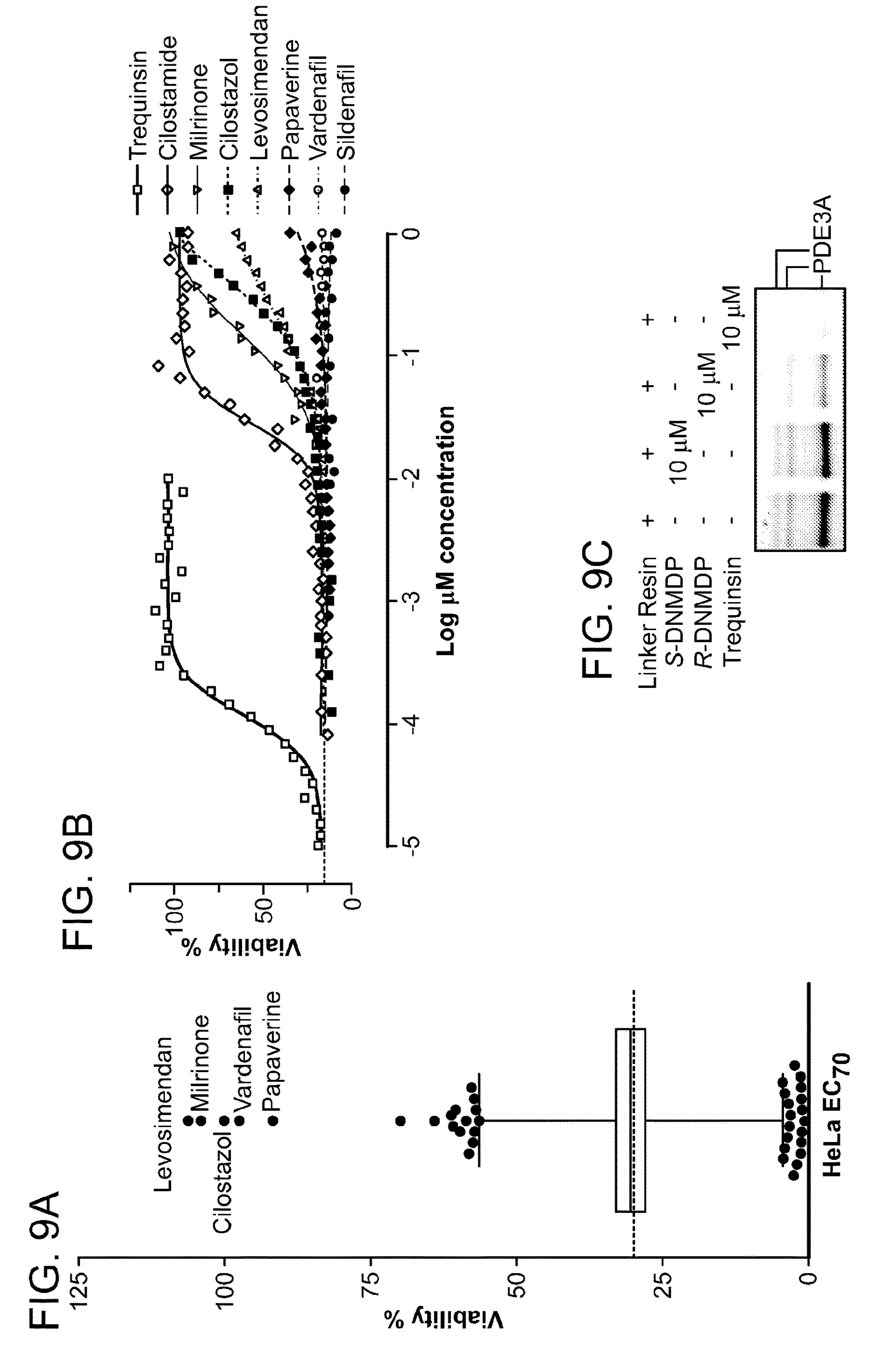
FIGS. 9A-9C show that non-lethal Phosphodiesterase 3 (PDE3) inhibitors rescued cell death induced by 6-(4-(diethylamino)-3-nitrophenyl)-5-methyl-4,5-dihydro-pyridazin-3(2H)-one (DNMDP) by competing for the binding of PDE3A.

In follow-up experiments, it was confirmed that cilostamide, levosimendan, milrinone, and several other non-cytotoxic selective PDE3 inhibitors were able to rescue DNMDP cytotoxicity in a dose-dependent manner (FIG. 9B). The most potent DNMDP competitor was trequinsin, with an "$RC_{50}$" (the concentration at which it achieved 50% rescue) of <1 nM; in contrast, PDE5 inhibitors such as sildenafil and vardenafil, as well as the pan-PDE inhibitors idubulast and dipyridamole, were not effective competitors up to 10 μM concentrations in this assay (FIG. 9B). This indicated that non-cytotoxic PDE3 inhibitors and DNMDP compete for binding to the same molecular target that is mediating the cytotoxic phenotype.

Figure 10A:
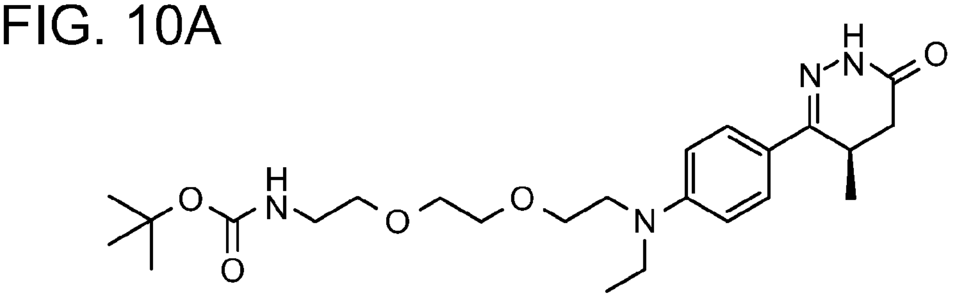
FIGS. 10A and 10B show the structure and rescue phenotype of linker-compound tert-butyl (R)-(2-(2-(2-(ethyl(4-(4-methyl-6-oxo-1,4,5,6-tetrahydropyridazin-3-yl)phenyl)amino)ethoxy) ethoxy)ethyl)carbamate (DNMDP)-2L.
Figure 10B:
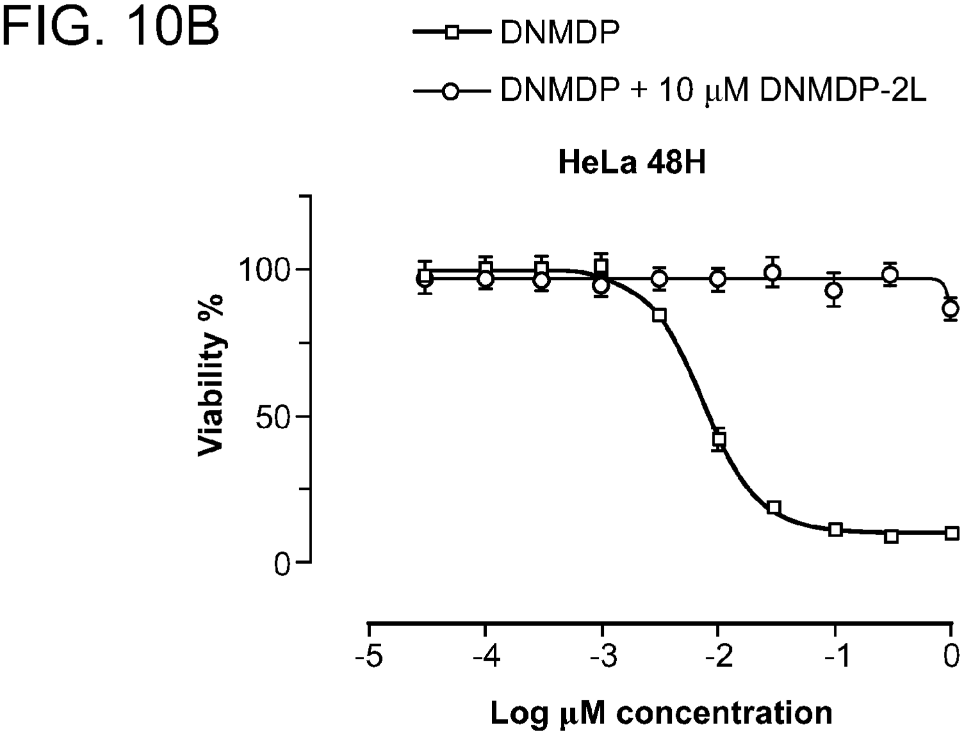

To identify the molecular target of DNMDP, an affinity purification was performed using an (R)-des-nitro-DNMDP solid-phase tethered linker analogue (FIG. 10A) incubated with HeLa cell lysate. This linker analogue had the same DNMDP cytotoxicity rescue phenotype as non-cytotoxic PDE3 inhibitors described above (FIG. 10B), indicating that it too bound to the same molecular target. It was competed for the molecular target by adding either an excess of trequinsin or separate enantiomers of DNMDP, where only the (R)-enantiomer was cytotoxic. Immunoblotting for PDE3A of the affinity purified material showed that PDE3A indeed binds to the linker analogue. Binding of PDE3A to the linker analogue was blocked by both trequinsin and (R)-DNMDP, but not by the non-cytotoxic enantiomer (S)-DNMDP (FIG. 9C). Thus both trequinsin and (R)-DNMDP prevented the binding of PDE3A to the tethered DNMDP analogue, and it was concluded that both molecules bind PDE3A directly.

Figure 11A:
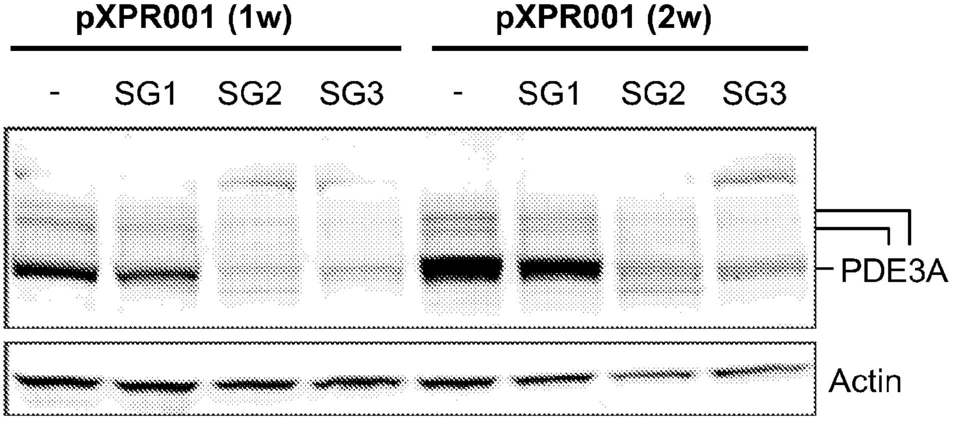
FIGS. 11A-11C show that Phosphodiesterase 3A (PDE3A) was not essential in sensitive cell lines, but was required for relaying the cytotoxic signal.
Figure 11B:
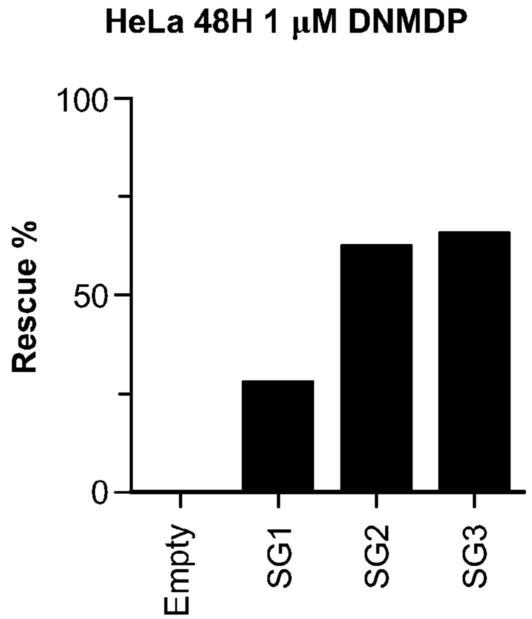
Figure 11C:
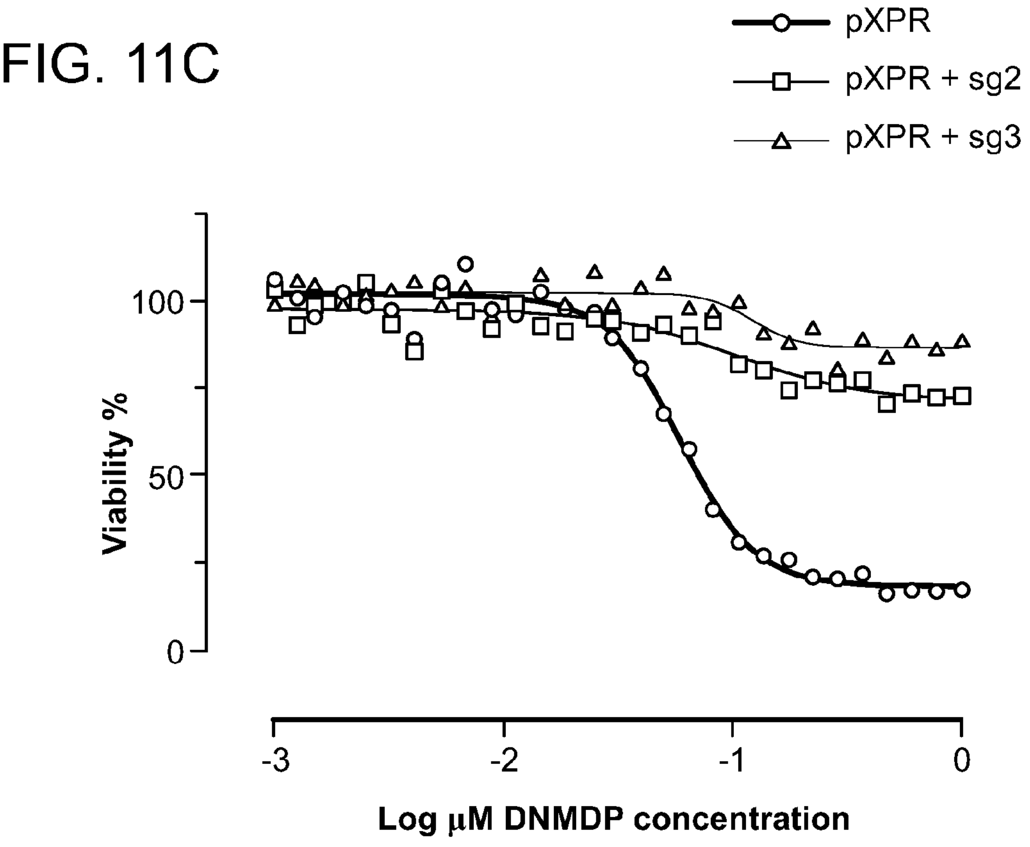
Figure 12A:
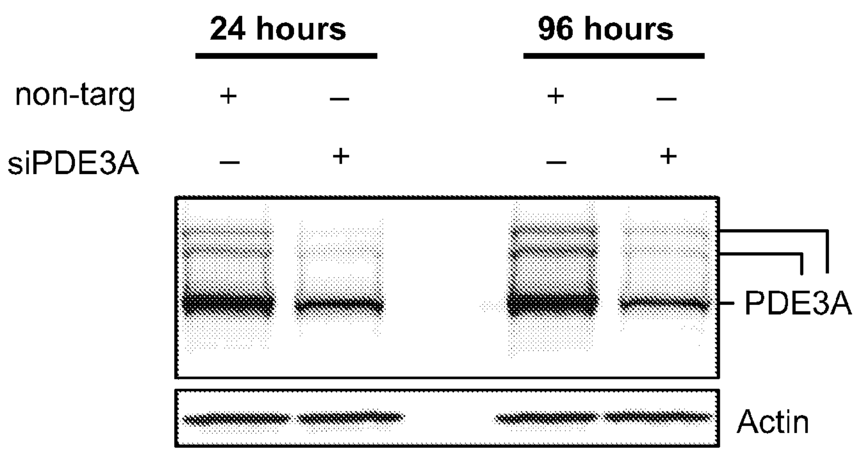
FIGS. 12A and 12B are a Western blot and a graph showing that reduction of Phosphodiesterase 3A (PDE3A) protein level caused resistance to 6-(4-(diethylamino)-3-nitrophenyl)-5-methyl-4,5-dihydropyridazin-3(2H)-one (DNMDP).
Figure 12B:
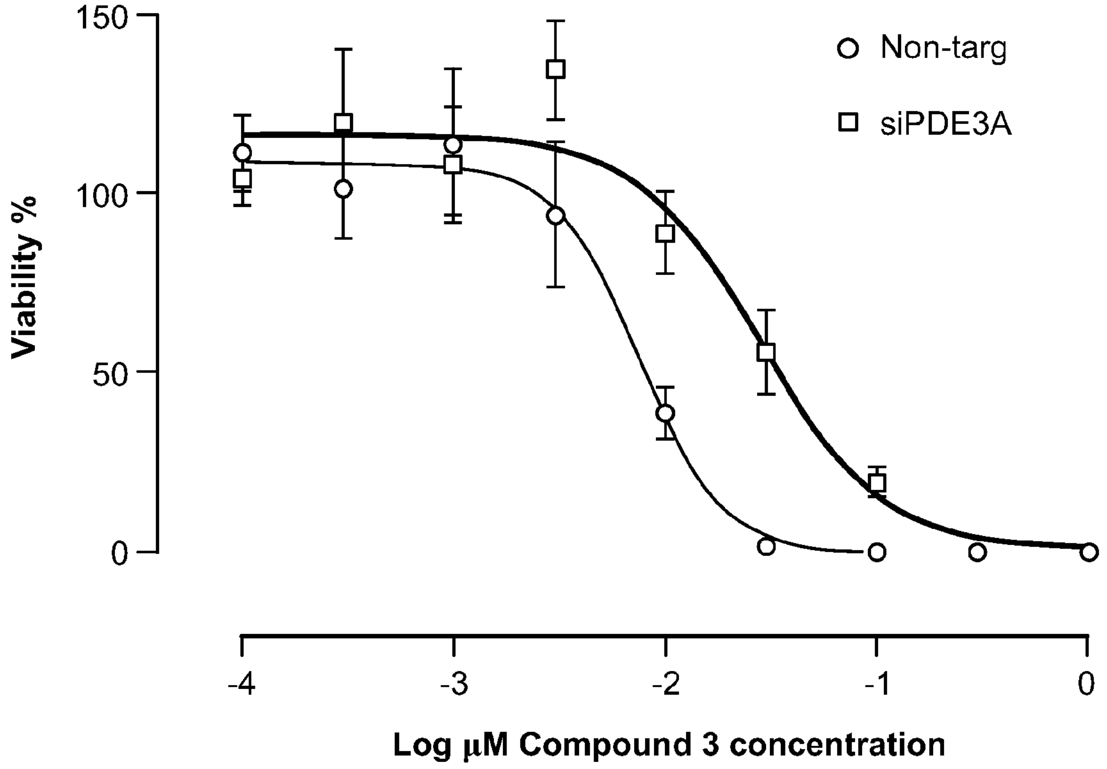

Based on the observations that DNMDP-sensitive cells expressed high levels of PDE3A, and that DNMDP competed with non-cytotoxic inhibitors for PDE3A binding, it was hypothesized that DNMDP mediated its cytotoxic phenotype through the interaction with PDE3A and that PDE3A abundance was a direct cellular determinant of DNMDP sensitivity. To validate this hypothesis, the effect of reducing levels of PDE3A on the response to DNMDP was tested. A clustered regularly interspaced short palindromic (CRISPR)-associated CAS9 enzyme that was targeted with three guide RNAs (sgRNA) targeting three different sites in the PDE3A locus led to complete loss of PDE3A expression (Cong et al., Science 339, 819-823, 2013) sgRNA2 and sgRNA3 almost completely reduced PDE3A protein levels, whereas sgRNA1 had a moderate effect on PDE3A expression (FIG. 11A). Importantly, both sgRNA2 and sgRNA3 led to significant rescue of toxicity by an active cytotoxic DNMDP analog, 3 (FIGS. 11A and 11B and FIGS. 5A-5C). Both sgRNA2 and sgRNA3 led to significant rescue of toxicity by DNMDP (FIG. 11C). Changes in proliferation rate or morphology in HeLa cells with reduced PDE3A expression were not observed, indicating that PDE3A was not required for cell survival. In an independent approach using an siRNA smart-pool containing four different siRNAs targeting PDE3A, PDE3A expression was reduced in HeLa cell line with a maximum efficiency of 70% between 24 and 72 hours after transfection. HeLa cells treated with siPDE3A had a higher $EC_{50}$ to a DNMDP analog compared to the control siRNA condition (FIGS. 12A and 12B). Without being bound by theory it was concluded that DNMDP cytotoxicity requires PDE3A, and that DNMDP likely modulates the function of PDE3A.

Example 4. Determining the Mechanism of Action of DNMDP

Figure 13A:
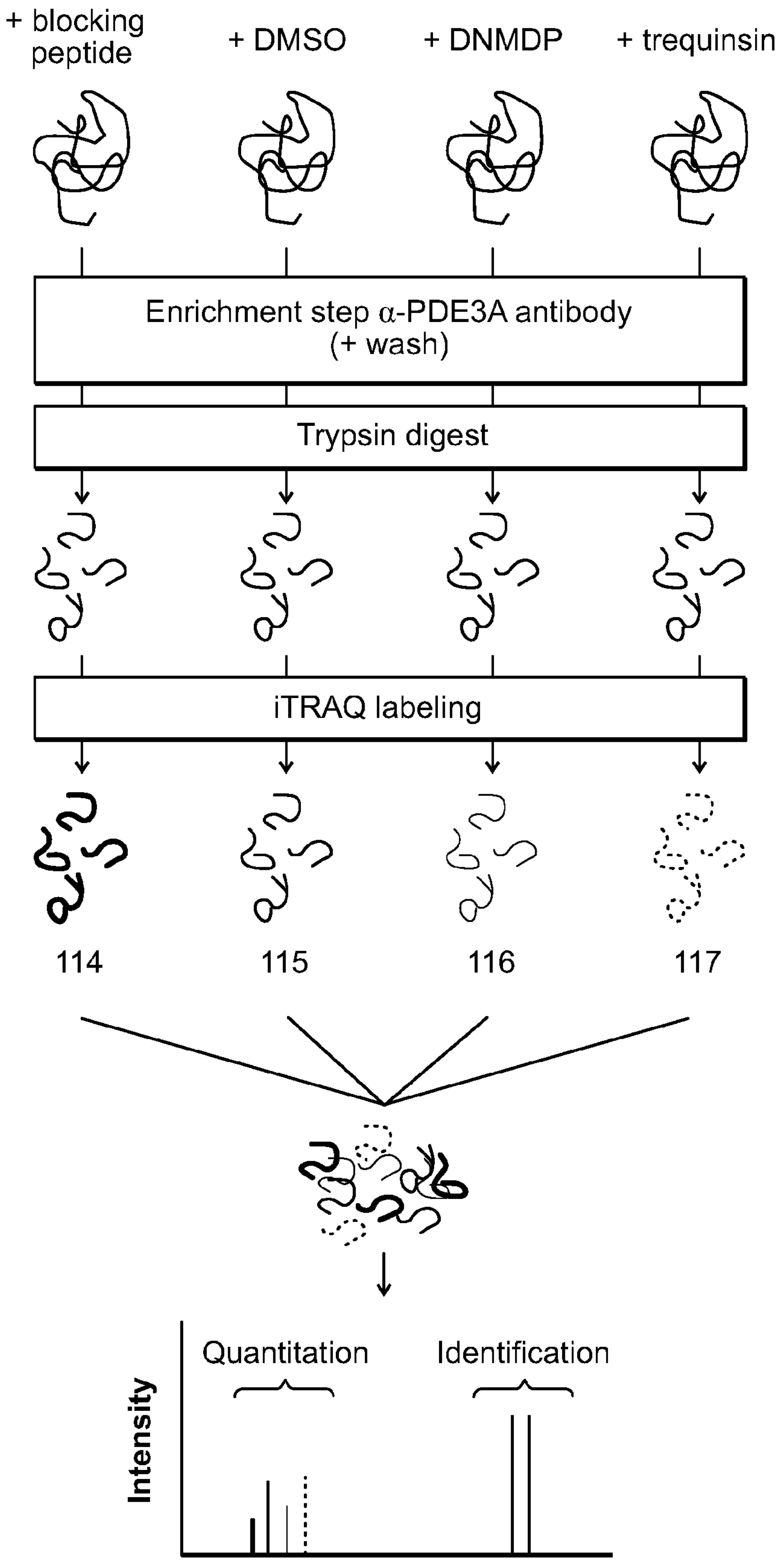
FIGS. 13A-13C show that Phosphodiesterase 3A (PDE3A) immunoprecipitation in the presence of 6-(4-(diethylamino)-3-nitrophenyl)-5-methyl-4,5-dihydro-pyridazin-3(2H)-one (DNMDP) revealed novel SIRT7 and SLFN12 interaction.
Figure 13B:
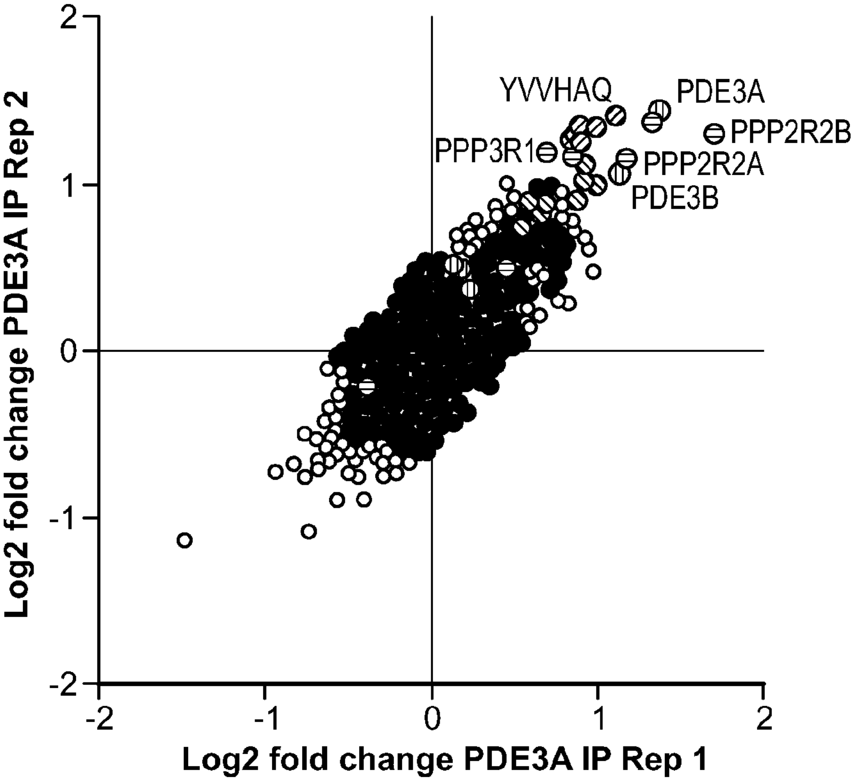
Figure 14A:
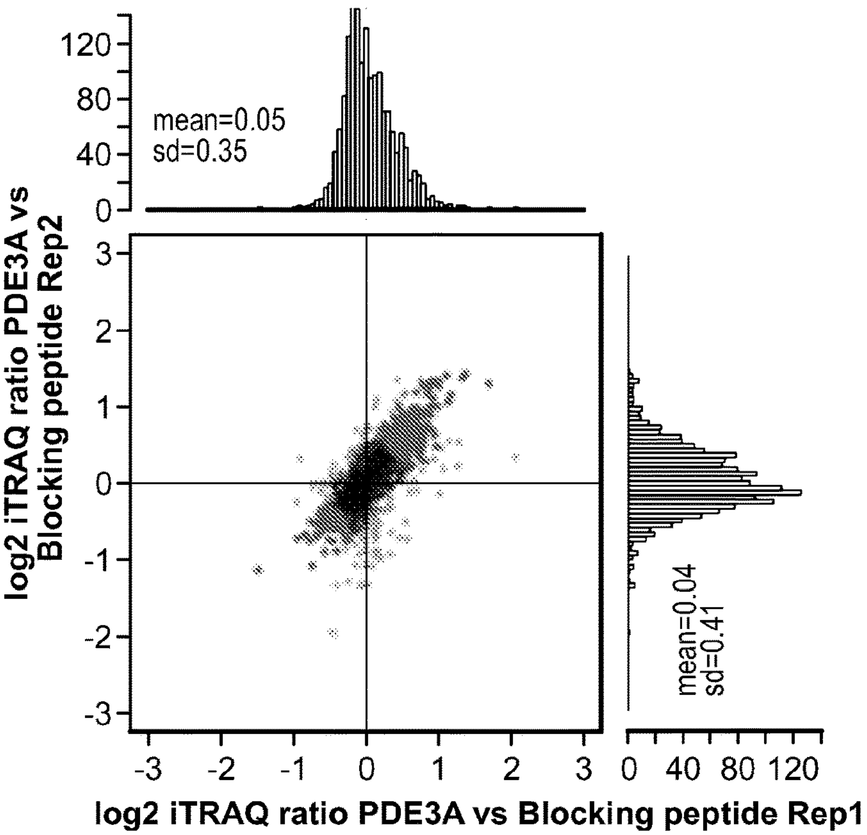
FIGS. 14A-14C show results of replicate PDE3A-protein interaction studies using PDE3A as bait under different conditions. Each scatterplot showed $log_2$ ratios of two replicates for proteins that were enriched by PDE3A under different conditions over enrichment by PDE3A in the presence of blocking peptide. Each dot represents the $log_2$ ratio for that particular protein, medium gray dots correspond to a Benjamini-Hochberg adjusted p value <0.01, light gray dots represent proteins that fall outside of the Blandt-Altman test for reproducibility within a 95% confidence interval.

The dependence of 6-(4-(diethylamino)-3-nitrophenyl)-5-methyl-4,5-dihydropyridazin-3(2H)-one (DNMDP) cytotoxicity on phosphodiesterase 3A (PDE3A) protein abundance indicated a possible mechanism similar to that recently observed for lenalidomide, which acts by a neomorphic or hypermorphic mechanism by stabilizing an interaction between cereblon and IKAROS Family Zinc Finger 1 (IKZF1) and IKZF3 (Krönke et al., Science 343, 301-305, 2014; Lu et al., Science 343, 305-309, 2014). In addition, PDE4 allosteric modulators, but not competitive inhibitors, have been shown to bind and stabilize a "closed" protein conformation that has independently been shown to uniquely bind the PDE4-partner protein DISC1 (Millar et al., Science 310, 1187-1191, 2005). The protein complexes in which PDE3A resides were characterized under normal conditions, and it was examined how these complexes change when PDE3A is bound to DNMDP or the non-cytotoxic PDE3 inhibitor trequinsin. PDE3A and interacting proteins from Hela cells were immunoprecipitated in the presence of DNMDP and trequinsin followed by labeling with isobaric stable isotope tags for relative abundance and quantitation by mass spectrometry (iTRAQ/MS, FIG. 13A). PDE3A immunoprecipitates from HeLa cells were enriched for multiple protein phosphatase subunits including protein phosphatase 2 subunits (PPP2CA, PPP2R1A, PPP2R1B, PPP2R2A, PPP2R2D), calcineurin (PPP3R1, PPP3CA, Beca et al., Circ. Res. 112, 289-297, 2013), 14-3-3 (YWHAB, YWHAQ, YWHAG, YWHAZ, Pozuelo Rubio et al., Biochem. J. 392, 163-172, 2005), and tubulin (TUBA1C, TUBA1B) family members (FIG. 13B and FIG. 14A). In addition, it was found that PDE3A and PDE3B reside in the same protein complex, which has been previously reported (Malovannaya et al., Cell 145, 787-799, 2011).

Figure 13C:
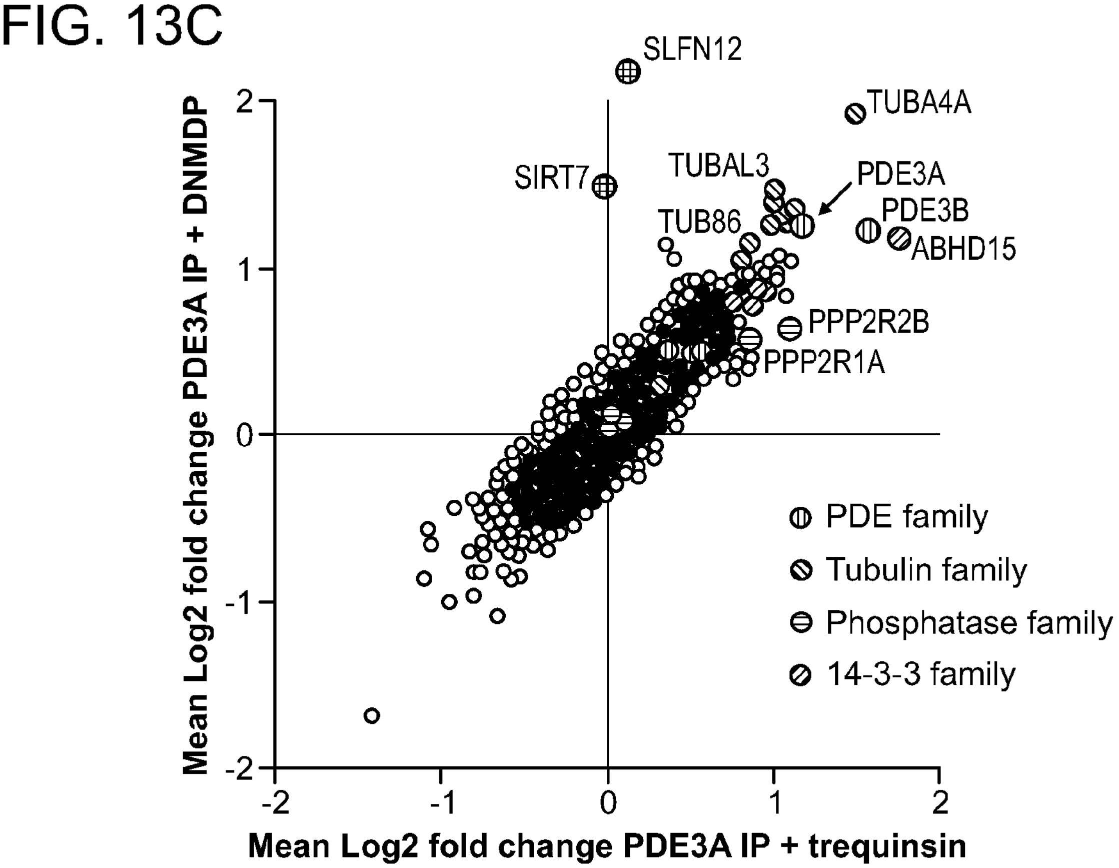
Figure 14B:
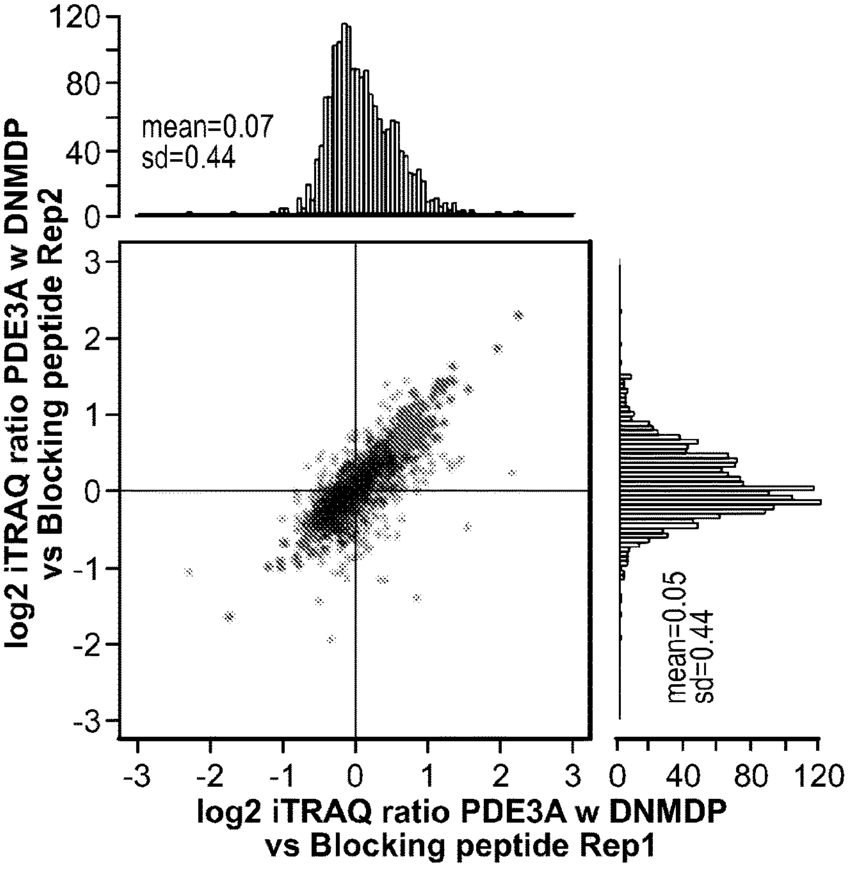
Figure 14C:
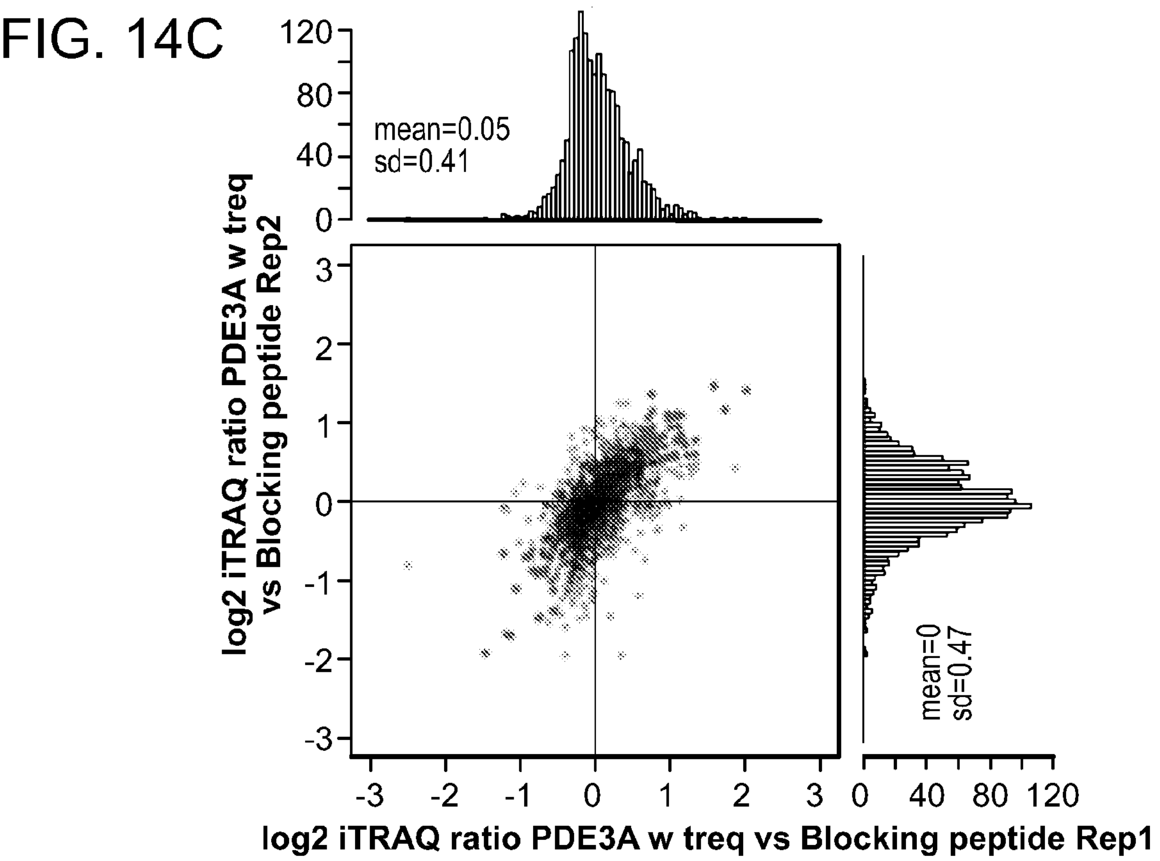
Figure 19:
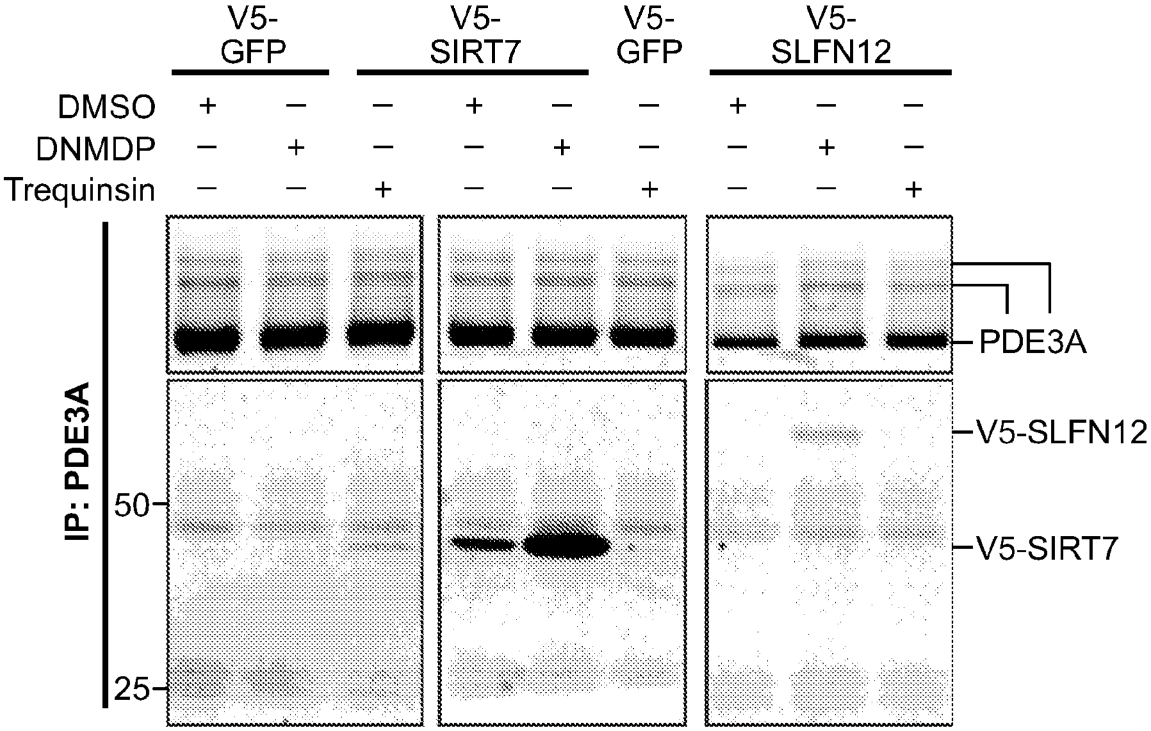
FIG. 19 is an immunoblot showing that DNMDP induces interaction between PDE3A and SIRT7 and SLFN12 in HeLa cells. HeLa cells were transfected with indicated plasmids and treated with indicated compounds with a final concentration of 10 μM for four hours. Endogenous PDE3A was immunoprecipitated and immunoblotted for V5 to identify novel interaction with SIRT7 and SLFN12 (upper two panels). Immunoprecipitate input was immunoblotted for PDE3A and V5 (lower two panels). V5-SLFN12 was undetectable in whole cell lysate.
Figure 20:
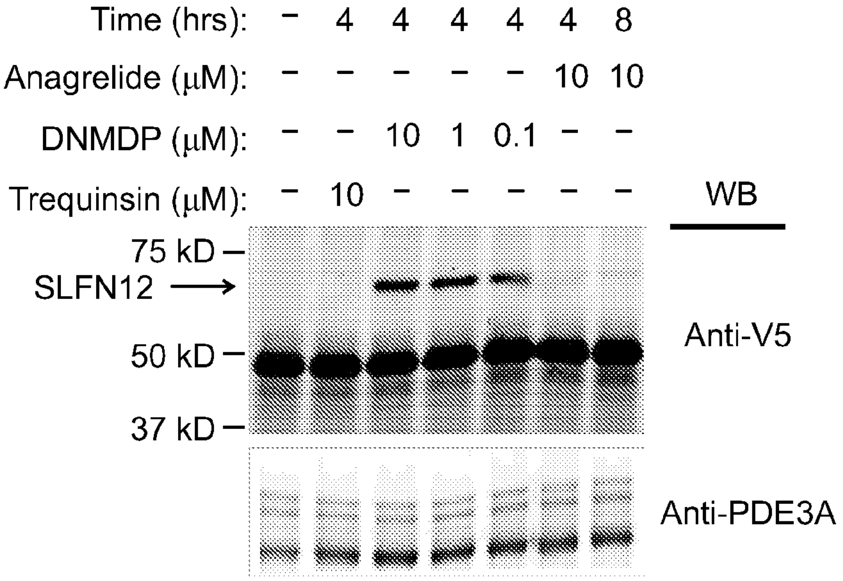
FIG. 20 is an immunoblot showing confirmation of mass spectrometric results herein using affinity reagents.

Binding of DNMDP altered the composition of interacting proteins that were co-immunoprecipitated with PDE3A. Proteins that were specifically enriched in PDE3A immunoprecipitates after treatment with DNMDP included Sirtuin 7 (SIRT7) and Schlafen 12 (SLFN12) (FIG. 13C and FIG. 14B). These proteins specifically interacted with PDE3A in the presence of DNMDP, and were not observed in the trequinsin treated control, whereas a known PDE3B interactor, abhydrolase domain-containing protein 15 (ABHD15, Chavez et al., Biochem. Biophys. Res. Commun. 342, 1218-1222, 2006), was enriched in the immunoprecipitate from trequinsin-treated cells (FIG. 13C and FIG. 14C). The interaction promoted by DNMDP between PDE3A and both SIRT7 and SLFN12 was validated with affinity reagents. Immunoprecipitation of endogenous PDE3A in HeLa cells treated with DNMDP, but not DMSO or trequinsin, enhanced complex formation of ectopically expressed V5-tagged SIRT7 and SLFN12 with PDE3A, as evidenced by coimmunoprecipitation (FIG. 19). FIG. 20 further shows that DNMDP and (weakly) anagrelide, but not trequinsin, induced PDE3A and SFLN12 complex formation.

Similar to PDE3A, overexpression of SLFN12 appears to have a cytotoxic effect in DNMDP sensitive cell lines, contributing to the difficulty of detecting SLFN12 in whole cell lysates.

Figure 15A:
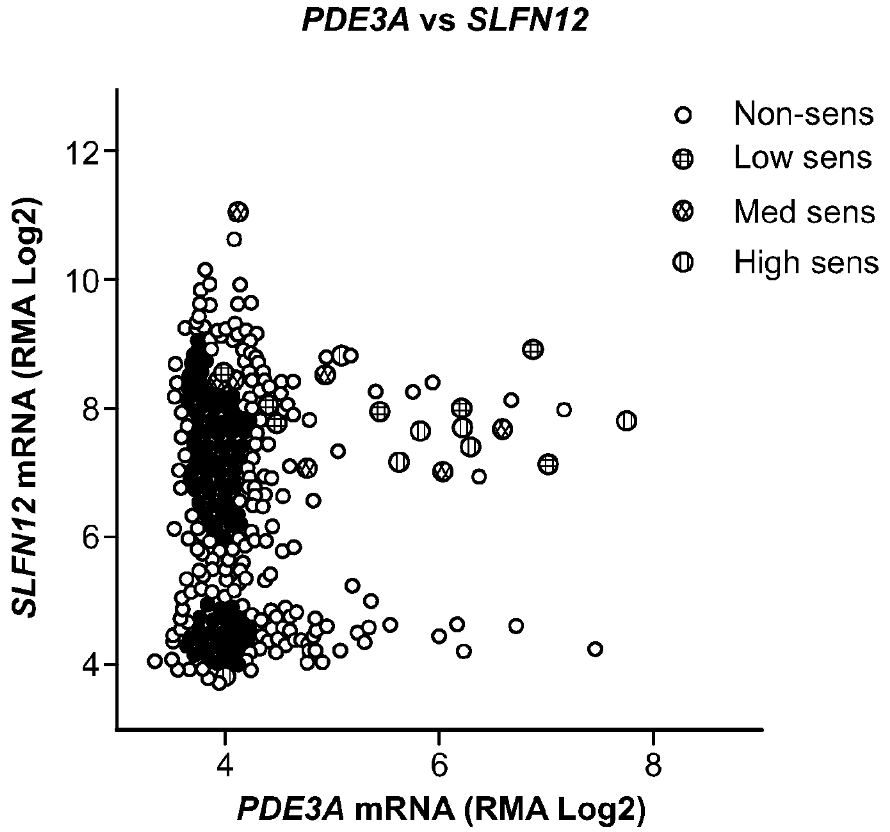
FIGS. 15A-15E show that cell lines with dual expression of SLFN12 and PDE3A were significantly enriched for DNMDP-sensitive cell lines.
Figure 15B:
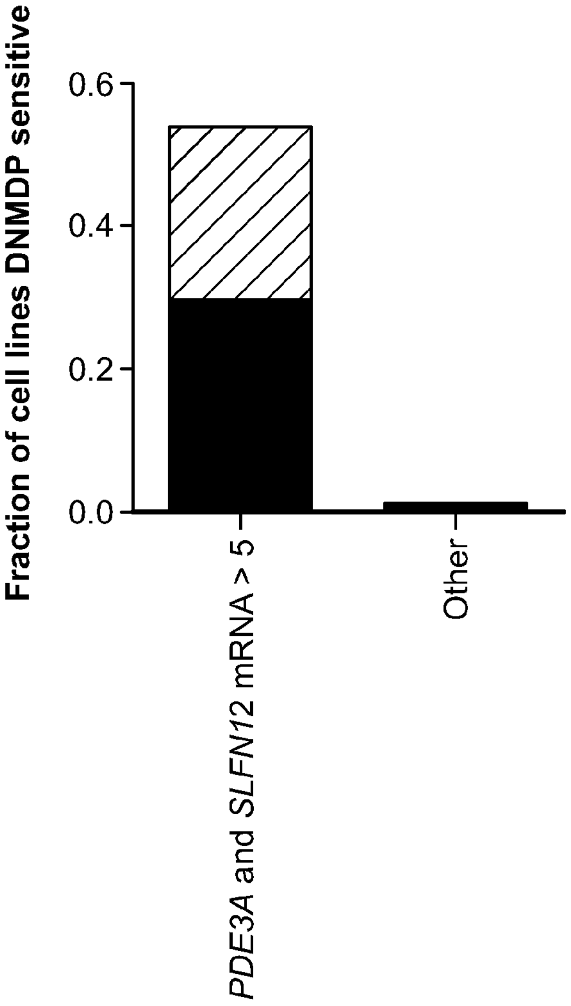
Figure 15C:
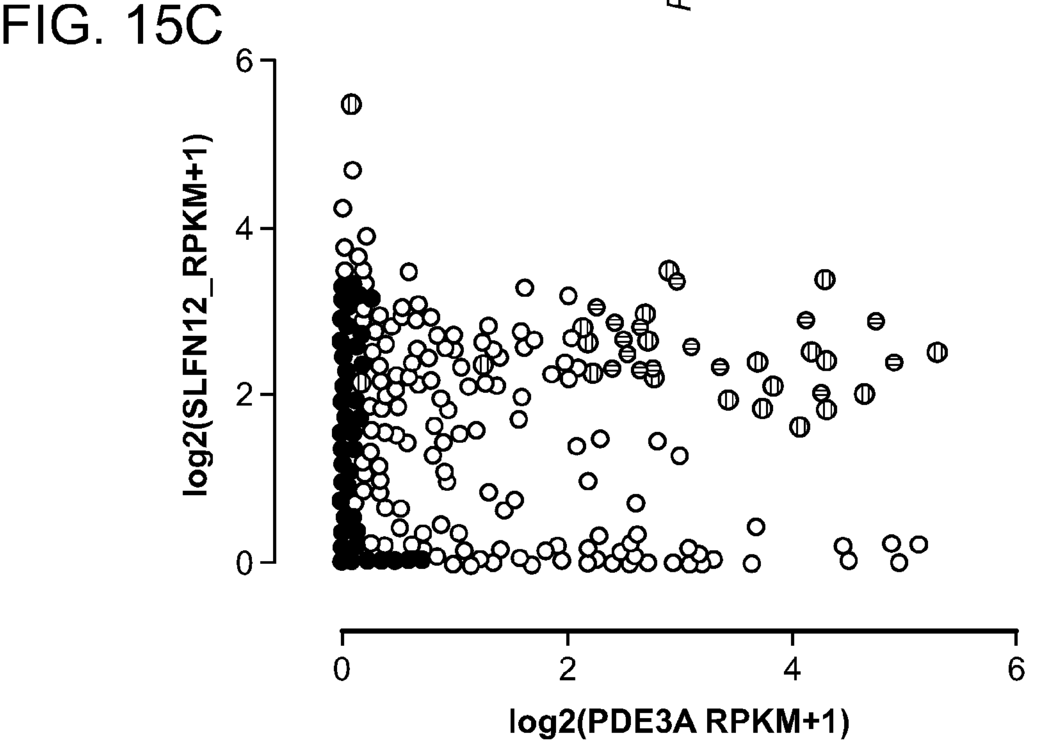
Figure 15D:
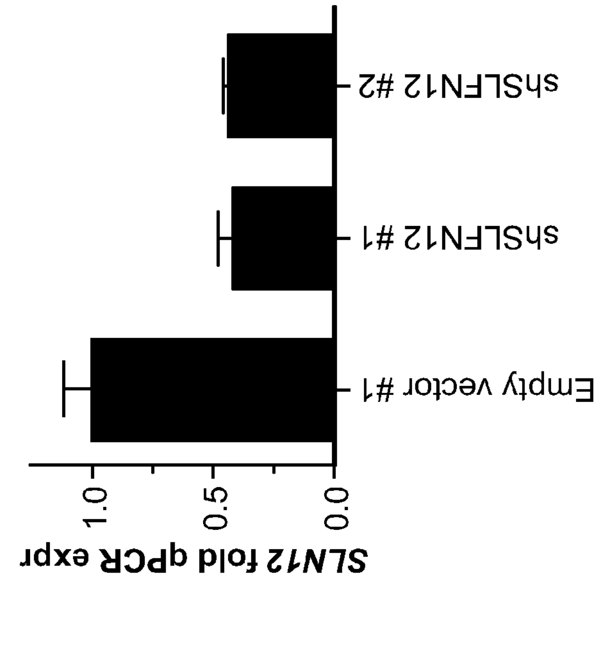
Figure 15E:
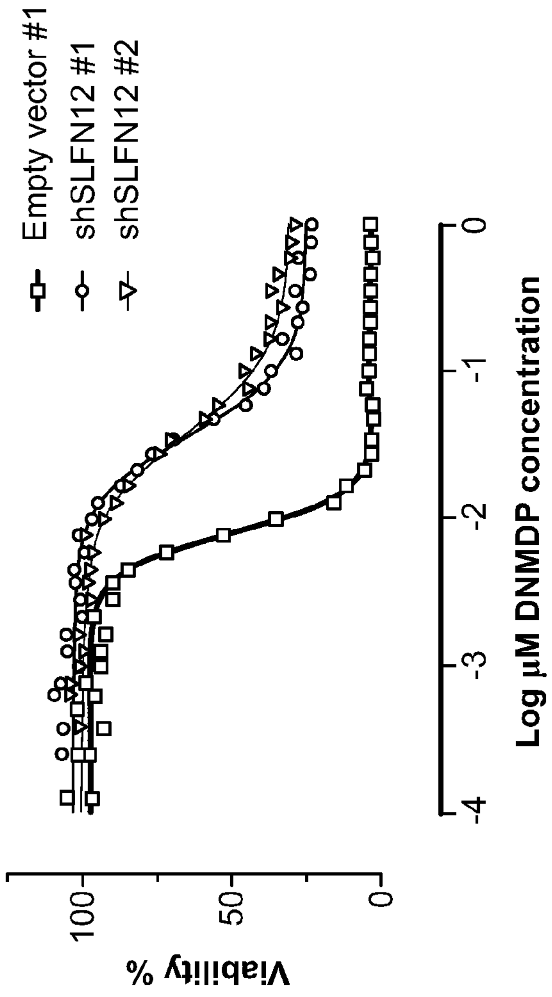
Figure 16A:
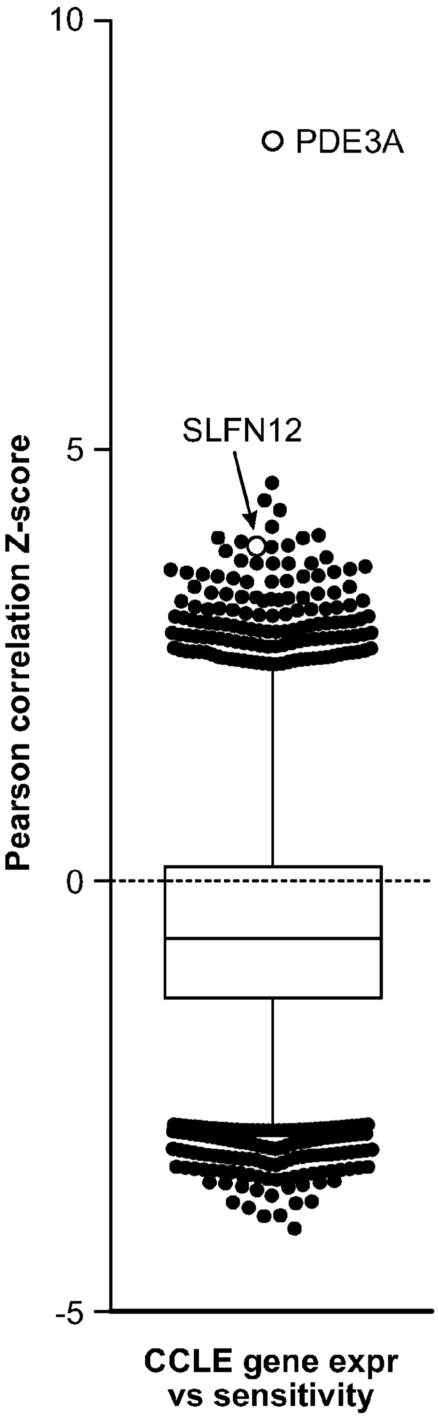
FIGS. 16A and 16B are scatter plots showing that SLFN12 expression was amongst the top genes correlating with DNMDP sensitivity.
Figure 16B:
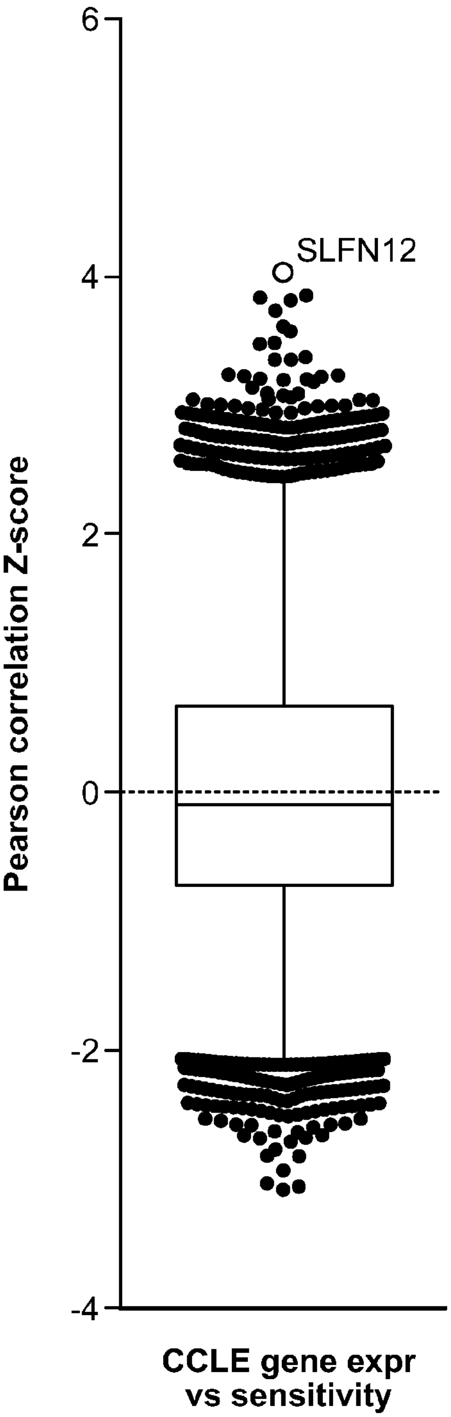

The enhanced interaction of PDE3A with SIRT7 and SLFN12 indicated the possibility that one or more of these interacting proteins might contribute to DNMDP sensitivity. SIRT7 mRNA expression was relatively constant among all cells tested, but the co-expression of SLFN12 and PDE3A mRNA showed a strong correlation with DNMDP sensitivity; almost all DNMDP-sensitive cell lines expressed high levels of SLFN12 (FIG. 15A-15C). Importantly, almost half of sensitive cell lines expressing high levels of SLFN12 and PDE3A were found to be melanoma cell lines (FIG. 15B). SLFN12 expression alone was also one of the top genes correlating with sensitivity to DNMDP, corroborating the hypothesis that SLFN12 could be functionally involved in DNMDP-induced cytotoxicity (FIG. 16A). Moreover, when correcting for PDE3A expression, SLFN12 expression was the top correlating gene with DNMDP sensitivity (FIG. 16B). To assess whether SLFN12 is required for the cytotoxic phenotype of DMNDP, we reduced SLFN12 mRNA expression by 60% by knockdown with two shRNAs in HeLa cells (FIG. 15D). Similar to reduction in PDE3A expression, reduction of SLFN12 expression did not result in cytotoxicity, and in fact decreased sensitivity to DNMDP (FIG. 15E). These results show that SLFN12, like PDE3A, is required for the cytotoxic phenotype of DMNDP. Characterization of normal expression of SLFN12 and PDE3A by the GTEX consortium (Pierson, E. et al. PLoS Comput. Biol. 11, e1004220 (2015)) shows low expression of SLFN12 in normal tissues, while high co-expression of both PDE3A and SLFN12 is rarely observed (Table 3). This could suggest that on-target toxicity of DNMDP and related compounds may be potentially limited.

TABLE 3

RPKM values of SLFN12 and PDE3A expression in multiple healthy tissue types

| | SLFN12 (RPKM) | | PDE3A (RPKM) | | |
|---|---|---|---|---|---|
| | Mean | SD | Mean | SD | n |
| Adipose - Subcutaneous | 2.14 | 0.70 | 4.76 | 2.03 | 128 |
| Adipose - Visceral (Omentum) | 2.43 | 1.03 | 4.26 | 1.94 | 31 |
| Adrenal Gland | 3.01 | 0.83 | 0.34 | 0.21 | 52 |
| Artery - Aorta | 2.10 | 0.71 | 16.15 | 5.12 | 82 |
| Artery - Coronary | 1.80 | 0.80 | 17.73 | 6.52 | 44 |
| Artery - Tibial | 1.09 | 0.49 | 22.97 | 6.35 | 137 |
| Bladder | 1.38 | 0.57 | 1.33 | 0.40 | 11 |
| Brain - Amygdala | 0.37 | 0.23 | 0.96 | 0.34 | 26 |
| Brain - Anterior cingulate cortex (BA24) | 0.28 | 0.16 | 0.77 | 0.45 | 22 |
| Brain - Caudate (basal ganglia) | 0.40 | 0.23 | 1.27 | 0.37 | 36 |
| Brain - Cerebellar Hemisphere | 0.11 | 0.07 | 2.73 | 1.49 | 29 |
| Brain - Cerebellum | 0.19 | 0.10 | 2.40 | 0.98 | 31 |
| Brain - Cortex | 0.25 | 0.12 | 0.56 | 0.59 | 25 |
| Brain - Frontal Cortex (BA9) | 0.26 | 0.15 | 0.54 | 0.33 | 28 |
| Brain - Hippocampus | 0.39 | 0.31 | 0.82 | 0.38 | 28 |
| Brain - Hypothalamus | 0.46 | 0.29 | 0.93 | 0.48 | 30 |
| Brain - Nucleus accumbens (basal ganglia) | 0.28 | 0.16 | 1.11 | 0.41 | 32 |
| Brain - Putamen (basal ganglia) | 0.29 | 0.18 | 0.91 | 0.33 | 24 |
| Brain - Spinal cord (cervical c-1) | 0.50 | 0.32 | 0.65 | 0.55 | 19 |
| Brain - Substantia nigra | 0.62 | 0.50 | 0.82 | 0.47 | 27 |
| Breast - Mammary Tissue | 2.48 | 0.74 | 3.19 | 2.35 | 66 |
| Cells - EBV-transformed lymphocytes | 4.70 | 1.57 | 0.02 | 0.01 | 54 |
| Cells - Transformed fibroblasts | 5.34 | 2.27 | 0.58 | 0.60 | 155 |
| Colon - Sigmoid | 1.58 | 0.50 | 10.27 | 3.45 | 13 |
| Colon - Transverse | 0.99 | 0.47 | 11.24 | 4.32 | 45 |
| Esophagus - Gastroesophageal Junction | 1.14 | 0.31 | 16.87 | 5.53 | 22 |
| Esophagus - Mucosa | 1.01 | 0.45 | 0.82 | 1.32 | 106 |
| Esophagus - Muscularis | 1.29 | 0.35 | 15.71 | 6.02 | 99 |
| Fallopian Tube | 2.32 | 0.86 | 3.80 | 1.86 | 6 |
| Heart - Atrial Appendage | 1.05 | 0.38 | 15.65 | 6.31 | 38 |
| Heart - Left Ventricle | 0.81 | 0.38 | 26.55 | 13.43 | 95 |
| Kidney - Cortex | 1.21 | 1.07 | 1.40 | 0.84 | 8 |
| Liver | 0.29 | 0.16 | 0.49 | 0.28 | 34 |
| Lung | 2.83 | 1.12 | 2.78 | 1.48 | 133 |
| Minor Salivary Gland | 1.75 | 0.61 | 0.62 | 0.44 | 5 |
| Muscle - Skeletal | 0.25 | 0.18 | 0.84 | 0.42 | 157 |
| Nerve - Tibial | 2.82 | 0.87 | 3.39 | 1.71 | 114 |
| Ovary | 1.92 | 0.57 | 2.17 | 1.13 | 35 |
| Pancreas | 0.52 | 0.27 | 2.65 | 0.86 | 65 |
| Pituitary | 0.47 | 0.23 | 1.04 | 0.47 | 22 |
| Prostate | 1.41 | 0.57 | 4.04 | 3.74 | 42 |
| Skin - Not Sun Exposed (Suprapubic) | 0.76 | 0.37 | 0.66 | 0.34 | 41 |
| Skin - Sun Exposed (Lower leg) | 0.63 | 0.31 | 1.00 | 0.69 | 126 |
| Small Intestine - Terminal Ileum | 1.61 | 0.72 | 7.34 | 4.83 | 17 |
| Spleen | 3.46 | 0.92 | 1.18 | 0.46 | 34 |
| Stomach | 1.10 | 0.40 | 3.93 | 5.35 | 81 |
| Testis | 0.49 | 0.19 | 0.43 | 0.20 | 60 |
| Thyroid | 3.19 | 0.96 | 2.59 | 1.34 | 120 |
| Uterus | 1.99 | 0.56 | 3.29 | 1.55 | 32 |
| Vagina | 1.39 | 1.39 | 2.49 | 2.49 | 34 |
| Whole Blood | 1.40 | 1.10 | 0.06 | 0.05 | 191 |

Figures 21, 22:
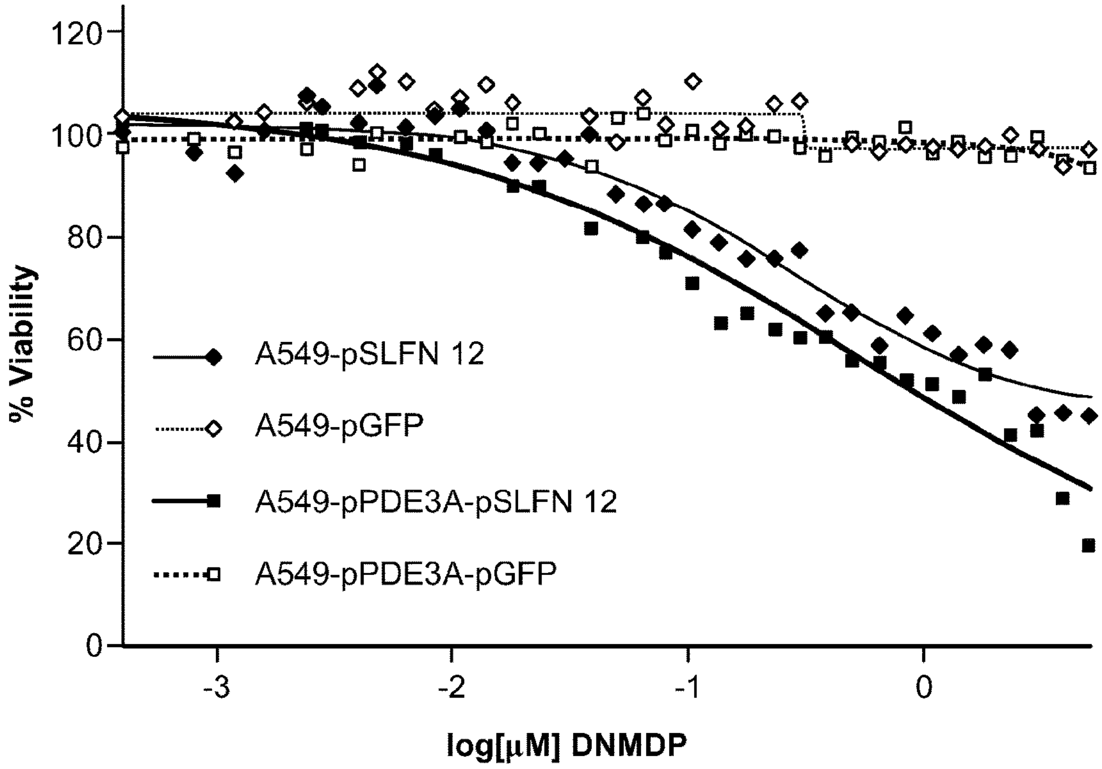
FIG. 21 is a set of tables showing that SLFN12 is lost in cells that have acquired resistance to DNMDP.
FIG. 22 is a plot showing sensitization of a DNMDP-resistant cell line by expression of SLFN12 or expression of SFLN12 and PDE3A.

FIG. 21 shows that SLFN12 is lost in cells that have acquired resistance to DNMDP. Cell lines initially sensitive to DNMDP were made resistant by persistent exposure to DNMDP and subsequently analyzed by RNA-seq. One gene was downregulated in both HeLa and H2122: SLFN 12.

Accordingly, a reduction in levels of SLFN 12 indicates that cells have become resistant to DNMDP and other PDE3A modulators.

FIG. 22 shows sensitization of a DNMDP-resistant cell line by expression of SLFN12 or expression of SFLN12 and PDE3A. Expression of SLFN12 was sufficient to confer DNMDP sensitivity to A549 cells. Adding PDE3A expression led to further sensitization.

Figure 23:
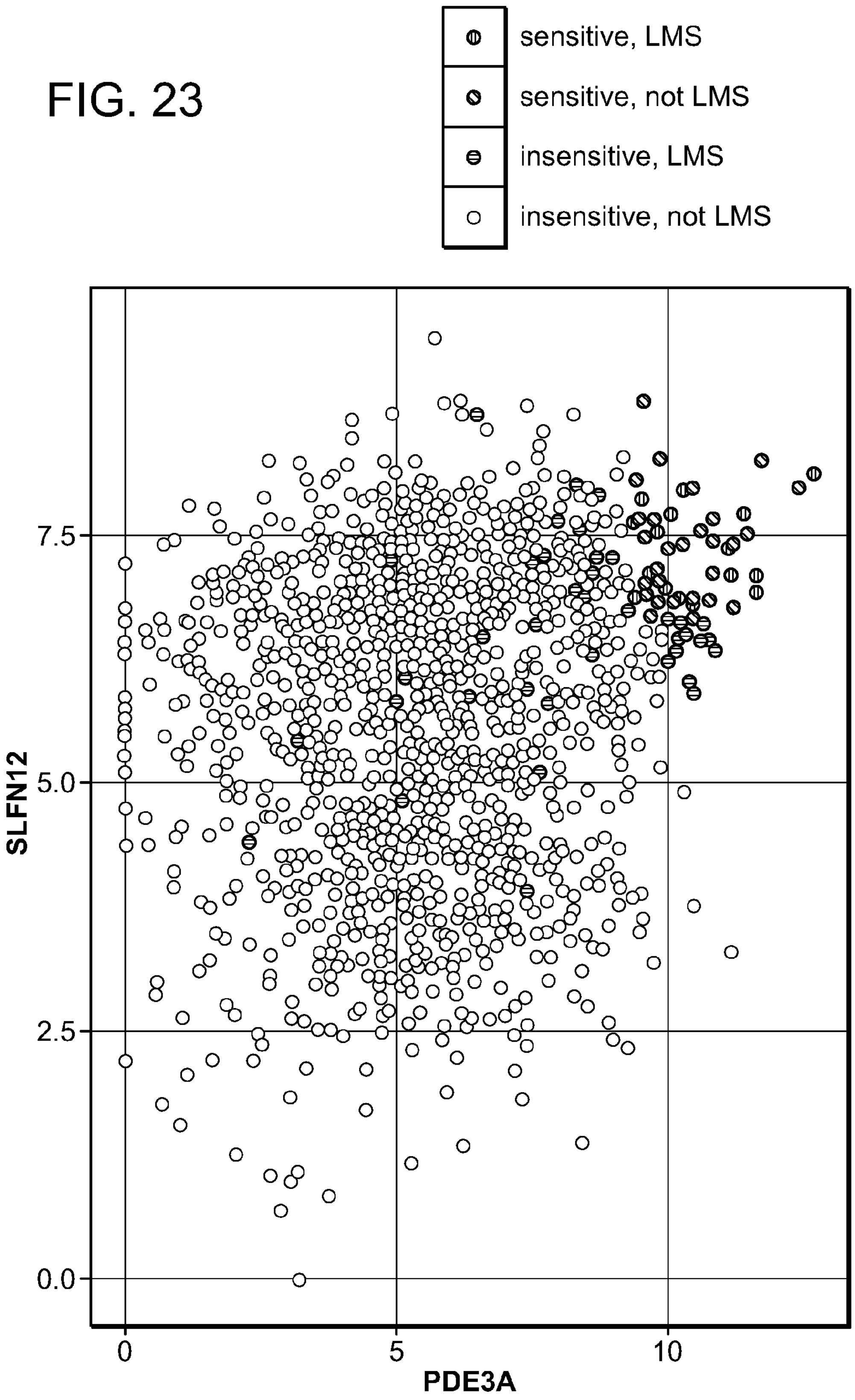
FIG. 23 is a scatter plot showing sensitivity of Leiomyosarcomas (LMS) to PDE3A modulation based on SLFN12 expression level.

Leiomyosarcomas are malignant smooth muscle tumors. Patient tumor samples from leiomyosarcomas were analyzed for PDE3A and SLFN12 expression to characterize sensitivity of leiomyosarcomas (LMS) to DNMDP. Leiomyosarcomas are thought to be sensitive to DNMDP due to prevalence among high purity TCGA samples expressing elevated levels of PDE3A and SLFN12 (FIG. 23, Table 4). P value for association of biomarker expression with leiomyosarcoma lineage: 0.0001.

TABLE 4

Leiomyosarcomas Characterization

| | Marker Expression Indicates DNMDP sensitive | Marker Expression Indicates DNMDP not sensitive |
|---|---|---|
| LMS | 17 | 31 |
| Not LMS | 38 | 1516 |

Differential scanning fluorimetry (DSF) was used to demonstrate binding of DNMDP to purified PDE3A catalytic domain, PDE3A(677-1141). In this experiment, 5 μM hsPDE3A(640-1141) was incubated in the absence or presence of 100 μM compounds, as indicated in Table 5. Binding buffer: 20 mM Hepes pH 7.4, 100 μM TCEP, 1 mM $MgCl_2$, 150 mM NaCl.

TABLE 5

Binding of DNMDP to PDE3A(677-1141)

| | $T_m$ (° C.) | $\Delta T_m$ (° C.) |
|---|---|---|
| $PDE3A_{677-1141}$ | 52.4 ± 0.0 | |
| $PDE3A_{677-1141}$ + DNMDP | 58.4 ± 0.0 | 6.0 |
| $PDE3A_{677-1141}$ + Anagrelide | 56.6 ± 0.0 | 4.2 |
| $PDE3A_{677-1141}$ + Trequinsin | 66.2 ± 0.0 | 14.2 |

Using chemogenomics, a class of compounds was discovered, exemplified by DNMDP, that targeted a novel cancer dependency by small-molecule modulation of PDE3A. These compounds bound PDE3A in a mutually exclusive manner with non-cytotoxic PDE3 inhibitors and exerted a neomorphic or hypermorphic effect on the function of PDE3A, leading to a change in its protein-protein interactions. One unique protein-interaction partner, SLFN12, was highly expressed in DNMDP-sensitive cell lines, indicating a functional role in the pathway through which the cytotoxic signal was relayed. As a result, DNMDP was both selective and potent across a large panel of cancer cell lines.

Here, a novel cytotoxic compound was identified with great selectivity and low-nM potency against cancer cell lines across multiple lineages. Using gene-expression correlates for chemogenomics, PDE3A was identified as the putative target of this small molecule, DNMDP. Interestingly, loss of PDE3A expression resulted in resistance to DNMDP. Moreover, PDE3A immunoprecipitation followed by isobaric stable isotope tags for relative abundance and quantitation by mass spectrometry (iTRAQ/MS) identified SLFN12 and SIRT7 as novel protein-protein interaction partners of PDE3A upon DNMDP binding, possibly due to allosteric modulation of the function of PDE3A. Importantly, SLFN12 expression was the top correlating gene with DNMDP sensitivity when corrected for PDE3A expression. Single gene or multi-gene expression correlations have shown to help elucidate the mechanism of action and relevant signaling pathways of small molecules. A novel biochemical target for cancer treatment was identified that is unlikely to have been found by target identification approaches such as loss-of-function screens or genomic analysis.

PDE3A belongs to the superfamily of phosphodiesterases and together with PDE3B forms the PDE3 family. The PDE3 family has dual substrate affinity and hydrolyses both cAMP and cGMP. Expression of PDE3A is highest in the cardiovascular system, platelets, kidney, and oocytes (Ahmad et al., Horm Metab Res 44, 776-785, 2012). The clinical PDE3 inhibitor cilostazol has been developed to treat intermittent claudication, as PDE3A inhibition in platelets impairs activation and platelet coagulation (Bedenis et al., Cochrane Database Syst Rev 10, CD003748, 2014). Other PDE3 inhibitors, such as milrinone, amrinone, and levosimendan, are indicated to treat congestive heart failure, where the combination of vasodilation and elevated cardiac cAMP levels increases cardiac contractility (Movsesian et al., Curr Opin Pharmacol 11, 707-713, 2011). None of these clinical inhibitors were able to replicate the cytotoxic phenotype of DNMDP, indicating that cyclic nucleotide hydrolysis was not sufficient to induce cell death in DNMDP-sensitive cell lines.

Interestingly however, other PDE3 inhibitors such as zardaverine, anagrelide, and quazinone have been reported previously to have cell cytotoxic characteristics in a select number of cancer cell lines (Sun et al., PLoS ONE 9, e90627, 2014; Fryknäs et al., J Biomol Screen 11, 457-468, 2006). In concordance with the present findings, other PDE3 and PDE4 inhibitors were found not to replicate the cytotoxic phenotype of zardaverine where retinoblastoma protein retinoblastoma 1 (RB1) expression was reported to separate zardaverine sensitive cell lines from non-sensitive cell lines (Sun et al., PLoS ONE 9, e90627, 2014). This finding was in contrast to the present data where a correlation between cytotoxic activities of DNMDP and copy-number or mRNA expression of RB1 was not identified. Another PDE3 inhibitor, anagrelide, uniquely inhibited megakaryocyte differentiation, resulting in apoptosis. Other PDE3 inhibitors tested did not have this activity (Wang et al., Br. J. Pharmacol. 146, 324-332, 2005; Espasandin, Y. et al., J. Thromb. Haemost. n/a-n/a, 2015, doi:10.1111/jth.12850). It was hypothesized that the reported effects of zardaverine on cell viability and anagrelide on megakaryocyte differentiation are mediated through the same PDE3A modulation as described in this study.

Multiple PDE3 inhibitors were competitive inhibitors and have been shown to occupy the catalytic binding site of cAMP and cGMP (Card et al., Structure 12, 2233-2247, 2004; Zhan et al., Mol. Pharmacol. 62, 514-520, 2002). In addition, zardaverine has been co-crystalized in a complex with PDE4D, where it occupies the cAMP-binding site, and has been modeled to bind PDE3B in a similar manner (Lee et al., FEBS Lett. 530, 53-58, 2002). Given the structural similarity of DNMDP to zardaverine and that DNMDP inhibited both PDE3A and PDE3B, it was hypothesized that the binding mode of DNMDP is very similar to that of zardaverine. This indicated that in addition to acting as a cAMP/cGMP-competitive inhibitor, DNMDP allosterically induces a conformation that is responsible for its cytotoxic phenotype. Allosteric modulation of phosphodiesterases has been described previously for PDE4, where small molecules bound in the active site and simultaneously interacted with regulatory domains that came across the PDE4 active site. As a result, allosteric modulators stabilized a protein conformation that has been shown to differentially bind different PDE4 partner proteins (Burgin et al., Nat Biotechnol 28, 63-70, 2010).

The study of proteins associated with PDE3A might illuminate both its normal function and the way in which PDE3A modulators such as DNMDP kill cancer cells. PDE3A interacted with protein phosphatase 2 subunits, which are implicated in oncogenic viral transformation and are mutated in human cancers (Nagao et al., Int. Symp. Princess Takamatsu Cancer Res. Fund 20, 177-184, 1989; Imielinski et al., Cell 150, 1107-1120, 2012; Lawrence et al., Nature 499, 214-218, 2013), indicating a role for PDE3A in cancer cell signaling. Even though these interactions were not induced by DNMDP binding, the importance of the protein phosphatases in cancer biology would warrant further research.

The enhanced interaction between PDE3A and SLFN12, facilitated by DNMDP binding to PDE3A, and the correlation between sensitivity to DNMDP with SLFN12 expression strongly indicated that it is necessary to understand the functional impact of the PDE3A-SLFN12 interaction. However, little is known at this time about the functional role of SLFN12 in human physiology and cancer biology. SLFN12 is part of the schlafen gene family that diverges largely between humans and rodents. The large difference is due to rapid gene evolution and positive selection (Bustos et al., Gene 447, 1-11, 2009). Therefore, SLFN12 has no murine orthologue, preventing the study of SLFN12 in a well-understood model organism. The single publication on SLFN12 showed modulation of prostate cancer cell lines after ectopic expression of SLFN12 (Kovalenko et al., J. Surg. Res. 190, 177-184, 2014). Additional studies into the function of SLFN12 and its interaction with PDE3A could elucidate the mechanism of DNMDP cytotoxicity. Two observations indicated that DNMDP acted as a neomorph or hypermorph on PDE3A function: 1) DNMDP-sensitive cancer cell lines did not depend on PDE3A expression for survival, but rather PDE3A knock-down led to DNMDP resistance; and 2) DNMDP induced or enhanced protein-protein interactions upon binding to PDE3A. Lenalidomide was an example of a small molecule that acted as a neomorph or hypermorph rather than as an enzymatic inhibitor. Lenalidomide modulated a specific protein-protein interaction between the cereblon ubiquitin ligase and Ikaros transcription factors, which were then subsequently targeted for degradation (Krönke et al., Science 343, 301-305, 2014; Lu et al., Science 343, 305-309, 2014). By analogy, DNMDP might directly stabilize a PDE3A-SLFN12 interaction, or DNMDP could allosterically stabilize a PDE3 conformation that binds SLFN12. Either of these mechanisms could result in a neo- or hypermorphic phenotype. Further characterization of the neomorphic phenotype induced by DNMDP might facilitate synthesis of small molecules that will not inhibit cyclic nucleotide hydrolysis by PDE3A. Toxicity profiles of such small molecules should differ from PDE3 inhibitors prescribed for cardiovascular indications.

This study has uncovered a previously unknown role for PDE3A in cancer maintenance, in which its function can be modified by a subset of PDE3 inhibitors, resulting in toxicity to a subset of cancer cell lines. These data indicated that DNMDP and its analogs had a hyper- or neomorphic effect on PDE3A, leading to cellular toxicity, which was corroborated by cells becoming less sensitive to DNMDP with decreasing levels of cellular PDE3A. These observations are comparable with other reports of allosteric modulation of phosphodiesterases (Burgin et al., Nat Biotechnol 28, 63-70, 2010), indicating that DNMDP and analogues may have similar effects on PDE3A. The exact mechanism of cell-selective cytotoxicity remains unknown for now; however, further studies into the novel interactions with SLFN12, and perhaps SIRT7, might be informative.

In summary, the study herein used differential cytotoxicity screening to discover a cancer cell cytotoxic small molecule, DNMDP. Profiling of DNMDP in 766 genomically-characterized cancer cell lines revealed stereospecific nanomolar efficacy in about 3% of cell lines tested. A search for genomic features that indicated sensitivity revealed that elevated PDE3A expression strongly correlated with DNMDP response. DNMDP inhibited PDE3A and PDE3B, with little or no activity towards other PDEs. However, unexpectedly, most other PDE3A inhibitors tested did not phenocopy DNMDP, including the potent and selective PDE3A inhibitor, trequinsin. Co-treatment of DNMDP-sensitive cells with trequinsin competed away the cancer cell cytotoxic activity of DNMDP, and knockout of PDE3A rescued the otherwise sensitive cells from DNMDP-induced cytotoxicity, leading us to hypothesize that PDE3A is required for cancer cell killing by DNMDP, which induces a neomorphic alteration of PDE3A. Mass spectrometric analysis of PDE3A immunoprecipitates alone or in the presence of DNMDP or trequinsin revealed differential binding of SLFN12 and SIRT7 only in the presence, of DNMDP. Similar to PDE3A, SLFN12 expression levels were elevated in DNMDP-sensitive cell lines, and knock down of SLFN12 with shRNA decreased sensitivity of cells to DNMDP, indicating that DNMDP-induced complex formation of PDE3A with SLFN12 is critical to the cancer cell cytotoxic phenotype. Results herein therefore implicate PDE3A modulators as candidate cancer therapeutic agents and demonstrate the power of chemogenomics in small molecule discovery.

The experiments above were performed with the following methods and materials.

Compound Library Screening in NCI-H1734 and A549 Cell Lines

1500 NCI-H1734 or 1000 A549 cells were plated in a 384-well plate in 40 μl of RPMI supplemented with 10% Fetal Bovine Serum and 1% Pen/Strep. 24 hours after plating, a compound-library of 1924 small molecules was added at a concentration of 10 μM. Staurosporine was used a positive control for cytotoxicity at a concentration of 10 μM, and DMSO was used a negative control at a concentration of 1%. All compounds were incubated for 48 hours with indicated small molecules. After 48 hours, 384-well plates were removed from the incubator and allowed to cool to room temperature for 20 minutes. Cell viability was assessed by adding 40 μl of a 25% CELLTITERGLO® (Promega) in PBS with a THERMO COMBI™ or multi-channel-pipette and incubated for 10 minutes. The luminescence signal was read using a Perkin-Elmer EnVision. Viability percentage was calculated by normalizing to DMSO controls.

Compound Sensitivity Testing in Cell Lines

1000 HeLa (DMEM), 1000 A549 (RPMI), 500 MCF-7 (DMEM), 4000 PC3 (F12-K), 1000 NCI-H2122 (RPMI) or 1500 NCI-H1563 (RPMI) cells were plated in a 384-well plate in 40 μl of corresponding growth media supplemented with 10% Fetal Bovine Serum. 24 hours after plating, indicated compounds were added at indicated concentrations and incubated for 48 hours. Cell viability was assessed as described in Compound library screening in NCI-H1734 and A549 cell lines.

Caspase Activity in HeLa Cells

1000 HeLa cells were plated in 384-well plate in 40 μl of corresponding growth media supplemented with 10% Fetal Bovine Serum. 24 hours after plating, indicated compounds were added at indicated concentrations and incubated for 48 hours. Caspase-Glo from Promega was added according to the manufacturers recommendations and luminescence was determined as described in Compound library screening in NCI-H1734 and A549 cell lines.

Large-Scale Cell-Line Viability Measurements

The sensitivity of 777 cancer cell lines (CCLs) was measured drawn from 23 different lineages to DNMDP. Each cell line was plated in its preferred media in white opaque 1536-plates at a density of 500 cells/well. After incubating overnight, DNMDP was added by acoustic transfer at 16 concentrations ranging from 66.4 μM-2 nM in 2-fold steps in duplicate (Labcyte Echo 555, Labcyte Inc., Sunnyvale, Calif.). After 72 hours treatment, cellular ATP levels were measured as a surrogate for viability (CELLTITERGLO®, Promega Corporation, Madison, Wis.) according to manufacturer's protocols using a ViewLux Microplate Imager (PerkinElmer, Waltham, Mass.) and normalized to background (media-only) and vehicle (DMSO)-treated control wells.

Concentration response curves were fit using nonlinear fits to 2- or 3-parameter sigmoid functions through all 16 concentrations with the low-concentration asymptote set to the DMSO-normalized value, and an optimal 8-point dose curve spanning the range of compound-sensitivity was identified. The area under the 8-point dose curve (AUC) was computed by numeric integration as a metric for sensitivity for further analysis. Similar sensitivity measurements have been obtained for a collection of 480 other compounds, enabling analyses that identify cell lines responding uniquely to DNMDP (see Broad Institute Cancer Therapeutics Response Portal, a dataset to identify comprehensively relationships between genetic and lineage features of human cancer cell lines and small-molecule sensitivities for complete list of compounds).

Correlation of Sensitivity Measurements with Basal Gene Expression

Gene-centric robust multichip average (RMA)-normalized basal mRNA gene expression data measured on the Affymetrix GeneChip Human Genome U133 Plus 2.0 Array were downloaded from the Cancer Cell Line Encyclopedia (CCLE, a detailed genetic characterization of a large panel of human cancer cell lines; Barretina et al., Nature 483, 603-607, 2012). Pearson correlation coefficients were calculated between gene expression (18,988 transcripts) and areas under the curve (AUCs) across 760 overlapping CCLs. For comparisons across small molecules exposed to differing numbers of CCLs, correlation coefficients were transformed using Fisher's transformation.

Chemistry Experimental Methods

General Details

All reactions were carried out under nitrogen (N2) atmosphere. All reagents and solvents were purchased from commercial vendors and used as received. Nuclear magnetic resonance (NMR) spectra were recorded on a Bruker (300 or 400 MHz $^{1}H$, 75 or 101 MHz $^{13}C$) spectrometer. Proton and carbon chemical shifts are reported in ppm (δ) referenced to the NMR solvent. Data are reported as follows: chemical shifts, multiplicity (br=broad, s=singlet, d=doublet, t=triplet, q=quartet, m=multiplet; coupling constant(s) in Hz). Flash chromatography was performed using 40-60 μm Silica Gel (60 Å mesh) on a Teledyne Isco Combiflash Rf. Tandem Liquid Chromatography/Mass Spectrometry (LC/MS) was performed on a Waters 2795 separations module and 3100 mass detector with a Waters Symmetry C18 column (3.5 μm, 4.6×100 mm) with a gradient of 0-100% CH3CN in water over 2.5 min with constant 0.1% formic acid. Analytical thin layer chromatography (TLC) was performed on EM Reagent 0.25 mm silica gel 60-F plates. Elemental analysis was performed by Robertson Microlit Laboratories, Ledgewood N.J.

Synthesis of (R)-DNMDP

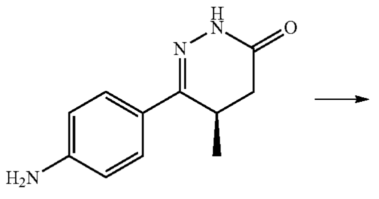

A

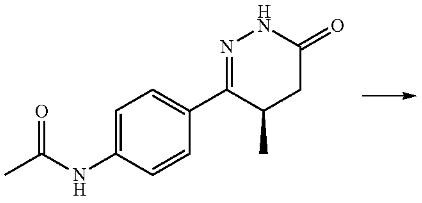

B

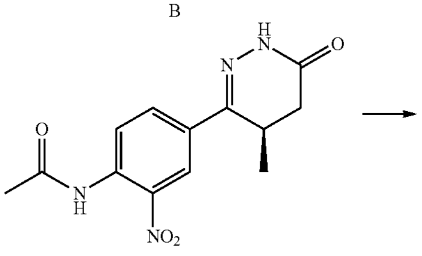

C

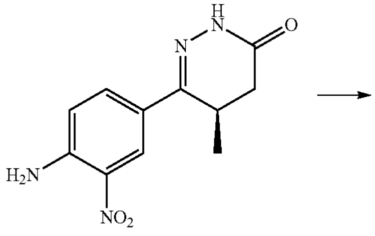

D

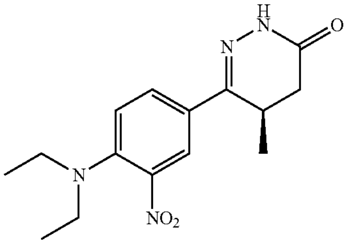

(R)-DNMDP

In 5 mL of acetic anhydride, 2.00 g (9.84 mmol) of (R)-6-(4-aminophenyl)-5-methyl-4,5-dihydropyridazin-3(2H)-one (A, Toronto Research Chemicals) was stirred 1 hour before addition of 30 mL water, filtration, rinsing the solids with water and drying to yield 2.20 g of product B (91%). $^1H$ NMR (300 MHz, DMSO-$d_6$) δ 10.92 (s, 1H), 10.13 (s, 1H), 7.74 (d, J=8.9, 2H), 7.65 (d, J=8.8, 2H), 3.41-3.33 (m, 1H), 2.68 (dd, J=6.8, 16.8, 1H), 2.23 (d, J=16.7, 1H), 2.08 (s, 3H), 1.07 (d, J=7.3, 3H). $^{13}C$ NMR (75 MHz, DMSO-$d_6$) δ 168.50, 166.27, 152.25, 140.27, 129.24, 126.24, 118.70, 33.47, 26.91, 24.02, 15.87. HPLC: $R_t$ 0.72 min, purity >95%. MS: 246 (M+1).

To 3.09 g of B (15.3 mmol) dissolved in 30 mL of sulfuric acid and cooled in an ice bath was added 0.72 mL of 90% nitric acid (15 mmol) in 8 mL sulfuric acid via an addition funnel over 10 minutes. After stirring 1 hour the mixture was poured onto ice. The yellow solid was filtered off and the water was rinsed several times with EtOAc before drying and combining with the yellow solid. Chromatography with 40-60% EtOAc in hexane yielded 1.12 g (25%) of product as a yellow solid which was recrystallized from EtOAc. $^1H$ NMR (300 MHz, DMSO-$d_6$) δ 11.13 (s, 1H), 10.41 (s, 1H), 8.25 (d, J=1.8, 1H), 8.07 (dd, J=1.8, 8.6, 1H), 7.71 (d, J=8.6, 1H), 3.55-3.40 (m, 1H), 2.74 (dd, J=6.9, 16.8, 1H), 2.27 (d, J=16.8, 1H), 2.09 (s, 3H), 1.08 (d, J=7.2, 3H). $^{13}C$ NMR (75 MHz, DMSO-d6) δ 168.57, 166.31, 150.37, 142.19, 131.69, 131.32, 130.60, 125.07, 121.70, 33.30, 26.81, 23.44, 15.64. TLC: Rf 0.25 (1:1 EtOAc:hexane). HPLC: $R_t$ 0.87 min, purity >95%. MS: 291 (M+1). HRMS Exact Mass (M+1): 291.1088. Found: 291.1091.

To 58 mg of C (0.20 mmol) dissolved in 10 mL of MeOH was added a solution of 48 mg NaOH (1.2 mmol) in 0.5 mL water. After 1 hour the reaction was concentrated, water was added and rinsed with EtOAc, the EtOAc was dried and concentrated to give 48 mg (93%) of product D. $^1H$ NMR (300 MHz, DMSO-d6) δ 10.92 (s, 1H), 8.28 (d, J=2.0, 1H), 7.87 (dd, J=2.1, 9.0, 1H), 7.76 (s, 2H), 7.06 (d, J=9.0, 1H), 3.33 (s, 1H), 2.67 (dd, J=6.8, 16.8, 1H), 2.22 (d, J=16.6, 1H), 1.06 (d, J=7.3, 3H). $^{13}C$ NMR (75 MHz, DMSO-$d_6$) δ 166.25, 151.12, 146.69, 132.72, 129.80, 122.57, 122.19, 119.80, 33.43, 26.70, 15.77. MS: 249 (M+1).

To 35 mg of amine D (0.14 mmol) dissolved in 0.5 mL Dimethylformamide (DMF) was added 70 mg of acetaldehyde (1.6 mmol) and 170 mg of $NaBH(OAc)_3$ (0.80 mmol) and 10 μL, (0.2 mmol) of HOAc. After stirring 3 hours, water and EtOAc were added, the EtOAc separated, dried, concentrated and chromatographed with 30-50% EtOAc in hexane to isolate 3 mg of the (R)-DNMDP (7%). The synthesized material was identical to purchased racemic material by TLC, HPLC and $^1H$ NMR. $^1H$ NMR (300 MHz, $CDCl_3$) δ 8.58 (s, 1H), 8.04 (d, J=2.3, 1H), 7.84 (dd, J=2.3, 9.0, 1H), 7.11 (d, J=9.0, 1H), 3.30-3.36 (m, 1H), 3.26 (q, J=7.1, 4H), 2.71 (dd, J=6.8, 16.9, 1H), 2.48 (d, J=17.0, 1H), 1.25 (d, J=7.4, 3H), 1.16 (t, J=7.1, 6H). TLC: Rf 0.25 (1:1 EtOAc:hexane). HPLC: $R_t$ 1.27 min, purity >95%. MS: 305 (M+1). Exact Mass (M+1): 305.1608 Found: 305.1616. $^{13}C$ NMR (75 MHz, $CDCl_3$, purchased material) δ 166.28, 152.02, 145.24, 141.21, 129.77, 124.94, 123.94, 121.00, 46.10, 33.80, 27.81, 16.24, 12.56.

The optical purity of (R)-DNMDP was determined using chiral SCF chromatography and comparison to commercially available racemic material: Column: ChiralPak AS-H, 250×4.6 mm, 5 μm, Mobile Phase Modifier: 100% Methanol, Gradient: 5 to 50% Methanol over 10 minutes, Flow Rate: 4 mL/min, Back Pressure: 100 bar, Column Temperature: 40 C. UV detection was from 200-400 nm. Retention times of separated isomers: 5.36, 6.64 minutes; retention time of (R)-DNMDP, 6.60 minutes, 1:19 ratio of enantiomers detected.

2

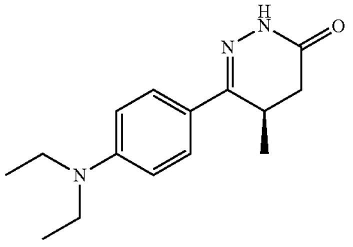

2. To 200 mg (0.98 mmol) of A dissolved in 5 mL of MeOH was added 87 mg of acetaldehyde (2.0 mmol), 113 uL of HOAc (2.0 mmol) and 124 mg (2.0 mmol) of $NaBH_3CN$ and the reaction was stirred overnight at room temperature. The next day the same quantity of reagents were added and the reaction stirred another 24 hours. The mixture was concentrated and partitioned between $CH_2Cl_2$ and water, the $CH_2Cl_2$ was separated, dried, and concentrated before chromatography with 20-40% EtOAc in hexane isolated 210 mg of product as a white solid (82%). $^1H$ NMR (300 MHz, $CDCl_3$) δ 8.95 (s, 1H), 7.64 (d, J=8.7, 2H), 6.66 (d, J=8.7, 2H), 3.37 (dd, J=9.6, 16.4, 5H), 2.67 (dd, J=6.5, 16.8, 1H), 2.43 (d, J=16.8, 1H), 1.41-1.02 (m, 10H). $^{13}C$ NMR (75 MHz, $CDCl_3$) δ 166.82, 154.55, 148.79, 127.32, 120.81, 111.08, 44.32, 33.92, 27.74, 16.37, 12.50. TLC: Rf 0.25 (1:1 EtOAc:hexane). HPLC: $R_t$ 1.05 min, purity >95%. MS: 260 (M+1). HRMS Exact Mass (M+1): 260.1757. Found: 260.1764

3

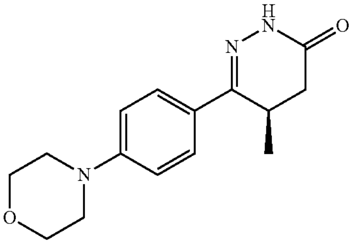

3. To 200 mg (0.984 mmol) of A dissolved in 1 mL of Dimethylformamide (DMF) was added 250 μL (2.00 mmol) of bis (2-bromoethyl) ether and 400 mg of K2CO3 and the mixture was stirred overnight at 60° C. The next day another 250 μL of bis (2-bromoethyl) ether and 170 mg of K2CO3 were added. After 3 hours, EtOAc and water were added, the water was rinsed with EtOAc, the combined EtOAc washes were dried and concentrated. Chromatography with 0-4% MeOH in CH2Cl2 yielded 125 mg of product (46%). $^1H$ NMR (300 MHz, $CDCl_3$) δ 8.61 (s, 1H), 7.68 (d, J=8.8, 2H), 6.92 (d, J=8.8, 2H), 3.99-3.76 (m, 4H), 3.44-3.31 (m, 1H), 3.29-3.22 (m, 4H), 2.70 (dd, J=6.7, 16.8, 1H), 2.46 (d, J=16.7, 1H), 1.24 (d, J=7.3, 3H). $^{13}C$ NMR (75 MHz, $CDCl_3$) δ 166.64, 154.05, 152.18, 127.10, 125.33, 114.73, 66.69, 48.33, 33.93, 27.94, 16.36. TLC: $R_f$ 0.1 (1:50 MeOH: $CH_2Cl_2$). HPLC: $R_t$ 1.05 min, purity >95%. MS: 274 (M+1). HRMS: calcd. 274.1556 (M+1); found 274.1552. Anal. Calcd. for $C_{15}H_{19}N_3O_2$: C, 65.91; H, 7.01; N, 15.37; Found. 65.81, H, 6.66, N, 15.26.

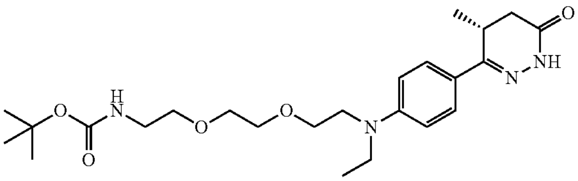 [SMILES: CCN(CCOCCOCCNC(=O)OC(C)(C)C)c1ccc(C2=NNC(=O)C[C@H]2C)cc1]

DNMDP-2L.

To 130 mg of A (0.64 mmol) dissolved in 0.4 mL of Dimethylformamide (DMF) was added 100 mg of tert-butyl 2-(2-(2-bromoethoxy)ethoxy)-ethylcarbamate (Toronto Research Chemical, 0.32 mmol) and 90 mg of $K_2CO^3$ (64 mmol) and the mixture was stirred at 60° C. overnight. After cooling, water was added and rinsed several times with EtOAc. The combined EtOAc layers were dried, concentrated, and chromatographed with 50-70% EtOAc to yield 81 mg of product (58%). NMR (300 MHz, $CDCl_3$) δ 9.06 (s, 1H), 7.59 (d, J=8.8 Hz, 2H), 6.62 (d, J=8.8 Hz, 2H), 5.15 (s, 1H), 4.53 (s, 1H), 3.72 (t, J=5.2 Hz, 2H), 3.65 (s, 4H), 3.55 (t, J=5.2 Hz, 2H), 3.32 (m, 5H), 2.67 (dd, J=16.8, 6.7 Hz, 1H), 2.42 (d, J=16.4 Hz, 1H), 1.44 (s, 9H), 1.22 (d, J=7.4 Hz, 3H). $^{13}C$ NMR (75 MHz, $CDCl_3$) δ 166.83, 155.99, 154.45, 149.64, 127.33, 123.24, 112.58, 79.28, 70.30, 70.26, 70.22, 69.45, 43.14, 40.39, 33.96, 28.43, 27.89, 16.40; HPLC: $R_t$ 2.50 min (7.5 min run), purity >95%. MS: 435 (M+1). This product (0.19 mmol) was dissolved in 1 mL MeOH and to the solution was added acetaldehyde (50 uL, 0.89 mmol), 10 uL HOAc (0.2 mmol) and 12 mg $NaBH_3CN$ (0.19 mmol). After 1 hour, $NaHCO_3$(aq) and $CH_2Cl_2$ were added, the $CH_2Cl_2$ was separated and the water washed twice with $CH_2Cl_2$. The combined $CH_2Cl_2$ was dried, concentrated, and chromatography with 60-70% EtOAc in hexane yielded 71 mg of product as a clear oil (82%). $^1H$ NMR (400 MHz, $CDCl_3$) δ 8.91 (s, 1H), 7.63 (d, J=8.9 Hz, 2H), 6.69 (d, J=8.9 Hz, 2H), 5.07 (s, 1H), 3.65 (t, J=6.0 Hz, 2H), 3.61 (s, 4H), 3.55 (dt, J=9.9, 5.5 Hz, 4H), 3.46 (q, J=7.0 Hz, 2H), 3.38-3.22 (m, 3H), 2.67 (dd, J=16.8, 6.7 Hz, 1H), 2.43 (d, J=16.7 Hz, 1H), 1.45 (s, 10H), 1.23 (d, J=7.3 Hz, 3H), 1.18 (t, J=7.0 Hz, 3H). $^{13}C$ NMR (101 MHz, $CDCl_3$) δ 166.84, 155.96, 154.46, 148.89, 127.35, 121.38, 111.28, 79.22, 70.68, 70.27, 70.24, 68.74, 49.95, 45.49, 40.32, 33.97, 28.43, 27.80, 16.43, 12.14. $R_t$ 2.99 min (7.5 min run), purity >95%. MS: 463 (M+1).

Attachment to Resin

To a solution of 18 mg of DNMDP-2L (0.04 mmol) in 0.8 mL of $CH_2Cl_2$ was added 0.2 mL of trifluoroacetic acid (TFA) and the solution was stirred 2 h before concentration and dissolution in 0.5 mL DMSO. To this was added 10 uL of $Et_3N$ (0.07 mmol) and 12 mg of N,N'-disuccinimidyl carbonate (DSC) (0.05 mmol) and the solution was stirred overnight. LC analysis indicated the reaction was not complete, another 25 mg of N,N'-disuccinimidyl carbonate (0.1 mmol) was added. LC analysis after 2 hours showed ca. 5:1 ratio of DSC product:amine. A 1 mL sample of Affi-Gel 102 resin was rinsed five times with DMSO with a centrifuge, then suspended in 0.5 mL DMSO. To the resin was added 30 uL of the DSC product solution and 25 uL Et3N and the mixture was swirled. After 2 days, LC analysis of the DMSO solution showed complete disappearance of the DCS adduct; the underivatized amine was still present. The DMSO was removed by centrifuge and decanted and the resin was rinsed several times with DMSO and stored in PBS buffer.

Bioactives Screen to Rescue DNMDP Induced Cytotoxicity

1000 HeLa cells were plated in a 384-well plate in 40 μl of DMEM supplemented with 10% Fetal Bovine Serum and 1% Pen/Strep. 24 hours after plating, a compound-library of 1600 bioactive molecules (Pharmacon) was added at a concentration of 20 μM. In parallel to bioactive compound incubation, DNMDP was added to a final concentration of 30 nM and incubated for 48 hours. Cell viability was assessed as described in Compound library screening in NCI-H1734 and A549 cell lines.

Linker-Affinity Purification of Molecular Target of DNMDP and Immunoblotting

HeLa cells were washed with ice-cold PBS before lysed with NP-40 lysis buffer (150 mM NaCl, 10% glycerol, 50 mM Tris-Cl pH 8.0, 50 mM $MgCl_2$, 1% NP-40) supplemented with EDTA-free protease inhibitors (Roche) and phosphatase inhibitor mixtures I and II (Calbiochem). Cell lysates were incubated on ice for at least 2 minutes and subsequently centrifuged for 10 minutes at 4° C. at 15,700×g after which the supernatant was quantified using BCA protein assay kit (Pierce). 200 μg total HeLa cell lysate was incubated with 3 μl Affi-Gel 102 resin (BioRad) coupled to affinity linker DNMDP-2L in a total volume of 400 μl for four hours. Prior to incubation, indicated compounds were added to affinity purifications at a final concentration of 10 μM. Samples were washed three times with lysis buffer containing corresponding compound concentrations of 10 μM. Proteins bound to Affi-Gel 102 resin were reduced, denatured, and separated using Tris-Glycine gels (Novex) and transferred to nitrocellulose membranes using the iBlot transfer system (Novex). Membranes were incubated overnight at 4° C. with primary antibodies against PDE3A (1:1000, Bethyl). Incubation with secondary antibodies (1:20,000, LI-COR Biosciences) for two hours at room temperature and subsequent detection (Odyssey Imaging System, LI-COR Biosciences) were performed according to manufacturer's recommendations.

PARP-Cleavage Immunoblotting

HeLa cells were treated with indicated concentration of DNMDP and staurosporine for 36 hours. HeLa cells were lysed and processed as described in Linker-affinity purification of molecular target of DNMDP and immunoblotting. Membranes were incubated with an antibody against PARP (1:1000, Cell Signaling #9532) and actin and subsequently imaged as described in Linker-affinity purification of molecular target of DNMDP and immunoblotting.

Targeting PDE3A Locus Using CRISPR

CRISPR target sites were identified using the MIT CRISPR Design Tool (online MIT CRISPR design portal). For cloning of sgRNAs, forward and reverse oligos were annealed, phosphorylated and ligated into BsmBI-digested pXPR_BRD001. Oligo sequences are as follows:

| sgRNA | Forward oligo | Reverse oligo |
|---|---|---|
| PDE3A_sg1 | CACCGTTTTCACTGAGCGAAGTGA (SEQ ID NO.: 7) | AAACTCACTTCGCTCAGTGAAAAC (SEQ ID NO.: 8) |
| PDE3A_sg2 | CACCGAGACAAGCTTGCTATTCCAA (SEQ ID NO.: 9) | AAACTTGGAATAGCAAGCTTGTCTC (SEQ ID NO.: 10) |
| PDE3A_sg3 | CACCGGCACTCTGAGTGTAAGTTA (SEQ ID NO.: 11) | AAACTAACTTACACTCAGAGTGCC (SEQ ID NO.: 12) |

To produce lentivirus, 293T cells were co-transfected with pXPR_BRD001, psPAX2 and pMD2.G using calcium phosphate. Infected HeLa cells were selected with 2 ug/ml of puromycin.

Reduction of PDE3A Expression Using siRNA

HeLa cells were plated in 96-well plates and transfected after 24 hours with PDE3A and Non-Targeting siRNA smartpools (On Target Plus, Thermo Scientific) according to the manufacturers recommendations. HeLa cell lysate was obtained 24 hours and 72 hours after transfection and immunoblotted for PDE3A and Actin (1:20,000, Cell Signaling) as described in Linker-affinity purification of molecular target of DNMDP and immunoblotting. HeLa cells were treated for 48 hours with indicated concentrations of Compound 3. Cell viability was assessed as described in Compound library screening in NCI-H1734 and A549 cell lines.

Measuring Cellular cAMP Concentrations in HeLa Cells

5000 HeLa cells were plated in 96-well plates. 24 hours after plating, HeLa cells were incubated for one hour with indicated compounds at indicated concentrations. cAMP levels were determined with the CAMP-GLO™ assay (Promega) according to the manufacturers recommendations. Cellular concentrations of cAMP were determined by normalizing to a standard curve generated according to the manufacturers recommendations.

Extended Proteomics Methods for PDE3A-Protein Interaction Studies

Immunoprecipitation of PDE3A in HeLa Cells

HeLa cells were treated for four hours prior to lysis with 10 μM of indicated compounds: DMSO, DNMDP and trequinsin. HeLa cells were lysed with ModRipa lysis buffer (1% NP-40:50 mM Tris-HCl, pH 7.8, 150 mM NaCl, 0.1% sodium deoxycholate, 1 mM EDTA) supplemented with protease and phosphatase inhibitors as described in *Linker-affinity purification of molecular target of DNMDP and immunoblotting*, and indicated compounds as described above to a final concentration of 10 μM. 13 mg of HeLa total cell lysate was incubated with 0.5% PDE3A antibody (Bethyl) and incubated overnight. Blocking peptide (Bethyl) against the PDE3A antibody was added simultaneously with the PDE3A antibody in the corresponding condition. Total cell lysate and antibody mixture was then incubated with 10 μl Protein A Plus Agarose (Fisher Scientific) for 30 minutes at 4° C. Protein A Plus Agarose was then washed two times with lysis buffer containing indicated compounds at a concentration of 10 μM. Finally, Protein A Plus Agarose was washed once with lysis buffer containing no NP-40 and indicated compounds at a concentration of 10 μM.

On-Bead Digest

The beads from immunopurification were washed once with IP lysis buffer, then three times with PBS, the three different lysates of each replicate were resuspended in 90 uL digestion buffer (2M Urea, 50 mM Tris HCl), 2 ug of sequencing grade trypsin added, 1 hour shaking at 700 rpm. The supernatant was removed and placed in a fresh tube. The beads were then washed twice with 50 uL digestion buffer and combined with the supernatant. The combined supernatants were reduced (2 uL 500 mM DTT, 30 minutes, room temperature), alkylated (4 uL 500 mM IAA, 45 minutes, dark) and a longer overnight digestion performed: 2 ug (4 uL) trypsin, shake overnight. The samples were then quenched with 20 uL 10% folic acid (FA) and desalted on 10 mg SEP-PAK® columns.

iTRAQ Labeling of Peptides and Strong Cation Exchange (SCX) Fractionation

Desalted peptides were labeled with isobaric tags for relative and absolute quantification (iTRAQ)-reagents according to the manufacturer's instructions (AB Sciex, Foster City, Calif.). Peptides were dissolved in 30 μl of 0.5 M TEAB pH 8.5 solution and labeling reagent was added in 70 ul of ethanol. After 1 hour incubation the reaction was stopped with 50 mM Tris/HCl pH 7.5. Differentially labeled peptides were mixed and subsequently desalted on 10 mg SEP-PAK® columns.

| | iTRAQ labeling | | | |
|---|---|---|---|---|
| | 114 | 115 | 116 | 117 |
| Rep1 | Blocking peptide | No addition | DNMDP | trequinsin |
| Rep2 | Blocking peptide | No addition | DNMDP | trequinsin |

SCX fractionation of the differentially labelled and combined peptides was done as described in Rappsilber et al. (Rappsilber et al., Nat Protoc 2, 1896-1906, 2007), with 6 pH steps (buffers-all contain 25% acetonitrile) as below:

1: ammonium acetate 50 mM pH 4.5,
2: ammonium acetate 50 mM pH 5.5,
3: ammonium acetate 50 mM pH 6.5,
4: ammonium bicarbonate 50 mM pH 8,
5: ammonium hydroxide 0.1% pH 9,
6: ammonium hydroxide 0.1% pH 11.

Empore SCX disk used to make stop-and-go-extraction-tips (StageTips) as described in the paper.

MS Analysis

Reconstituted peptides were separated on an online nanoflow EASY-NLC™ 1000 UHPLC system (Thermo Fisher Scientific) and analyzed on a benchtop Orbitrap Q EXACTIVE™ mass spectrometer (Thermo Fisher Scientific). The peptide samples were injected onto a capillary column (PICOFRIT® with 10 μm tip opening/75 μm diameter, New Objective, PF360-75-10-N-5) packed in-house with 20 cm C18 silica material (1.9 μm REPROSIL-PUR® C18-AQ medium, Dr. Maisch GmbH, r119.aq). The UHPLC setup was connected with a custom-fit microadapting tee (360 μm, IDEX Health & Science, UH-753), and capillary columns were heated to 50° C. in column heater sleeves (Phoenix-ST) to reduce backpressure during UHPLC separation. Injected peptides were separated at a flow rate of 200 nL/min with a linear 80 min gradient from 100% solvent A (3% acetonitrile, 0.1% formic acid) to 30% solvent B (90% acetonitrile, 0.1% formic acid), followed by a linear 6 min gradient from 30% solvent B to 90% solvent B. Each sample was run for 120 minutes, including sample loading and column equilibration times. The Q EXACTIVE™ instrument was operated in the data-dependent mode acquiring high-energy collisional dissociation (HCD) MS/MS scans (R=17,500) after each MS1 scan (R=70,000) on the 12 top most abundant ions using an MS1 ion target of 3×106 ions and an MS2 target of 5×104 ions. The maximum ion time utilized for the MS/MS scans was 120 ms; the HCD-normalized collision energy was set to 27; the dynamic exclusion time was set to 20 s, and the peptide match and isotope exclusion functions were enabled.

Quantification and Identification of Peptides and Proteins

All mass spectra were processed using the Spectrum Mill software package v4.1 beta (Agilent Technologies) which includes modules developed by Applicants for isobaric tags for relative and absolute quantification (iTRAQ)-based quantification. Precursor ion quantification was done using extracted ion chromatograms (XIC's) for each precursor ion. The peak area for the XIC of each precursor ion subjected to MS/MS was calculated automatically by the Spectrum Mill software in the intervening high-resolution MS1 scans of the liquid chromatography (LC)-MS/MS runs using narrow windows around each individual member of the isotope cluster. Peak widths in both the time and m/z domains were dynamically determined based on MS scan resolution, precursor charge and m/z, subject to quality metrics on the relative distribution of the peaks in the isotope cluster vs theoretical. Similar MS/MS spectra acquired on the same precursor m/z in the same dissociation mode within +/−60 seconds were merged. MS/MS spectra with precursor charge >7 and poor quality MS/MS spectra, which failed the quality filter by not having a sequence tag length >1 (i.e., minimum of 3 masses separated by the in-chain mass of an amino acid) were excluded from searching.

For peptide identification MS/MS spectra were searched against human Universal Protein Resource (Uniprot) database to which a set of common laboratory contaminant proteins was appended. Search parameters included: ESI-Q EXACTIVE™-HCD scoring parameters, trypsin enzyme specificity with a maximum of two missed cleavages, 40% minimum matched peak intensity, +/−20 ppm precursor mass tolerance, +/−20 ppm product mass tolerance, and carbamidomethylation of cysteines and iTRAQ labeling of lysines and peptide n-termini as fixed modifications. Allowed variable modifications were oxidation of methionine, acetylation, Pyroglutamic acid (N-termQ), Deamidated (N), Pyro Carbamidomethyl Cys (N-termC), with a precursor MH+ shift range of −18 to 64 Da. Identities interpreted for individual spectra were automatically designated as valid by optimizing score and delta rank1-rank2 score thresholds separately for each precursor charge state in each liquid chromatography (LC)-MS/MS while allowing a maximum target-decoy-based false-discovery rate (FDR) of 1.0% at the spectrum level.

In calculating scores at the protein level and reporting the identified proteins, redundancy is addressed in the following manner: the protein score is the sum of the scores of distinct peptides. A distinct peptide is the single highest scoring instance of a peptide detected through an MS/MS spectrum. MS/MS spectra for a particular peptide may have been recorded multiple times, (i.e. as different precursor charge states, isolated from adjacent SCX fractions, modified by oxidation of Met) but are still counted as a single distinct peptide. When a peptide sequence >8 residues long is contained in multiple protein entries in the sequence database, the proteins are grouped together and the highest scoring one and its accession number are reported. In some cases when the protein sequences are grouped in this manner there are distinct peptides which uniquely represent a lower scoring member of the group (isoforms or family members). Each of these instances spawns a subgroup and multiple subgroups are reported and counted towards the total number of proteins. iTRAQ ratios were obtained from the protein-comparisons export table in Spectrum Mill. To obtain iTRAQ protein ratios the median was calculated over all distinct peptides assigned to a protein subgroup in each replicate. To assign interacting proteins the Limma package in the R environment was used to calculate moderated t-test p, as described previously and added Blandt-Altman testing to filter out proteins for which the CI for reproducibility was below 95% (Udeshi et al., Mol Cell Proteomics 11, 148-159, 2012).

Validation of DNMDP-Induced PDE3A Protein Interactions Using Immunoprecipitation and Immunoblotting HeLa cells were transfected with ORF overexpression constructs expressing V5-tagged SIRT7, V5-tagged SLFN12, or V5-tagged GFP. ORF expression constructs were obtained from the TRC (clone IDs: TRCN0000468231, TRCN0000476272, ccsbBroad304_99997). At 72 hours post transfection, cells were treated with 10 μM DNMDP or trequinsin for 4 hours followed by lysis using the ModRipa lysis buffer and immunoprecipitation of PDE3A. For each condition, 2 mg total protein lysate was incubated with 1 μg of anti-PDE3A antibody at 4° C. overnight, after which 7.5 μl each of Protein A- and Protein G-Dynabeads (Life Technologies 10001D and 10003D) were added and incubated for another 1 hour. Beads were washed and bound proteins were eluted with 30 μl of LDS PAGE gel loading buffer. Input (~60 μg total protein lysate) and IP products were resolved on 4-12% Tris-Glycine PAGE gels and immunoblotted with an anti-V5 antibody (Life Technologies R96205, 1:5000), the Bethyl anti-PDE3A antibody (1:1000), and secondary antibodies from LiCOR Biosciences (Cat.#926-32210 and 926068021, each at 1:10,000). Blots were washed and imaged using a LiCOR Odyssey infrared imager.

Knockdown of SLFN12 Expression Using shRNA and Testing for Drug Sensitivity

Constructs expressing shRNAs targeting SLFN12, or the control vector, were packaged into lentiviruses and delivered into HeLa cells by viral transduction. Three SLFN12-targeting shRNAs were used, all of which were obtained from the TRC (CloneIDs: TRCN0000152141 and TRCN0000153520). Infected cells were selected using 1 μg/ml puromycin for 3 days and then grown in non-selective media for 3 more days. Cells were then plated into 384-well assay plates and tested for drug sensitivity as described above. Knockdown of SLFN12 was validated by qPCR. Total RNA was extracted using kit reagents (RNeasy Mini Kit (Qiagen #74104) and QIAschredder (Qiagen #79656)). cDNA was generated using kit reagents (SuperScript III First-Strand Synthesis System (Life Technologies #18080-051)). qPCR was performed for GAPDH and SLFN12 (Life Technologies Hs00430118_ml) according to the manufacturer's recommendations. SLFN12 expression was normalized to corresponding samples GAPDH ct-values.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

INCORPORATION BY REFERENCE

The ASCII text file submitted herewith via EFS-Web, entitled "167741_011202. txt" created on August [[TBD]], 2016, having a size of [[TBD]] bytes, is hereby incorporated by reference in its entirety.

All patents and publications mentioned in this specification are herein incorporated by reference to the same extent as if each independent patent and publication was specifically and individually indicated to be incorporated by reference. In particular, Lewis et al., "Compounds and Compositions for the Treatment of Cancer," PCT/US2014/023263 (WO 2014/164704) is incorporated by reference in its entirety.

What is claimed is:

1. A method of reducing cancer cell proliferation, killing, or reducing the survival of a cancer cell selected as responsive to a phosphodiesterase 3A (PDE3A) modulator, the method comprising contacting the cell with a PDE3A modulator that induces interaction between PDE3A and Schlafen 12 (SLFN12) proteins in the cell, wherein the cell was selected as having an increase in the level of a PDE3A and a SLFN12 polypeptide or polynucleotide relative to a reference, thereby reducing cancer cell proliferation, killing, or reducing the survival of the cancer cell, wherein the PDE3A modulator is 6-(4-(diethylamino)-3-nitrophenyl)-5-methyl-4,5-dihydropyridazin-3(2H)-one (DNMDP), or a pharmaceutically acceptable salt thereof.

2. The method of claim 1, wherein the level of PDE3A or SLFN12 was detected by a method selected from the group consisting of immunoblotting, mass spectrometry, and immunoprecipitation.

3. The method of claim 1, wherein the level of PDE3A or SLFN12 polynucleotide is detected by a method selected from the group consisting of quantitative PCR, Northern Blot, microarray, mass spectrometry, and in situ hybridization.

4. The method of claim 1, wherein the cancer cell is a melanoma, endometrium, lung, hematopoietic/lymphoid, ovarian, cervical, soft-tissue sarcoma, leiomyosarcoma, urinary tract, pancreas, thyroid, kidney, glioblastoma, or breast cancer cell.

5. The method of claim 1, wherein the cancer cell is not a B-cell proliferative type cancer.

6. The method of claim 1, wherein the cancer cell is not multiple myeloma.

7. The method of claim 1, wherein the PDE3A modulator reduces an activity of PDE3A.

8. The method of claim 1, wherein the PDE3A modulator is administered orally.

9. The method of claim 1, wherein the PDE3A modulator is administered by intravenous injection.

10. The method of claim 1, wherein the cancer is a melanoma, endometrium, lung, hematopoietic/lymphoid, ovarian, cervical, soft-tissue sarcoma, leiomyosarcoma, urinary tract, pancreas, thyroid, kidney, glioblastoma, or breast cancer.

* * * * *

SEQUENCE LISTING

```
<160> NUMBER OF SEQ ID NOS: 10

<210> SEQ ID NO 1
<211> LENGTH: 1141
<212> TYPE: PRT
<213> ORGANISM: Homo sapiens

<400> SEQUENCE: 1

Met Ala Val Pro Gly Asp Ala Ala Arg Val Arg Asp Lys Pro Val His
1               5                   10                  15

Ser Gly Val Ser Gln Ala Pro Thr Ala Gly Arg Asp Cys His His Arg
            20                  25                  30

Ala Asp Pro Ala Ser Pro Arg Asp Ser Gly Cys Arg Gly Cys Trp Gly
        35                  40                  45

Asp Leu Val Leu Gln Pro Leu Arg Ser Ser Arg Lys Leu Ser Ser Ala
    50                  55                  60

Leu Cys Ala Gly Ser Leu Ser Phe Leu Leu Ala Leu Leu Val Arg Leu
65                  70                  75                  80

Val Arg Gly Glu Val Gly Cys Asp Leu Glu Gln Cys Lys Glu Ala Ala
```

-continued

```
                85                  90                  95

Ala Ala Glu Glu Glu Glu Ala Ala Pro Gly Ala Glu Gly Gly Val Phe
            100                 105                 110

Pro Gly Pro Arg Gly Gly Ala Pro Gly Gly Gly Ala Arg Leu Ser Pro
        115                 120                 125

Trp Leu Gln Pro Ser Ala Leu Leu Phe Ser Leu Leu Cys Ala Phe Phe
    130                 135                 140

Trp Met Gly Leu Tyr Leu Leu Arg Ala Gly Val Arg Leu Pro Leu Ala
145                 150                 155                 160

Val Ala Leu Leu Ala Ala Cys Cys Gly Gly Glu Ala Leu Val Gln Ile
                165                 170                 175

Gly Leu Gly Val Gly Glu Asp His Leu Leu Ser Leu Pro Ala Ala Gly
            180                 185                 190

Val Val Leu Ser Cys Leu Ala Ala Ala Thr Trp Leu Val Leu Arg Leu
        195                 200                 205

Arg Leu Gly Val Leu Met Ile Ala Leu Thr Ser Ala Val Arg Thr Val
    210                 215                 220

Ser Leu Ile Ser Leu Glu Arg Phe Lys Val Ala Trp Arg Pro Tyr Leu
225                 230                 235                 240

Ala Tyr Leu Ala Gly Val Leu Gly Ile Leu Leu Ala Arg Tyr Val Glu
                245                 250                 255

Gln Ile Leu Pro Gln Ser Ala Glu Ala Ala Pro Arg Glu His Leu Gly
            260                 265                 270

Ser Gln Leu Ile Ala Gly Thr Lys Glu Asp Ile Pro Val Phe Lys Arg
        275                 280                 285

Arg Arg Arg Ser Ser Ser Val Val Ser Ala Glu Met Ser Gly Cys Ser
    290                 295                 300

Ser Lys Ser His Arg Arg Thr Ser Leu Pro Cys Ile Pro Arg Glu Gln
305                 310                 315                 320

Leu Met Gly His Ser Glu Trp Asp His Lys Arg Gly Pro Arg Gly Ser
                325                 330                 335

Gln Ser Ser Gly Thr Ser Ile Thr Val Asp Ile Ala Val Met Gly Glu
            340                 345                 350

Ala His Gly Leu Ile Thr Asp Leu Leu Ala Asp Pro Ser Leu Pro Pro
        355                 360                 365

Asn Val Cys Thr Ser Leu Arg Ala Val Ser Asn Leu Leu Ser Thr Gln
    370                 375                 380

Leu Thr Phe Gln Ala Ile His Lys Pro Arg Val Asn Pro Val Thr Ser
385                 390                 395                 400

Leu Ser Glu Asn Tyr Thr Cys Ser Asp Ser Glu Glu Ser Ser Glu Lys
                405                 410                 415

Asp Lys Leu Ala Ile Pro Lys Arg Leu Arg Arg Ser Leu Pro Pro Gly
            420                 425                 430

Leu Leu Arg Arg Val Ser Ser Thr Trp Thr Thr Thr Thr Ser Ala Thr
        435                 440                 445

Gly Leu Pro Thr Leu Glu Pro Ala Pro Val Arg Arg Asp Arg Ser Thr
    450                 455                 460

Ser Ile Lys Leu Gln Glu Ala Pro Ser Ser Ser Pro Asp Ser Trp Asn
465                 470                 475                 480

Asn Pro Val Met Met Thr Leu Thr Lys Ser Arg Ser Phe Thr Ser Ser
                485                 490                 495

Tyr Ala Ile Ser Ala Ala Asn His Val Lys Ala Lys Lys Gln Ser Arg
            500                 505                 510
```

-continued

```
Pro Gly Ala Leu Ala Lys Ile Ser Pro Leu Ser Ser Pro Cys Ser Ser
        515                 520                 525

Pro Leu Gln Gly Thr Pro Ala Ser Ser Leu Val Ser Lys Ile Ser Ala
    530                 535                 540

Val Gln Phe Pro Glu Ser Ala Asp Thr Thr Ala Lys Gln Ser Leu Gly
545                 550                 555                 560

Ser His Arg Ala Leu Thr Tyr Thr Gln Ser Ala Pro Asp Leu Ser Pro
                565                 570                 575

Gln Ile Leu Thr Pro Pro Val Ile Cys Ser Ser Cys Gly Arg Pro Tyr
            580                 585                 590

Ser Gln Gly Asn Pro Ala Asp Glu Pro Leu Glu Arg Ser Gly Val Ala
        595                 600                 605

Thr Arg Thr Pro Ser Arg Thr Asp Asp Thr Ala Gln Val Thr Ser Asp
    610                 615                 620

Tyr Glu Thr Asn Asn Asn Ser Asp Ser Ser Asp Ile Val Gln Asn Glu
625                 630                 635                 640

Asp Glu Thr Glu Cys Leu Arg Glu Pro Leu Arg Lys Ala Ser Ala Cys
                645                 650                 655

Ser Thr Tyr Ala Pro Glu Thr Met Met Phe Leu Asp Lys Pro Ile Leu
            660                 665                 670

Ala Pro Glu Pro Leu Val Met Asp Asn Leu Asp Ser Ile Met Glu Gln
        675                 680                 685

Leu Asn Thr Trp Asn Phe Pro Ile Phe Asp Leu Val Glu Asn Ile Gly
    690                 695                 700

Arg Lys Cys Gly Arg Ile Leu Ser Gln Val Ser Tyr Arg Leu Phe Glu
705                 710                 715                 720

Asp Met Gly Leu Phe Glu Ala Phe Lys Ile Pro Ile Arg Glu Phe Met
                725                 730                 735

Asn Tyr Phe His Ala Leu Glu Ile Gly Tyr Arg Asp Ile Pro Tyr His
            740                 745                 750

Asn Arg Ile His Ala Thr Asp Val Leu His Ala Val Trp Tyr Leu Thr
        755                 760                 765

Thr Gln Pro Ile Pro Gly Leu Ser Thr Val Ile Asn Asp His Gly Ser
    770                 775                 780

Thr Ser Asp Ser Asp Ser Asp Ser Gly Phe Thr His Gly His Met Gly
785                 790                 795                 800

Tyr Val Phe Ser Lys Thr Tyr Asn Val Thr Asp Asp Lys Tyr Gly Cys
                805                 810                 815

Leu Ser Gly Asn Ile Pro Ala Leu Glu Leu Met Ala Leu Tyr Val Ala
            820                 825                 830

Ala Ala Met His Asp Tyr Asp His Pro Gly Arg Thr Asn Ala Phe Leu
        835                 840                 845

Val Ala Thr Ser Ala Pro Gln Ala Val Leu Tyr Asn Asp Arg Ser Val
    850                 855                 860

Leu Glu Asn His His Ala Ala Ala Ala Trp Asn Leu Phe Met Ser Arg
865                 870                 875                 880

Pro Glu Tyr Asn Phe Leu Ile Asn Leu Asp His Val Glu Phe Lys His
                885                 890                 895

Phe Arg Phe Leu Val Ile Glu Ala Ile Leu Ala Thr Asp Leu Lys Lys
            900                 905                 910

His Phe Asp Phe Val Ala Lys Phe Asn Gly Lys Val Asn Asp Asp Val
        915                 920                 925
```

```
Gly Ile Asp Trp Thr Asn Glu Asn Asp Arg Leu Leu Val Cys Gln Met
    930                 935                 940

Cys Ile Lys Leu Ala Asp Ile Asn Gly Pro Ala Lys Cys Lys Glu Leu
945                 950                 955                 960

His Leu Gln Trp Thr Asp Gly Ile Val Asn Glu Phe Tyr Glu Gln Gly
                965                 970                 975

Asp Glu Glu Ala Ser Leu Gly Leu Pro Ile Ser Pro Phe Met Asp Arg
            980                 985                 990

Ser Ala Pro Gln Leu Ala Asn Leu  Gln Glu Ser Phe Ile  Ser His Ile
        995                 1000                 1005

Val Gly  Pro Leu Cys Asn Ser  Tyr Asp Ser Ala Gly  Leu Met Pro
    1010                 1015                 1020

Gly Lys  Trp Val Glu Asp Ser  Asp Glu Ser Gly Asp  Thr Asp Asp
    1025                 1030                 1035

Pro Glu  Glu Glu Glu Glu Glu  Ala Pro Ala Pro Asn  Glu Glu Glu
    1040                 1045                 1050

Thr Cys  Glu Asn Asn Glu Ser  Pro Lys Lys Lys Thr  Phe Lys Arg
    1055                 1060                 1065

Arg Lys  Ile Tyr Cys Gln Ile  Thr Gln His Leu Leu  Gln Asn His
    1070                 1075                 1080

Lys Met  Trp Lys Lys Val Ile  Glu Glu Glu Gln Arg  Leu Ala Gly
    1085                 1090                 1095

Ile Glu  Asn Gln Ser Leu Asp  Gln Thr Pro Gln Ser  His Ser Ser
    1100                 1105                 1110

Glu Gln  Ile Gln Ala Ile Lys  Glu Glu Glu Glu Glu  Lys Gly Lys
    1115                 1120                 1125

Pro Arg  Gly Glu Glu Ile Pro  Thr Gln Lys Pro Asp  Gln
    1130                 1135                 1140


<210> SEQ ID NO 2
<211> LENGTH: 7319
<212> TYPE: DNA
<213> ORGANISM: Homo sapiens

<400> SEQUENCE: 2

gggggccact gggaattcag tgaagagggc accctatacc atggcagtgc ccggcgacgc      60

tgcacgagtc agggacaagc ccgtccacag tggggtgagt caagcccccca cggcgggccg     120

ggactgccac catcgtgcgg accccgcatc gccgcgggac tcgggctgcc gtggctgctg     180

gggagacctg gtgctgcagc cgctccggag ctctcggaaa ctttcctccg cgctgtgcgc     240

gggctccctg tcctttctgc tggcgctgct ggtgaggctg gtccgcgggg aggtcggctg     300

tgacctggag cagtgtaagg aggcggcggc ggcggaggag gaggaagcag ccccgggagc     360

agaagggggc gtcttcccgg ggcctcgggg aggtgctccc gggggcggtg cgcggctcag     420

cccctggctg cagccctcgg cgctgctctt cagtctcctg tgtgccttct tctggatggg     480

cttgtacctc ctgcgcgccg gggtgcgcct gcctctggct gtcgcgctgc tggccgcctg     540

ctgcgggggg gaagcgctcg tccagattgg gctgggcgtc ggggaggatc acttactctc     600

actccccgcc gcgggggtgg tgctcagctg cttggccgcc gcgacatggc tggtgctgag     660

gctgaggctg ggcgtcctca tgatcgcctt gactagcgcg gtcaggaccg tgtccctcat     720

ttccttagag aggttcaagg tcgcctggag accttacctg gcgtacctgg ccggcgtgct     780

ggggatcctc ttggccaggt acgtggaaca aatcttgccg cagtccgcgg aggcggctcc     840

aagggagcat ttggggtccc agctgattgc tgggaccaag gaagatatcc cggtgtttaa     900
```

-continued

```
gaggaggagg cggtccagct ccgtcgtgtc cgccgagatg tccggctgca gcagcaagtc    960
ccatcggagg acctccctgc cctgtatacc gagggaacag ctcatggggc attcagaatg   1020
ggaccacaaa cgagggccaa gaggatcaca gtcttcagga accagtatta ctgtggacat   1080
cgccgtcatg ggcgaggccc acggcctcat taccgacctc ctggcagacc cttctcttcc   1140
accaaacgtg tgcacatcct tgagagccgt gagcaacttg ctcagcacac agctcacctt   1200
ccaggccatt cacaagccca gagtgaatcc cgtcacttcg ctcagtgaaa actatacctg   1260
ttctgactct gaagagagct ctgaaaaaga caagcttgct attccaaagc gcctgagaag   1320
gagtttgcct cctggcttgt tgagacgagt ttcttccact tggaccacca ccacctcggc   1380
cacaggtcta cccaccttgg agcctgcacc agtacggaga gaccgcagca ccagcatcaa   1440
actgcaggaa gcaccttcat ccagtcctga ttcttggaat aatccagtga tgatgaccct   1500
caccaaaagc agatccttta cttcatccta tgctatttct gcagctaacc atgtaaaggc   1560
taaaaagcaa agtcgaccag gtgccctcgc taaaatttca cctctttcat cgccctgctc   1620
ctcacctctc caagggactc ctgccagcag cctggtcagc aaaatttctg cagtgcagtt   1680
tccagaatct gctgacacaa ctgccaaaca aagcctaggt tctcacaggg ccttaactta   1740
cactcagagt gccccagacc tatcccctca aatcctgact ccacctgtta tatgtagcag   1800
ctgtggcaga ccatattccc aagggaatcc tgctgatgag cccctggaga gaagtggggt   1860
agccactcgg acaccaagta gaacagatga cactgctcaa gttacctctg attatgaaac   1920
caataacaac agtgacagca gtgacattgt acagaatgaa gatgaaacag agtgcctgag   1980
agagcctctg aggaaagcat cggcttgcag cacctatgct cctgagacca tgatgtttct   2040
ggacaaacca attcttgctc ccgaacctct tgtcatggat aacctggact caattatgga   2100
gcagctaaat acttggaatt ttccaatttt tgatttagtg gaaaatatag gaagaaaatg   2160
tggccgtatt cttagtcagg tatcttacag actttttgaa gacatgggcc tctttgaagc   2220
ttttaaaatt ccaattaggg aatttatgaa ttattttcat gctttggaga ttggatatag   2280
ggatattcct tatcataaca gaatccatgc cactgatgtt ttacatgctg tttggtatct   2340
tactacacag cctattccag gcctctcaac tgtgattaat gatcatggtt caaccagtga   2400
ttcagattct gacagtggat ttacacatgg acatatggga tatgtattct caaaaacgta   2460
taatgtgaca gatgataaat acggatgtct gtctgggaat atccctgcct tggagttgat   2520
ggcgctgtat gtggctgcag ccatgcacga ttatgatcat ccaggaagga ctaatgcttt   2580
cctggttgca actagtgctc ctcaggcggt gctatataac gatcgttcag ttttggagaa   2640
tcatcacgca gctgctgcat ggaatctttt catgtcccgg ccagagtata acttcttaat   2700
taaccttgac catgtggaat ttaagcattt ccgtttcctt gtcattgaag caattttggc   2760
cactgacctg aagaaacact ttgacttcgt agccaaattt aatggcaagg taaatgatga   2820
tgttggaata gattggacca atgaaaatga tcgtctactg gtttgtcaaa tgtgtataaa   2880
gttggctgat atcaatggtc cagctaaatg taaagaactc catcttcagt ggacagatgg   2940
tattgtcaat gaattttatg aacagggtga tgaagaggcc agccttggat tacccataag   3000
ccccttcatg gatcgttctg ctcctcagct ggccaacctt caggaatcct tcatctctca   3060
cattgtgggg cctctgtgca actcctatga ttcagcagga ctaatgcctg gaaaatgggt   3120
ggaagacagc gatgagtcag gagatactga tgacccagaa gaagaggagg aagaagcacc   3180
agcaccaaat gaagaggaaa cctgtgaaaa taatgaatct ccaaaaaaga agactttcaa   3240
```

-continued

```
aaggagaaaa atctactgcc aaataactca gcacctctta cagaaccaca agatgtggaa   3300
gaaagtcatt gaagaggagc aacggttggc aggcatagaa aatcaatccc tggaccagac   3360
ccctcagtcg cactcttcag aacagatcca ggctatcaag gaagaagaag aagagaaagg   3420
gaaaccaaga ggcgaggaga taccaaccca aaagccagac cagtgacaat ggatagaatg   3480
ggctgtgttt ccaaacagat tgacttgtca aagactctct tcaagccagc acaacattta   3540
gacacaacac tgtagaaatt tgagatgggc aaatggctat tgcattttgg gattcttcgc   3600
attttgtgtg tatattttta cagtgaggta cattgttaaa aactttttgc tcaaagaagc   3660
tttcacattg caacaccagc ttctaaggat tttttaagga gggaatatat atgtgtgtgt   3720
gtatataagc tcccacatag atacatgtaa aacatattca cacccatgca cgcacacaca   3780
tacacactga aggccacgat tgctggctcc acaatttagt aacatttata ttaagatata   3840
tatatagtgg tcactgtgat ataataaatc ataaaggaaa ccaaatcaca aaggagatgg   3900
tgtggcttag caaggaaaca gtgcaggaaa tgtaggttac caactaagca gcttttgctc   3960
ttagtactga gggatgaaag ttccagagca ttatttgaat tctgatacat cctgccaaca   4020
ctgtgtgtgt gtgtgtgtgt gtgtgtgtgt gtgtgtgtgt gtgtgaaaga gagacagaag   4080
ggaatggttt gagagggtgc ttgtgtgcat gtgtgtgcat atgtaaagag atttttgtgg   4140
tttaagtaac tcagaatagc tgtagcaaat gactgaatac atgtgaacaa acagaaggaa   4200
gttcactctg gagtgtcttt gggaggcagc cattccaaat gccctcctcc atttagcttc   4260
aataaagggc cttttgctga tggagggcac tcaagggctg ggtgagaggg ccacgtgttt   4320
ggtattacat tactgctatg caccacttga aggagctcta tcaccagcct caaacccgaa   4380
agactgaggc attttccagt ctacttgcct aatgaatgta taggaactgt ctatgagtat   4440
ggatgtcact caactaagat caaatcacca tttaagggga tggcattctt tatacctaaa   4500
cacctaagag ctgaagtcag gtcttttaat caggttagaa ttctaaatga tgccagagaa   4560
ggcttgggaa attgtacttc agcgtgatag cctgtgtctt cttaatttgc tgcaaaatat   4620
gtggtagaga aagaaaagga aacagaaaaa tcactctggg ttatatagca agagatgaag   4680
gagaatattt caacacaggg tttttgtgtt gacataggaa aagcctgatt cttggcaact   4740
gttgtagttt gtctttcagg ggtgaaggtc ccactgacaa cccctgttgt ggtgttccac   4800
acgctgtttg ttggggtagc ttccatcggc agtctggccc attgtcagtc atgcttcttc   4860
tggccgggga gattatagag agattgtttg aagattgggt tattattgaa agtctttttt   4920
tttgtttgtt ttgttttggt ttgtttgttt atctacactt gtttatgctg tgagccaaac   4980
ctctatttaa aaagttgata ctcactttca atattttatt tcatattatt atatatgtca   5040
tgatagttat cttgatgtaa atatgaagat ttttttgttt ctgtagatag taaactcttt   5100
ttttaaaaaa ggaaaaggga aacattttta taaagttata ttttaatcac catttttata   5160
cattgtagtt ctctccaagc ccagtaagag aatgatgatt catttgcatg gaggtcgatg   5220
gacaaccaat catctacctt ttctaattta aatgataatc tgatatagtt ttattgccag   5280
ttaaatgagg atgctgcaaa gcatgttttt tcactagtaa cttttgctaa ctgaatgaat   5340
tctgggtcca tatctcccag atgaaaaact gttaaccaat accatatttt atagttggtg   5400
tccatttctt tccaacactg tttgttatga ttcttccttg agtacttata tacagacctg   5460
ctcattatct aaacaatctt accttctaag taaaccttga ttgtgatttc cagtttttat   5520
tttctctgac gtagtagaaa ggaatgttta cattaaaaat acttttgttt ctcataaatg   5580
gatattgtac tcccccccttt caaagcatta ttttacaata attcatggca ttttaaaaaa   5640
```

-continued

```
taaggcaaag ataatacgac aaaaaatata catggtttca aggcaaattc tccaataagt   5700
tggaaaatgt aaaaaggatc aagtggatgc agcctctacc taaataatta aaatatattt   5760
cagtatattt ctgaattaac accaggtctt cattatttag aacttactaa attgttttca   5820
ttttcttagt tttacctgtg tatctccatg tttgcaaaaa ttactataag tcaaattttg   5880
ccagtgaatt taactatttt tctttccttg caattaaggg gaaaaaagca tttatcttat   5940
cttctcatac cccttgcatc taagtactta gcaaagtcaa tattttccca ttttccaaat   6000
gcgtccatct ctaacataaa tattaattga acatagagct atgtttggag tgagtggact   6060
ggcaggacag ttggaagtcc atcacagtct attgacagtt tcatcaaagc tgtatagtcc   6120
aactagtggg gcagcttggc tactatggtg gaagtctcag caaactgcct ggttttgttt   6180
gtttgttttg ttttaaggta caggaaataa gaggaataat agtggccaaa gcaattagaa   6240
catcttcatt ccagaactgt gttcagcaat ccaggcagat tgatacattt ttctttaaaa   6300
ataaattgct attacagcta gacgtcaatt gggataaata aagggatgaa gatccactaa   6360
gtttgtgact ttcatacaca cccagtacat ctcaaaggat gctaagggac attttctgcc   6420
agtagagttc tccccctttt tggtgacagc aatattatta tgttcacatc taactccaga   6480
gcttacttcc tgtggtgcca atgtatttgt tgcaatttac tacattttta tatgagccta   6540
tttataggtg ccattaaact caggtctttc aaatgaaaga gtttctagcc cacttaggga   6600
aaaagataat tgtttagaaa accataaaat caatggtagg aaaagttgga actggttacc   6660
tggatgccat ggttctctgt taaataaagt aagagaccag gtgtattctg agtgtcatca   6720
gtgttatttt cagcatgcta ataaatgtct ttccggttat atatctatct aaattaacct   6780
ttaaaatatt ggtttccttg ataaaagcac cacttttgct tttgttagct gtaatatttt   6840
ttgtcattta gataagacct ggtttggctc tcaataaaag atgaagacag tagctctgta   6900
cagggatata tctatattag tcttcatctg atgaatgaag aaatttctc atattatgtt    6960
caagaaagta tttacttcct aaaaatagaa ttcccgattc tgtctatttt ggttgaatac   7020
cagaacaaat ctttccgttg caatcccagt aaaacgaaag aaaaggaata tcttacagac   7080
tgttcatatt agatgtatgt agactgttaa tttgcaattt ccccatattt cctgcctatc   7140
ttacccagat aactttcttt gaaggtaaaa gctgtgcaaa aggcatgaga ctcaggccta   7200
ctctttgttt aaatgatgga aaaatataaa ttattttcta agtaataaaa gtataaaaat   7260
tatcattata aataaagtct aaagtttgaa attattaatt taaaaaaaaa aaaaaaaaa    7319

<210> SEQ ID NO 3
<211> LENGTH: 578
<212> TYPE: PRT
<213> ORGANISM: Homo sapiens

<400> SEQUENCE: 3

Met Asn Ile Ser Val Asp Leu Glu Thr Asn Tyr Ala Glu Leu Val Leu
1               5                   10                  15

Asp Val Gly Arg Val Thr Leu Gly Glu Asn Ser Arg Lys Lys Met Lys
            20                  25                  30

Asp Cys Lys Leu Arg Lys Lys Gln Asn Glu Ser Val Ser Arg Ala Met
        35                  40                  45

Cys Ala Leu Leu Asn Ser Gly Gly Gly Val Ile Lys Ala Glu Ile Glu
    50                  55                  60

Asn Glu Asp Tyr Ser Tyr Thr Lys Asp Gly Ile Gly Leu Asp Leu Glu
65                  70                  75                  80
```

-continued

```
Asn Ser Phe Ser Asn Ile Leu Leu Phe Val Pro Glu Tyr Leu Asp Phe
                85                  90                  95

Met Gln Asn Gly Asn Tyr Phe Leu Ile Phe Val Lys Ser Trp Ser Leu
            100                 105                 110

Asn Thr Ser Gly Leu Arg Ile Thr Thr Leu Ser Ser Asn Leu Tyr Lys
        115                 120                 125

Arg Asp Ile Thr Ser Ala Lys Val Met Asn Ala Thr Ala Ala Leu Glu
    130                 135                 140

Phe Leu Lys Asp Met Lys Lys Thr Arg Gly Arg Leu Tyr Leu Arg Pro
145                 150                 155                 160

Glu Leu Leu Ala Lys Arg Pro Cys Val Asp Ile Gln Glu Glu Asn Asn
                165                 170                 175

Met Lys Ala Leu Ala Gly Val Phe Phe Asp Arg Thr Glu Leu Asp Arg
            180                 185                 190

Lys Glu Lys Leu Thr Phe Thr Glu Ser Thr His Val Glu Ile Lys Asn
        195                 200                 205

Phe Ser Thr Glu Lys Leu Leu Gln Arg Ile Lys Glu Ile Leu Pro Gln
    210                 215                 220

Tyr Val Ser Ala Phe Ala Asn Thr Asp Gly Gly Tyr Leu Phe Ile Gly
225                 230                 235                 240

Leu Asn Glu Asp Lys Glu Ile Ile Gly Phe Lys Ala Glu Met Ser Asp
                245                 250                 255

Leu Asp Asp Leu Glu Arg Glu Ile Glu Lys Ser Ile Arg Lys Met Pro
            260                 265                 270

Val His His Phe Cys Met Glu Lys Lys Lys Ile Asn Tyr Ser Cys Lys
        275                 280                 285

Phe Leu Gly Val Tyr Asp Lys Gly Ser Leu Cys Gly Tyr Val Cys Ala
    290                 295                 300

Leu Arg Val Glu Arg Phe Cys Cys Ala Val Phe Ala Lys Glu Pro Asp
305                 310                 315                 320

Ser Trp His Val Lys Asp Asn Arg Val Met Gln Leu Thr Arg Lys Glu
                325                 330                 335

Trp Ile Gln Phe Met Val Glu Ala Glu Pro Lys Phe Ser Ser Ser Tyr
            340                 345                 350

Glu Glu Val Ile Ser Gln Ile Asn Thr Ser Leu Pro Ala Pro His Ser
        355                 360                 365

Trp Pro Leu Leu Glu Trp Gln Arg Gln Arg His His Cys Pro Gly Leu
    370                 375                 380

Ser Gly Arg Ile Thr Tyr Thr Pro Glu Asn Leu Cys Arg Lys Leu Phe
385                 390                 395                 400

Leu Gln His Glu Gly Leu Lys Gln Leu Ile Cys Glu Glu Met Asp Ser
                405                 410                 415

Val Arg Lys Gly Ser Leu Ile Phe Ser Arg Ser Trp Ser Val Asp Leu
            420                 425                 430

Gly Leu Gln Glu Asn His Lys Val Leu Cys Asp Ala Leu Leu Ile Ser
        435                 440                 445

Gln Asp Ser Pro Pro Val Leu Tyr Thr Phe His Met Val Gln Asp Glu
    450                 455                 460

Glu Phe Lys Gly Tyr Ser Thr Gln Thr Ala Leu Thr Leu Lys Gln Lys
465                 470                 475                 480

Leu Ala Lys Ile Gly Gly Tyr Thr Lys Lys Val Cys Val Met Thr Lys
                485                 490                 495
```

-continued

```
Ile Phe Tyr Leu Ser Pro Glu Gly Met Thr Ser Cys Gln Tyr Asp Leu
            500                 505                 510

Arg Ser Gln Val Ile Tyr Pro Glu Ser Tyr Tyr Phe Thr Arg Arg Lys
        515                 520                 525

Tyr Leu Leu Lys Ala Leu Phe Lys Ala Leu Lys Arg Leu Lys Ser Leu
    530                 535                 540

Arg Asp Gln Phe Ser Phe Ala Glu Asn Leu Tyr Gln Ile Ile Gly Ile
545                 550                 555                 560

Asp Cys Phe Gln Lys Asn Asp Lys Lys Met Phe Lys Ser Cys Arg Arg
                565                 570                 575

Leu Thr


<210> SEQ ID NO 4
<211> LENGTH: 2530
<212> TYPE: DNA
<213> ORGANISM: Homo sapiens

<400> SEQUENCE: 4

tttgtaactt cacttcagcc tcccattgat cgctttctgc aaccattcag actgatctcg      60

ggctcctatt tcatttacat tgtgtgcaca ccaagtaacc agtgggaaaa ctttagaggg     120

tacttaaacc ccagaaaatt ctgaaaccgg gctcttgagc cgctatcctc gggcctgctc     180

ccaccctgtg gagtgcactt tcgttttcaa taaatctctg cttttgttgc ttcattcttt     240

ccttgctttg tttgtgtgtt tgtccagttc tttgttcaac acgccaagaa cctggacact     300

cttcactggt aacatatttt ggcaagccaa ccaggagaaa agaatttctg cttggacact     360

gcatagctgc tgggaaaatg aacatcagtg ttgatttgga aacgaattat gccgagttgg     420

ttctagatgt gggaagagtc actcttggag agaacagtag gaaaaaaatg aaggattgta     480

aactgagaaa aaagcagaat gaaagtgtct cacgagctat gtgtgctctg ctcaattctg     540

gagggggagt gatcaaggct gaaattgaga atgaagacta tagttataca aaagatggaa     600

taggactaga tttggaaaat tcttttagta acattctgtt atttgttcct gagtacttag     660

acttcatgca gaatggtaac tactttctga tttttgtgaa gtcatggagc ttgaacacct     720

ctggtctgcg gattaccacc ttgagctcca atttgtacaa aagagatata acatctgcaa     780

aagtcatgaa tgccactgct gcactggagt tcctcaaaga catgaaaaag actagaggga     840

gattgtattt aagaccagaa ttgctggcaa agaggccctg tgttgatata caagaagaaa     900

ataacatgaa ggccttggcc ggggtttttt ttgatagaac agaacttgat cggaaagaaa     960

aattgacctt tactgaatcc acacatgttg aaattaaaaa cttctcgaca gaaaagttgt    1020

tacaacgaat taaagagatt ctccctcaat atgtttctgc atttgcaaat actgatggag    1080

gatatttgtt cattggttta aatgaagata aagaaataat tggctttaaa gcagagatga    1140

gtgacctcga tgacttagaa agagaaatcg aaaagtccat taggaagatg cctgtgcatc    1200

acttctgtat ggagaagaag aagataaatt attcatgcaa attccttgga gtatatgata    1260

aaggaagtct ttgtggatat gtctgtgcac tcagagtgga gcgcttctgc tgtgcagtgt    1320

ttgctaaaga gcctgattcc tggcatgtga aagataaccg tgtgatgcag ttgaccagga    1380

aggaatggat ccagttcatg gtggaggctg aaccaaaatt ttccagttca tatgaagagg    1440

tgatctctca aataaatacg tcattacctg ctccccacag ttggcctctt ttggaatggc    1500

aacggcagag acatcactgt ccagggctat caggaaggat aacgtatact ccagaaaacc    1560

tttgcagaaa actgttctta caacatgaag gacttaagca attaatatgt gaagaaatgg    1620
```

actctgtcag aaagggctca ctgatcttct ctaggagctg gtctgtggat ctgggcttgc 1680
aagagaacca caaagtcctc tgtgatgctc ttctgatttc ccaggacagt cctccagtcc 1740
tatacacctt ccacatggta caggatgagg agtttaaagg ctattctaca caaactgccc 1800
taaccttaaa gcagaagctg gcaaaaattg gtggttacac taaaaaagtg tgtgtcatga 1860
caaagatctt ctacttgagc cctgaaggca tgacaagctg ccagtatgat ttaaggtcgc 1920
aagtaattta ccctgaatcc tactatttta caagaaggaa atacttgctg aaagcccttt 1980
ttaaagcctt aaagagactc aagtctctga gagaccagtt ttcctttgca gaaaatctat 2040
accagataat cggtatagat tgctttcaga agaatgataa aaagatgttt aaatcttgtc 2100
gaaggctcac ctgatggaaa atggactggg ctactgagat atttttcatt atatatttga 2160
taacattctc taattctgtg aaaatatttc tttgaaaact ttgcaagtta agcaacttaa 2220
tgtgatgttg gataattggg ttttgtctat tttcacttct ccctaaataa tcttcacaga 2280
tattgtttga gggatattag gaaaattaat ttgttaactc gtctgtgcac agtattattt 2340
actctgtctg tagttcctga ataaattttc ttccatgctt gaactgggaa aattgcaaca 2400
cttttattct taatgacaac agtgaaaatc tcccagcata tacctagaaa acaattataa 2460
cttacaaaag attatccttg atgaaactca gaatttccac agtgggaatg aataagaagg 2520
caaaactcat 2530

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 5
caccgttttc actgagcgaa gtga 24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 6
aaactcactt cgctcagtga aaac 24

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 7
caccgagaca agcttgctat tccaa 25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide -continued

```
<400> SEQUENCE: 8

aaacttggaa tagcaagctt gtctc                                          25


<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9

caccggcact ctgagtgtaa gtta                                           24


<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10

aaactaactt acactcagag tgcc                                           24
```